United States Patent
Burich et al.

(10) Patent No.: US 12,374,437 B2
(45) Date of Patent: Jul. 29, 2025

(54) GROUP PERFORMANCE MONITORING SYSTEM AND METHOD

(71) Applicant: adidas AG, Herzogenaurach (DE)

(72) Inventors: Meg Susan Burich, Chadds Ford, PA (US); Qaizar Hassonjee, Chadds Ford, PA (US); Roger Armitage, Cirencester (GB); Markus Strecker, Landenberg, PA (US); Hagen Diesterbeck, Forchheim (DE)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 18/352,713

(22) Filed: Jul. 14, 2023

(65) Prior Publication Data

US 2024/0029854 A1 Jan. 25, 2024

Related U.S. Application Data

(63) Continuation of application No. 17/208,767, filed on Mar. 22, 2021, now Pat. No. 11,721,423, which is a continuation of application No. 16/722,948, filed on Dec. 20, 2019, now Pat. No. 10,957,439, which is a continuation of application No. 15/912,940, filed on Mar. 6, 2018, now Pat. No. 10,576,329, which is a
(Continued)

(51) Int. Cl.
*G16H 20/30* (2018.01)
*A63B 24/00* (2006.01)
*A63B 71/06* (2006.01)
*G16H 40/67* (2018.01)

(52) U.S. Cl.
CPC ......... *G16H 20/30* (2018.01); *A63B 24/0062* (2013.01); *A63B 71/06* (2013.01); *G16H 40/67* (2018.01); *A63B 2024/0065* (2013.01)

(58) Field of Classification Search
CPC .... G16H 20/30; G16H 40/67; A63B 24/0062; A63B 71/06; A63B 2024/0065
See application file for complete search history.

(56) References Cited

U.S. PATENT DOCUMENTS

| | | | |
|---|---|---|---|
| 2,571,442 | A | 10/1951 | Griffith |
| 3,307,546 | A | 3/1967 | Cherio et al. |

(Continued)

FOREIGN PATENT DOCUMENTS

| | | |
|---|---|---|
| CN | 101753852 A | 6/2010 |
| EP | 1134555 A1 | 9/2001 |

(Continued)

OTHER PUBLICATIONS

Garmin Corporation, "GPS II: Owner's Manual & Reference (Garmin)," 1996.
(Continued)

*Primary Examiner* — Reginald A Renwick
(74) *Attorney, Agent, or Firm* — Sterne, Kessler, Goldstein & Fox P.L.L.C.

(57) ABSTRACT

The present invention provides group performance monitoring systems and methods. In one exemplary embodiment, a group monitoring device includes a display configured to display, during an athletic activity, a plurality of individual performance metrics relating to a plurality of individuals engaged in the athletic activity, each individual performance metric relating to one of the plurality of individuals; and an input to manipulate the display.

21 Claims, 58 Drawing Sheets

Related U.S. Application Data continuation of application No. 15/487,197, filed on Apr. 13, 2017, now Pat. No. 9,937,383, which is a continuation of application No. 14/829,120, filed on Aug. 18, 2015, now Pat. No. 9,630,059, which is a continuation of application No. 13/077,510, filed on Mar. 31, 2011, now Pat. No. 9,141,759.

(56) References Cited

U.S. PATENT DOCUMENTS

| | | |
|---|---|---|
| 3,534,727 A | 10/1970 | Roman |
| 3,874,368 A | 4/1975 | Asrican |
| 3,926,177 A | 12/1975 | Hardway, Jr. et al. |
| 4,016,868 A | 4/1977 | Allison |
| 4,033,332 A | 7/1977 | Hardway, Jr. et al. |
| 4,102,331 A | 7/1978 | Grayzel et al. |
| 4,202,350 A | 5/1980 | Walton |
| 4,289,142 A | 9/1981 | Kearns |
| 4,308,872 A | 1/1982 | Watson et al. |
| 4,312,358 A | 1/1982 | Barney |
| 4,373,534 A | 2/1983 | Watson |
| 4,387,722 A | 6/1983 | Kearns |
| 4,494,553 A | 1/1985 | Sciarra et al. |
| 4,572,197 A | 2/1986 | Moore et al. |
| 4,580,572 A | 4/1986 | Granek et al. |
| 4,753,088 A | 6/1988 | Harrison et al. |
| 4,777,962 A | 10/1988 | Watson et al. |
| 4,815,473 A | 3/1989 | Watson et al. |
| 4,817,625 A | 4/1989 | Miles |
| 4,889,131 A | 12/1989 | Salem et al. |
| 4,909,260 A | 3/1990 | Salem et al. |
| 4,962,469 A | 10/1990 | Ono et al. |
| 5,007,427 A | 4/1991 | Suzuki et al. |
| 5,074,129 A | 12/1991 | Matthew |
| 5,076,801 A | 12/1991 | Schroll |
| 5,099,855 A | 3/1992 | Yount |
| 5,111,818 A | 5/1992 | Suzuki et al. |
| 5,143,089 A | 9/1992 | Alt |
| 5,148,002 A | 9/1992 | Kuo et al. |
| 5,153,584 A | 10/1992 | Engira |
| 5,204,670 A | 4/1993 | Stinton |
| 5,210,540 A | 5/1993 | Masumoto |
| 5,241,300 A | 8/1993 | Buschmann |
| 5,295,490 A | 3/1994 | Dodakian |
| 5,329,932 A | 7/1994 | Yount |
| 5,348,008 A | 9/1994 | Bornn et al. |
| 5,353,793 A | 10/1994 | Bornn |
| 5,400,254 A | 3/1995 | Fujita |
| 5,416,961 A | 5/1995 | Vinay |
| 5,428,546 A | 6/1995 | Shah et al. |
| 5,454,376 A | 10/1995 | Stephens et al. |
| 5,583,776 A | 12/1996 | Levi et al. |
| 5,611,085 A | 3/1997 | Rasmussen |
| 5,664,780 A | 9/1997 | Bricker |
| 5,724,025 A | 3/1998 | Tavori |
| 5,758,313 A | 5/1998 | Shah et al. |
| 5,769,755 A | 6/1998 | Henry et al. |
| 5,782,778 A | 7/1998 | De Briere et al. |
| 5,820,567 A | 10/1998 | Mackie |
| 5,862,511 A | 1/1999 | Croyle et al. |
| 5,906,547 A | 5/1999 | Tynan |
| 5,907,291 A | 5/1999 | Chen et al. |
| 5,937,854 A | 8/1999 | Stenzler |
| 5,991,922 A | 11/1999 | Banks |
| 6,002,982 A | 12/1999 | Fry |
| 6,047,203 A | 4/2000 | Sackner et al. |
| 6,066,093 A | 5/2000 | Kelly et al. |
| 6,144,375 A | 11/2000 | Jain et al. |
| 6,145,551 A | 11/2000 | Jayaraman et al. |
| 6,148,262 A | 11/2000 | Fry |
| 6,179,786 B1 | 1/2001 | Young |
| 6,198,394 B1 | 3/2001 | Jacobsen et al. |
| 6,246,362 B1 | 6/2001 | Tsubata et al. |
| 6,254,551 B1 | 7/2001 | Varis |
| 6,259,944 B1 | 7/2001 | Margulis et al. |
| 6,266,623 B1 | 7/2001 | Vock et al. |
| 6,287,264 B1 | 9/2001 | Hoffman |
| 6,306,088 B1 | 10/2001 | Krausman et al. |
| 6,341,504 B1 | 1/2002 | Istook |
| 6,381,482 B1 | 4/2002 | Jayaraman et al. |
| 6,419,636 B1 | 7/2002 | Young et al. |
| 6,424,295 B1 | 7/2002 | Lange |
| 6,443,890 B1 | 9/2002 | Schulze et al. |
| 6,461,307 B1 | 10/2002 | Kristbjanarson et al. |
| 6,463,385 B1 | 10/2002 | Fry |
| 6,478,736 B1 | 11/2002 | Mault |
| 6,513,532 B2 | 2/2003 | Mault et al. |
| 6,522,531 B1 | 2/2003 | Quintana et al. |
| 6,529,827 B1 | 3/2003 | Beason et al. |
| 6,551,252 B2 | 4/2003 | Sackner et al. |
| 6,579,231 B1 | 6/2003 | Phipps |
| 6,616,613 B1 | 9/2003 | Goodman |
| 6,687,523 B1 | 2/2004 | Jayaramen et al. |
| 6,710,713 B1 | 3/2004 | Russo |
| 6,790,178 B1 | 9/2004 | Mault et al. |
| 6,798,378 B1 | 9/2004 | Walters |
| 6,902,513 B1 | 6/2005 | McClure |
| 6,941,775 B2 | 9/2005 | Sharma |
| 6,970,731 B1 | 11/2005 | Jayaraman et al. |
| 7,207,853 B2 | 4/2007 | Spencer et al. |
| 7,254,516 B2 | 8/2007 | Case, Jr. et al. |
| 7,559,902 B2 | 7/2009 | Ting et al. |
| 7,604,603 B2 | 10/2009 | Sackner et al. |
| 7,670,263 B2 | 3/2010 | Ellis et al. |
| 7,670,295 B2 | 3/2010 | Sackner et al. |
| 7,715,982 B2 | 5/2010 | Grenfell et al. |
| 8,033,959 B2 | 10/2011 | Oleson et al. |
| 8,105,208 B2 | 1/2012 | Oleson et al. |
| 8,200,323 B2 | 6/2012 | Dibenedetto et al. |
| 8,241,184 B2 | 8/2012 | Dibenedetto et al. |
| 8,466,794 B2 | 6/2013 | Mack et al. |
| 8,477,046 B2 | 7/2013 | Alonso |
| 8,818,478 B2 | 8/2014 | Scheffler et al. |
| 9,185,361 B2 | 11/2015 | Curry |
| 9,406,336 B2 | 8/2016 | Bose et al. |
| 9,750,429 B1 | 9/2017 | Sackner et al. |
| 2001/0040591 A1 | 11/2001 | Abbott et al. |
| 2002/0032386 A1 | 3/2002 | Sackner et al. |
| 2002/0116147 A1 | 8/2002 | Vock et al. |
| 2003/0049590 A1 | 3/2003 | Feldbau |
| 2003/0095186 A1 | 5/2003 | Aman et al. |
| 2004/0010420 A1 | 1/2004 | Rooks |
| 2004/0176674 A1 | 9/2004 | Nazeri |
| 2004/0186390 A1 | 9/2004 | Ross et al. |
| 2004/0212545 A1 | 10/2004 | Li et al. |
| 2005/0054941 A1 | 3/2005 | Ting et al. |
| 2005/0073283 A1 | 4/2005 | Friedli et al. |
| 2006/0074338 A1 | 4/2006 | Greenwald et al. |
| 2006/0143645 A1 | 6/2006 | Vock et al. |
| 2006/0189852 A1 | 8/2006 | Greenwald et al. |
| 2007/0063850 A1 | 3/2007 | Devaul et al. |
| 2007/0191083 A1 | 8/2007 | Kuenzler et al. |
| 2007/0219059 A1 | 9/2007 | Schwartz et al. |
| 2007/0240190 A1 | 10/2007 | Arseneau et al. |
| 2008/0015454 A1 | 1/2008 | Gal |
| 2008/0033581 A1 | 2/2008 | Doshi et al. |
| 2008/0162352 A1 | 7/2008 | Gizewski |
| 2008/0192116 A1 | 8/2008 | Tamir et al. |
| 2008/0206726 A1 | 8/2008 | Kalisvaart et al. |
| 2008/0219319 A1 | 9/2008 | Buckalew |
| 2008/0269016 A1 | 10/2008 | Ungari et al. |
| 2009/0054751 A1 | 2/2009 | Babashan et al. |
| 2009/0189982 A1 | 7/2009 | Tawiah |
| 2009/0216556 A1 | 8/2009 | Martin et al. |
| 2009/0233771 A1 | 9/2009 | Quatrochi et al. |
| 2010/0035688 A1* | 2/2010 | Picunko ............ G01S 1/7034 463/30 |
| 2010/0152545 A1 | 6/2010 | Ramsay et al. |
| 2010/0184563 A1 | 7/2010 | Molyneux et al. |
| 2010/0184564 A1 | 7/2010 | Molyneux et al. |
| 2010/0274100 A1 | 10/2010 | Behar et al. |
| 2010/0292050 A1 | 11/2010 | Dibenedetto et al. |
| 2011/0013087 A1 | 1/2011 | House et al. |
| 2011/0054270 A1 | 3/2011 | Derchak |

(56) References Cited

U.S. PATENT DOCUMENTS

| | | |
|---|---|---|
| 2011/0054271 A1 | 3/2011 | Derchak et al. |
| 2011/0054272 A1 | 3/2011 | Derchak |
| 2011/0054289 A1 | 3/2011 | Derchak et al. |
| 2011/0054290 A1 | 3/2011 | Derchak |
| 2011/0087115 A1 | 4/2011 | Sackner et al. |
| 2011/0105861 A1 | 5/2011 | Derchak et al. |
| 2011/0130643 A1 | 6/2011 | Derchak et al. |
| 2011/0181419 A1 | 7/2011 | Mack et al. |
| 2011/0181420 A1 | 7/2011 | Mack et al. |
| 2011/0269517 A1 | 11/2011 | Englert et al. |
| 2011/0275940 A1 | 11/2011 | Nims et al. |
| 2011/0304497 A1 | 12/2011 | Molyneux et al. |
| 2012/0029666 A1 | 2/2012 | Crowley et al. |
| 2012/0081531 A1 | 4/2012 | DeAngelis et al. |
| 2012/0095356 A1 | 4/2012 | Oleson et al. |
| 2012/0184367 A1 | 7/2012 | Parrott et al. |
| 2012/0210498 A1 | 8/2012 | Mack |
| 2012/0235821 A1 | 9/2012 | Dibenedetto et al. |
| 2012/0244995 A1 | 9/2012 | Dibenedetto et al. |
| 2012/0246795 A1 | 10/2012 | Scheffler et al. |
| 2012/0253484 A1 | 10/2012 | Burich et al. |
| 2012/0253485 A1 | 10/2012 | Weast et al. |
| 2012/0254934 A1 | 10/2012 | McBrearty et al. |
| 2012/0274469 A1 | 11/2012 | Oleson et al. |
| 2012/0290109 A1 | 11/2012 | Engelberg et al. |
| 2013/0066236 A1 | 3/2013 | Herman et al. |
| 2013/0198694 A1 | 8/2013 | Rahman et al. |
| 2013/0225309 A1 | 8/2013 | Bentley et al. |
| 2013/0245966 A1 | 9/2013 | Burroughs |
| 2015/0375085 A1* | 12/2015 | Molyneux .......... A63B 24/0021 2/22 |
| 2017/0095716 A1 | 4/2017 | Lewis et al. |
| 2017/0274247 A1 | 9/2017 | Miyasaka et al. |

FOREIGN PATENT DOCUMENTS

| | | |
|---|---|---|
| EP | 2108311 A1 | 10/2009 |
| GB | 2259772 | 3/1993 |
| GB | 2 387 052 A | 10/2003 |
| JP | S63-288173 A | 11/1988 |
| JP | H07-124282 A | 5/1995 |
| JP | 10-314357 A | 12/1998 |
| JP | 2003-175139 A | 6/2003 |
| JP | 2008-524589 A | 7/2008 |
| JP | 2010-264246 A | 11/2010 |
| JP | 2011-505202 A | 2/2011 |
| WO | WO 99/30613 | 6/1999 |
| WO | WO 02/067449 A2 | 8/2002 |
| WO | WO 2006/065679 A2 | 6/2006 |
| WO | WO 2009/073610 A2 | 6/2009 |
| WO | WO 2009/108887 A2 | 9/2009 |
| WO | WO 2009/111472 A2 | 9/2009 |
| WO | WO 2010/065836 A2 | 6/2010 |
| WO | WO 2010/065886 A1 | 6/2010 |
| WO | WO 2011/028383 A1 | 3/2011 |

OTHER PUBLICATIONS

SVG. "Stats SportVU Hits Big Time With UEFA Champions League." http://www.sportvu.com/pdfs/pr_4810_svg.pdf. Created and Published Apr. 8, 2010.

Infosthetics. "Adidas Match Tracker: Experience Soccer Games Like a Data Geek." http://infosthetics.com/archives/2010/05/adidas_ match_tracker_experience_a_soccer_ga me_like_a_data_geek. html. Created and Published May 26, 2010.

The New York Times, "Mexico Escapes With a Tie Against South Africa," http://goal.blogs.nytimes.com/2010/06/11/live-analysis-south-africa-vs-mexico/?_r=0. Created and Published Jun. 11, 2010.

Infosthetics. "ScoreGrid: More Visualized Real-Time Football Cup Data Statistics" http://infosthetics.com/archives/2010/06/ scoregrid _more_football_cup_data_statistics_visualization.html. Created and Published Jun. 17, 2010.

European Search Report for European Application No. 12 162817, European Patent Office, Munich, dated Sep. 29, 2012, 5 pages.

Revised Petition to Institute Derivation Proceeding referencing U.S. Appl. No. 13/077,510, filed in Case No. DER2014-00006 with the Patent Trial and Appeal Board on Nov. 21, 2013.

European Search Report for European Application No. 13175499.6, European Patent Office, Munich, Germany, dated Jan. 5, 2015, 7 pages.

Revised Petition to Institute Derivation Proceeding referencing U.S. Appl. No. 13/543,428, filed in Case No. DER2014-00005 with the Patent Trial and Appeal Board on Nov. 21, 2013.

* cited by examiner

GROUP PERFORMANCE MONITORING SYSTEM AND METHOD

CROSS-REFERENCE TO RELATED APPLICATION

This application is continuation of U.S. application Ser. No. 17/208,767, filed Mar. 22, 2021, which is a continuation of U.S. application Ser. No. 16/722,948, filed Dec. 20, 2019, now U.S. Pat. No. 10,957,439, issued Mar. 23, 2021, which is a continuation of U.S. application Ser. No. 15/912,940, filed Mar. 6, 2018, now U.S. Pat. No. 10,576,329, issued Mar. 3, 2020, which is a continuation of U.S. application Ser. No. 15/487,197, filed Apr. 13, 2017, now U.S. Pat. No. 9,937,383, issued Apr. 10, 2018, which is a continuation of U.S. application Ser. No. 14/829,120, filed Aug. 18, 2015, now U.S. Pat. No. 9,630,059, issued Apr. 25, 2017, which is a continuation of U.S. application Ser. No. 13/077,510, filed Mar. 31, 2011, now U.S. Pat. No. 9,141,759, issued Sep. 22, 2015. These applications are incorporated herein by reference in their entireties.

BACKGROUND OF THE INVENTION

Field of the Invention

The present invention generally relates to an activity monitoring system, and in particular, to an athletic activity monitoring system that facilitates live monitoring of a plurality of individuals.

Background Art

Exercise is important to maintaining a healthy lifestyle and individual well-being. A common way for individuals to exercise is to participate in athletic activities, such as, for example, sports and training programs. A session of athletic activity may include, for example, a training session or a competitive session such as, for example, a soccer match or basketball game. When participating in athletic activities in a competitive or collaborative environment, one's performance may be dependent on the performance of other individuals. For example, in a team sport context, the performance of various athletic movements and endeavors may be influenced by the athletic movements and endeavors of teammates or adversaries. Often, a trainer (e.g., a coach) is monitoring such athletic activity.

To effectively monitor the athletic activity, the trainer, or other individual, typically gathers information about the participants in the athletic activity by viewing the athletic activity from, for example, the sidelines of a sports field. Thus, the information used to make decisions that influence the athletic activity is typically limited by what is observed by the trainer from the sidelines. A trainer may have assistants to help with this observation, or multiple trainers may work together, however there remains difficulty in monitoring a plurality of individuals so as to effectively track and manage performance of individuals during an athletic activity.

BRIEF SUMMARY OF THE INVENTION

The present invention provides group performance monitoring systems and methods. In one exemplary embodiment, a system for monitoring a plurality of individuals engaged in an athletic activity includes a group monitoring device, including a display configured to display, during an athletic activity, a plurality of individual performance metrics relating to a plurality of individuals engaged in the athletic activity, each individual performance metric relating to one of the plurality of individuals, and an input to manipulate the display.

In one exemplary embodiment, a method for monitoring a plurality of individuals engaged in an athletic activity includes displaying during the athletic activity a plurality of individual performance metric information relating to a plurality of individuals engaged in the athletic activity, each performance metric relating to one of the plurality of individuals, providing first and second analysis markers adapted to be manipulated by a user to define a subset of the displayed performance metric information as a function of an interval parameter, and displaying performance metric information corresponding to only the subset of the displayed performance metric information defined by the analysis markers for each of the plurality of individuals.

In one exemplary embodiment, a computer program product including computer-useable medium having computer program logic recorded thereon that, when executed by one or more processors, provides to a user performance information related to an athletic activity engaged in by a plurality of individuals, where the computer program logic includes first computer readable program code that enables a processor to display during the athletic activity a plurality of individual performance metric information relating to a plurality of individuals engaged in the athletic activity, each performance metric relating to one of the plurality of individuals, second computer readable program code that enables a processor to provide first and second analysis markers adapted to be manipulated by a user to define a subset of the displayed performance metric information as a function of an interval parameter, and third computer readable program code that enables a processor to display performance metric information corresponding to only the subset of the displayed performance metric information defined by the analysis markers for each of the plurality of individuals.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention. In the drawings, like reference numbers, letters, or renderings indicate identical or functionally similar elements.

FIG. 17 depicts a display of a group monitoring device according to an exemplary embodiment of the present invention.

FIG. 18 depicts a display of a group monitoring device according to an exemplary embodiment of the present invention.

FIG. 48 depicts a display of a group monitoring device according to an exemplary embodiment of the present invention.

Figure 49:
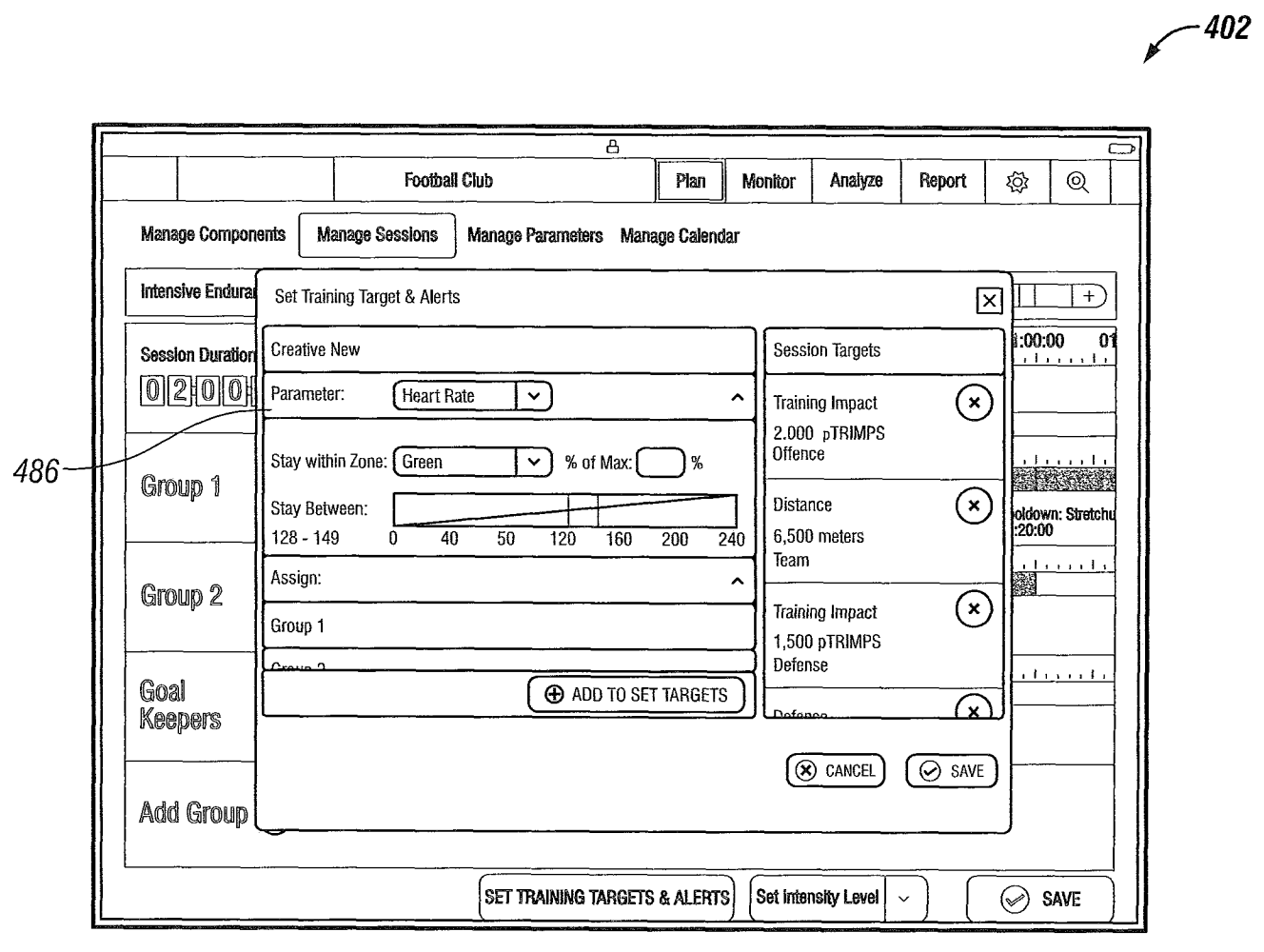

FIG. 49 depicts a display of a group monitoring device according to an exemplary embodiment of the present invention.

FIG. 51 depicts a display of a group monitoring device according to an exemplary embodiment of the present invention.

DETAILED DESCRIPTION OF THE INVENTION

Figure 1:
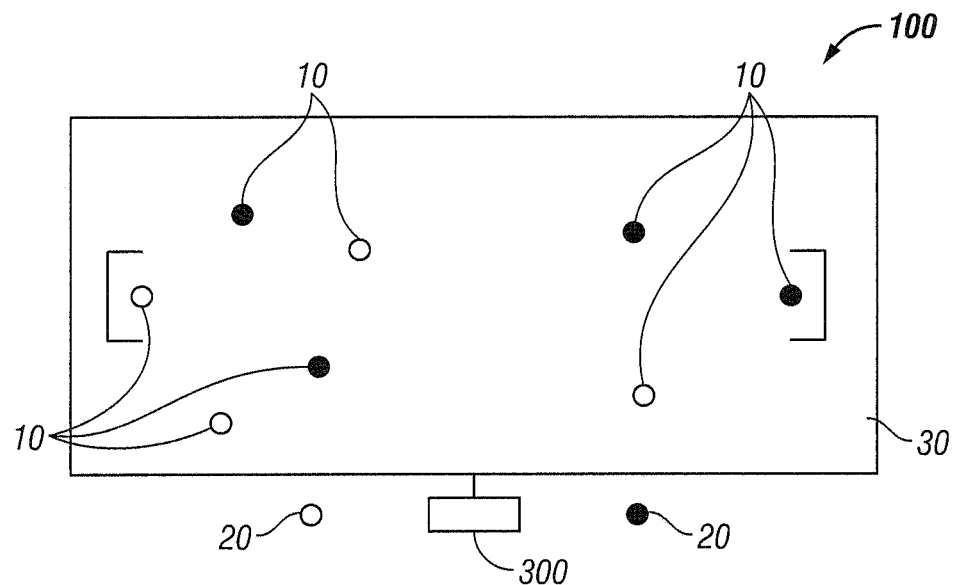
FIG. 1 depicts a monitoring system according to an exemplary embodiment of the present invention.

The present invention will now be described in detail with reference to embodiments thereof as illustrated in the accompanying drawings. References to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The term "invention" or "present invention" as used herein is a non-limiting term and is not intended to refer to any single embodiment of the particular invention but encompasses all possible embodiments as described in the application.

Various aspects of the present invention, or any parts or functions thereof, may be implemented using hardware, software, firmware, tangible computer readable or computer usable storage media having instructions stored thereon, or a combination thereof, and may be implemented in one or more computer systems or other processing systems.

Individuals participating in an athletic activity and trainers (e.g., a coach, physician, or other authorized individual) may work together during a session of athletic activity for a variety of reasons. For example, it may be desired that the trainer monitors the performance of the individuals and makes recommendations or otherwise influences their performance in order to maximize the individuals' fitness level. Alternatively or additionally, it may be desired that the trainer monitors and influences the individuals to help maximize the effectiveness of the individuals in the athletic activity. Further, it may be desired that the trainer monitors and influences the individuals to help maximize the probability of success in the athletic activity (where success may be, for example, defeating an opposing team in a game, such as, for example, soccer, or achieving/maintaining a desired level of fitness for one or more individuals participating in the athletic activity). A session of athletic activity may include, for example, a training session (e.g., a field session, a gym session, a track session) or a competitive session (e.g., a soccer match or a basketball game)

In some exemplary embodiments, the trainer may monitor and influence the individuals in order to track and maintain the individuals' health and safety. In such an embodiment, it may be beneficial for the trainer to be provided with information relating to health and safety, for example, injuries, illnesses, and dangerous conditions.

The trainer must consider these and other goals, monitor the individuals, and make decisions to influence the performance of the individuals both individually and as a group. In doing so, the trainer depends on information about the individuals and their performance while participating in a session of athletic activity. The trainer may benefit from receipt of information in addition to that which is directly observable by the trainer. A group monitoring system according to an exemplary embodiment of the present invention can provide the trainer with easy-to-understand information about individuals participating in the athletic activity, beyond that which can be directly observed, thereby facilitating quick and effective decision-making by the trainer to maximize the probability of achieving success in the athletic activity. In an exemplary embodiment, the group monitoring system can provide alerts to the trainer to flag critical or important conditions that the trainer would not otherwise be able to observe directly, such as, for example, fatigue of an individual or heart rate of an individual being above a threshold value.

Figure 2:
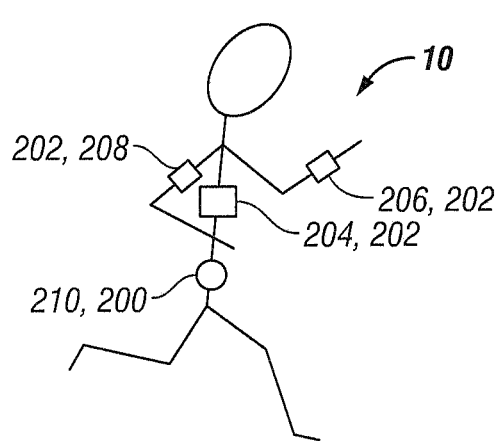
FIG. 2 depicts an individual monitor and associated components according to an exemplary embodiment of the present invention.
Figure 3:
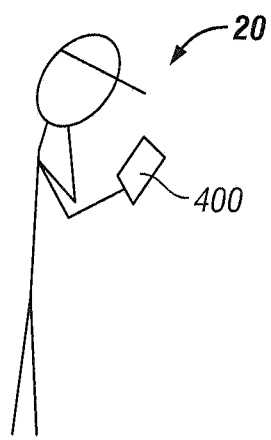
FIG. 3 depicts an exemplary group monitoring device according to an exemplary embodiment of the present invention.
Figure 11:
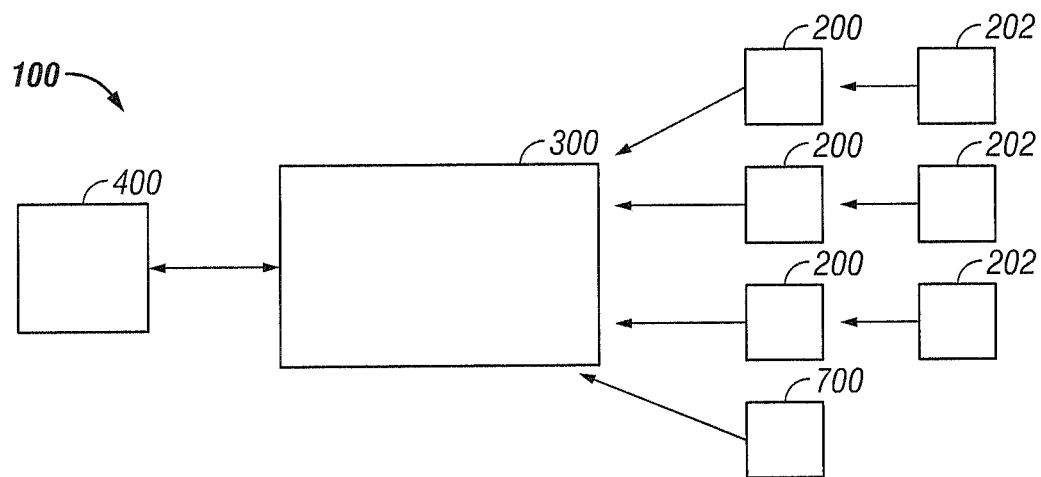
FIG. 11 depicts a diagram of a portion of a monitoring system according to an exemplary embodiment of the present invention.

In an exemplary embodiment, group monitoring system 100, depicted in, for example, FIGS. 1 and 11, includes individual monitors 200 (see FIG. 2), a base station 300, and at least one group monitoring device 400 (see FIG. 3). Individual monitor 200 may be coupled to an individual 10, as shown in FIG. 2. Individual monitor 200 may include or be in communication with a variety of sensors 202, including, but not limited to, an accelerometer, a pedometer, a heart rate monitor, a position sensor, an impact sensor, a camera, a magnetometer, a gyroscope, a microphone, a temperature sensor, and a wind sensor. In an exemplary embodiment, individual monitor 200 may include a sensor garment 204, a heart rate monitor 206, and a position sensor 208. Position sensor 208 may include, for example, a position sensor for use with a satellite-based positioning system (e.g., GPS (global positioning system)), a position sensor for use with a beacon system (e.g., position determination using triangulation and/or time differences of signals received by antennas at known positions about a field or activity area), or a position sensor for use with any other suitable position-determining system. In some exemplary embodiments, group monitoring device 400 may be used by a trainer 20, as shown in FIG. 3. In an exemplary embodiment, individual monitor 200 may include a monitoring system such as, for example, those disclosed in U.S. patent application Ser. No. 12/467,944 and U.S. patent application Ser. No. 12/467,948, each of which is incorporated herein in its entirety by reference thereto.

Generally, sensors 202 are mounted to individuals 10 in preparation for participation by individuals 10 in a session of athletic activity. Sensors 202 mounted to a particular individual 10 are coupled, either via wires or wirelessly, to individual monitor 200, also mounted on the particular individual 10. Sensors 202 sense characteristics about individual 10 during participation by individual 10 in the session of athletic activity, and transmit data indicative of the characteristics to individual monitor 200. Individual monitor 200 in turn transmits the data to base station 300 during the session of athletic activity.

In some exemplary embodiments, this transmission occurs in real time. "Real time" as used herein may include delays inherent to transmission technology, delays designed to optimize resources, and other inherent or desirable delays that would be apparent to one of skill in the art. In some exemplary embodiments, this transmission is delayed from real time, or may occur after completion of the activity. Base station 300 receives the data and determines metrics from the data, where the metrics may be representations of the characteristics measured by sensors 202, or may be representations of further characteristics derived from the data through the use of algorithms and other data manipulation techniques. Base station 300 in turn transmits the metrics during the session of athletic activity to group monitoring device 400, which receives the metrics and displays a representation of the metrics.

Group monitoring device 400 may receive metrics associated with a plurality of individuals 10, and may display the received metrics in association with the individual 10 with which they are associated. In this way, trainer 20 viewing group monitoring device 400 during the session of athletic activity receives detailed information about multiple individuals 10, and can act on that information as it is determined necessary or expedient, thereby efficiently monitoring and managing individuals 10 during the session of athletic activity.

In some exemplary embodiments, individual monitors 200 calculate metrics based on the data, and transfer these metrics to base station 300 along with or instead of the data. In some exemplary embodiments, base station 300 transmits the data to group monitoring device 400, along with or instead of the metrics. In some exemplary embodiments, group monitoring device 400 calculates metrics based on the data.

Figure 4:
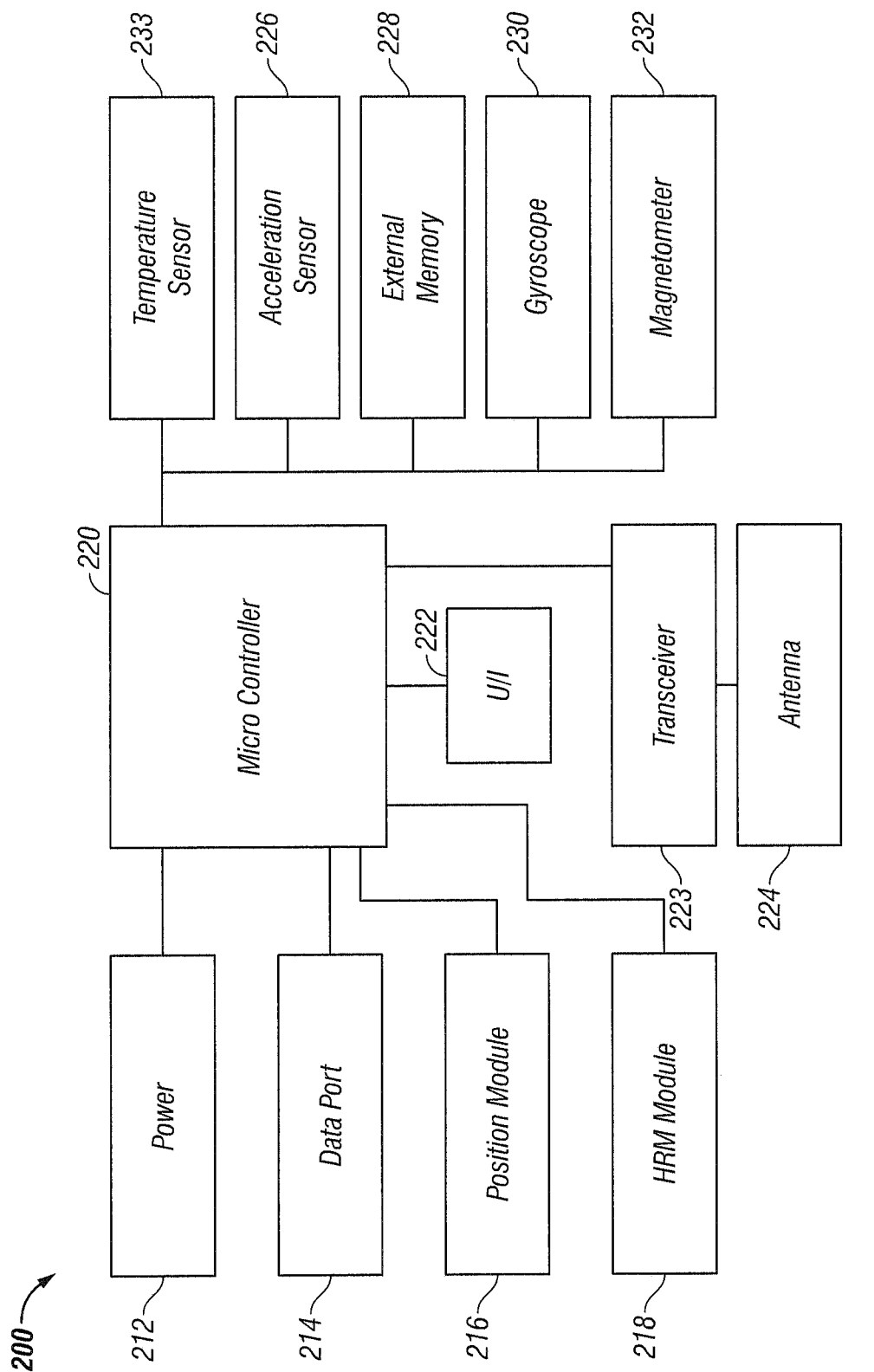
FIG. 4 depicts a diagram of an individual monitor according to an exemplary embodiment of the present invention.

In an exemplary embodiment, as shown in FIG. 4, individual monitor 200 includes a battery 212, a data port 214, a position module 216, a heart rate monitor module 218, a controller 220, a user interface 222, a transceiver 223, an antenna 224, an acceleration sensor module 226, a memory 228, a gyroscope module 230, a magnetometer module 232, and a temperature sensor module 233. The sensors and corresponding modules discussed herein are exemplary only; other sensors and modules can be used in conjunction with embodiments of the present invention. Battery 212 can provide power to individual monitor 200 and may be, for example, built into individual monitor 200 or removable from individual monitor 200, and may be rechargeable or non-rechargeable. Data port 214 can facilitate information transfer to and from individual monitor 200 and may be, for example, a universal serial bus (USB) port. In some exemplary embodiments, data port 214 can additionally or alternatively facilitate power transfer to battery 212, in order to charge battery 212. As will be appreciated, transceiver 223 may include data transmitting and receiving capability and may include a single component or separate components.

Elements of individual monitor 200 may interconnect with one another using a variety of techniques, such as, for example, wires, printed circuit boards, wireless communications technology, serial ports, serial peripheral interfaces, other connection techniques, or a combination thereof. Each individual monitor 200 is portable with respect to base station 300 and can be carried by an individual 10 participating in an athletic activity. Individual monitor 200 may itself include sensors 202, and/or may be in communication with sensors 202 carried by individual 10 and located remotely from individual monitor 200. Each individual monitor 200 can be paired with base station 300 and associated with an individual 10. Each individual monitor 200 may include a unique identifier. The unique identifier may be, for example, a number imprinted on a viewable surface of individual monitor 200, or data communicated or displayed when a button is pressed on individual monitor 200 or when a request signal is received from base station 300.

Figure 23:
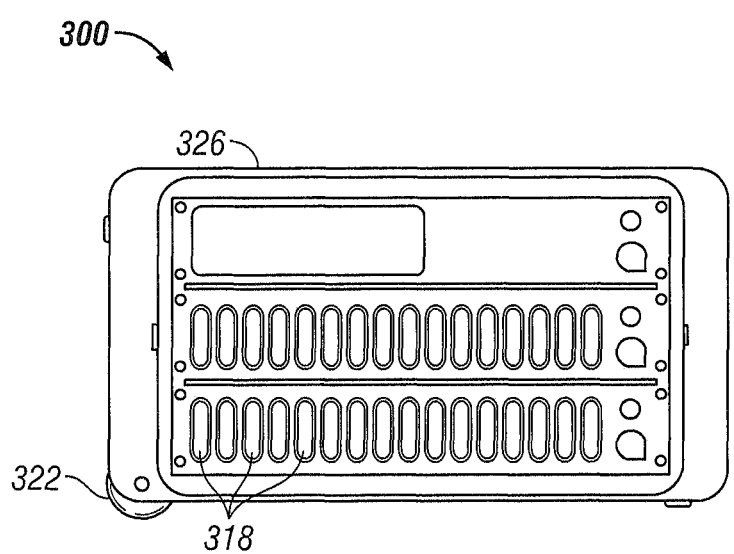
FIG. 23 depicts a base station according to an exemplary embodiment of the present invention.
Figure 24:
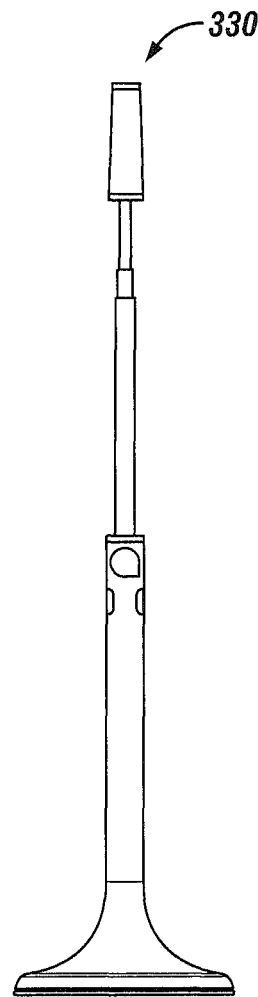
FIG. 24 depicts an antenna of a base station according to an exemplary embodiment of the present invention.
Figure 25:
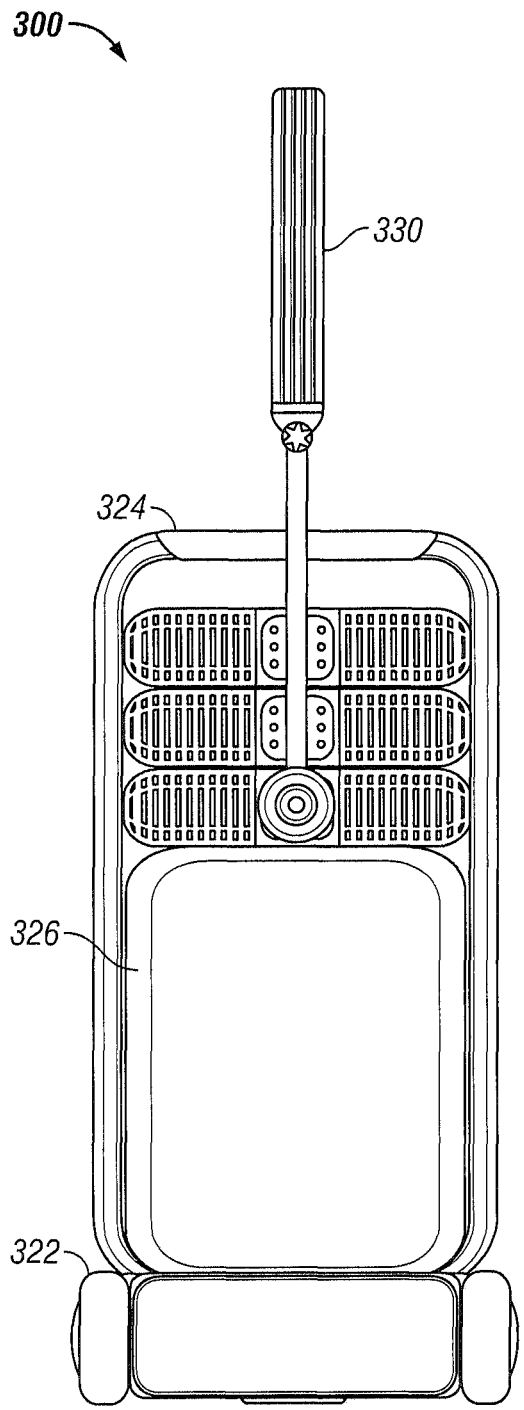
FIG. 25 depicts a base station according to an exemplary embodiment of the present invention.
Figure 26:
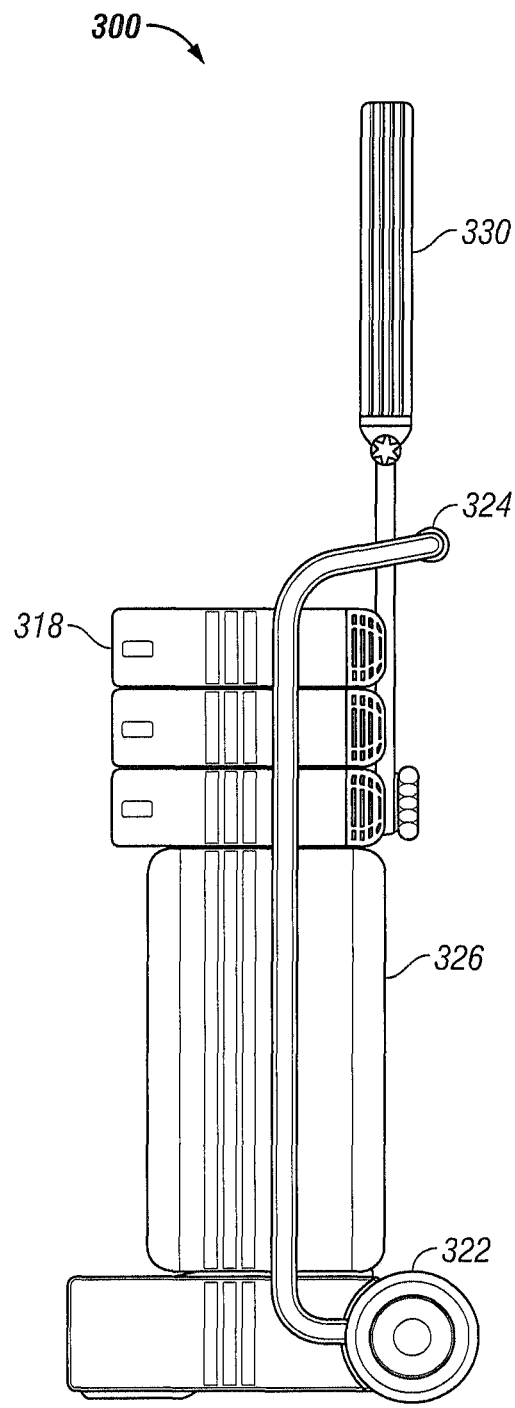
FIG. 26 depicts a base station according to an exemplary embodiment of the present invention.

To be paired with base station 300, individual monitor 200 can be received by a docking port 318 of base station 300 (see, e.g., FIG. 23). Base station 300 can then record the individual monitor 200 unique identifier and can assign a unique encryption key to individual monitor 200. This encryption key can be used to support secure transmission of data during the session of athletic activity. Such secure transmission of data may be, for example, from individual monitors 200 to base station 300, from base station 300 to individual monitors 200, and from one individual monitor 200 to one or more other individual monitors 200. The encryption key can be renewed when required or desired (e.g., at the beginning of each new session of athletic activity).

Figure 53:
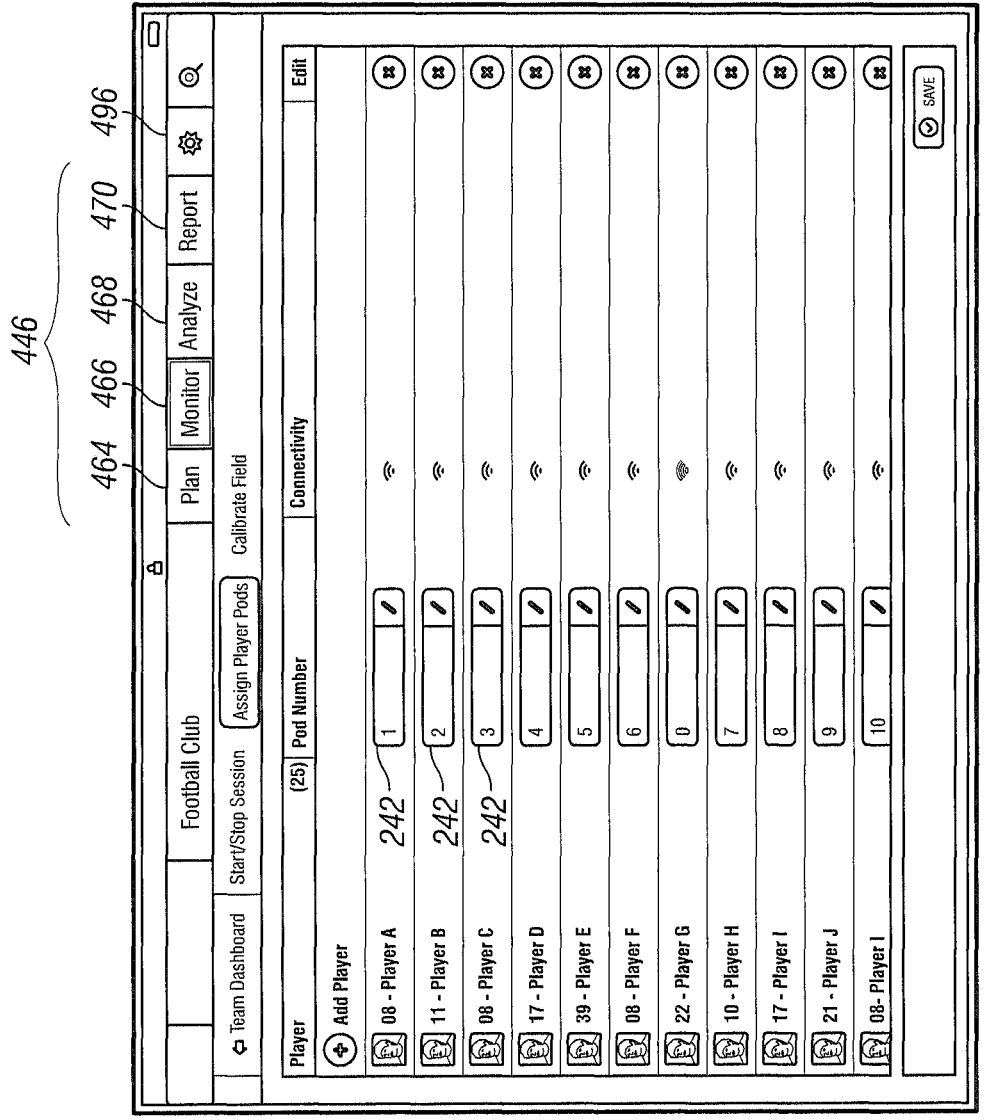
FIG. 53 depicts a display of a group monitoring device according to an exemplary embodiment of the present invention.

In some exemplary embodiments, assigning of individual monitors 200 to individuals 10 can be facilitated by use of group monitor device 400, as depicted in, for example, FIG. 53. For example, display 402 of group monitor device 400 may display a team or other group of individuals 10, along with monitor identifying information 242 (indicative of the unique identifier of an individual monitor 200) of individual monitors 200 associated with individuals 10. A user of group monitor device 400 may change this association by selecting the identifying information 242 of a particular individual monitor 200 associated with an individual 10, and inputting identifying information 242 of a different individual monitor 200 to be associated with the individual 10. Display 402 may also display an indication of the connectivity or signal strength between individual monitors 200 and base station 300.

Via an administrative interface 320 of base station 300, (which may be, e.g., an input and display located on base station 300, or which may be incorporated into a remote device such as, e.g., group monitoring device 400 or analysis device 600) identification information of individual 10 (e.g., individual 10's name and/or jersey number) can be associated with the unique identifier of the individual monitor 200 to be carried by individual 10. Once properly paired with base station 300 and associated with individual 10, individual monitor 200 can be removed from docking port 318 and mounted on individual 10. Any external sensors 202 can be mounted on individual 10 and connected to individual monitor 200.

In an exemplary embodiment, such as that depicted in FIGS. 4-7, individual monitor 200 is a pod-like device and includes a position module 216 for determining data indicative of the location of individual monitor 200 (and thus the location of individual 10 carrying individual monitor 200), a heart rate monitor module 218 for determining data indicative of the heart rate of individual 10, a three-axis acceleration sensor module 226 for determining data indicative of the acceleration of individual 10, a gyroscope module 230 for determining data indicative of the orientation of individual 10 with respect to, for example, a playing field and/or base station 300, and a magnetometer module 232 for calibrating body motion data determined by gyroscope module 230 and acceleration sensor module 226. Each of position module 216, heart rate monitor module 218, acceleration sensor module 226, gyroscope module 230, and magnetometer module 232 may themselves include associated sensors (e.g., a GPS sensor, a heart rate sensor, an acceleration sensor, a gyroscope, and a magnetometer, respectively), or may be in communication with such an associated sensor. Such communication may be wired or wireless. In the case of wireless communication, each module may be communicatively paired with an associated sensor, to avoid miscommunication and interference due to communication of other components. In some exemplary embodiments, some or all of these and other modules may be included in a single module.

In an exemplary embodiment, some or all of sensors 202 are incorporated into sensor garment 204. In such an embodiment, sensors 202 incorporated into sensor garment 204 may connect to individual monitor 200 via wires also incorporated into sensor garment 204.

During participation by individual 10 in the session of athletic activity, sensors 202 sense various characteristics of individual 10, generate data indicative of those characteristics, and transmit that data to memory 228 of individual monitor 200, where it is stored. Contemporaneously, individual monitor 200 wirelessly transmits the data to base station 300. The resolution at which the data is stored in memory 228 and at which the data is transmitted to base station 300 may be different, in order to optimize bandwidth, to optimize battery life, or for any other reason. For example, the heart rate of individual 10 may be sampled by heart rate monitor module 218 at 200 Hz, and data indicative of the heart rate may be generated at 200 Hz and stored in memory 228 at 200 Hz, but may be transmitted wirelessly to base station 300 at 2 Hz during the athletic activity. In some embodiments memory 228 is sufficient to store data from a single session of athletic activity (e.g., 3 hours of data collection), and in some embodiments memory 228 is sufficient to store data from up to 5 sessions of athletic activity (e.g., up to hours of data collection).

Acceleration sensor module 226 can determine data indicative of acceleration, which can be used in calculating, for example, speed, distance, and metrics that will be discussed below. In some exemplary embodiments, the data indicative of acceleration can be used to increase accuracy of position data by, for example, using an accelerometer as a step counter or to determine a filter for a GPS signal calculation. In some exemplary embodiments, the data indicative of acceleration can be used, in conjunction with pattern recognition software, to determine the activity (e.g., the sport, movement, and/or drill) that an individual 10 is performing.

Additionally, acceleration sensor module 226 can be used in conjunction with magnetometer module 232 and gyroscope module 230 in order to calibrate body motion determinations. For example, information indicative of impact, change in motion, gravity, and step counting can be obtained using acceleration sensor module 226. Angular movement can be obtained using gyroscope module 230, and the absolute "North" orientation can be obtained using magnetometer module 232. These sensor readings can be used to determine, for example, the posture of an individual 10, gravity, orientation of individual 10 in space, and heading of individual 10.

Position module 216 may determine data indicative of absolute position at, for example, 10 Hz. Acceleration sensor module 226 may determine data indicative of acceleration at, for example, 200 Hz. Gyroscope module 230 may determine data indicative of change of position and orientation at, for example, 200 Hz. Magnetometer module 232 may determine data indicative of orientation at, for example, 200 Hz. Data may be transmitted from individual monitor 200 (via antenna 224) to base station 300 using a radio frequency (RF) link. The RF link between individual monitor 200 and base station 300 should be sufficiently robust to cover the expected area of the athletic activity (e.g., playing field 30). In some exemplary embodiments, the RF link is sufficient to cover a distance of 50-300 meters under all operating conditions. In some exemplary embodiments, the RF link uses a globally available, license-free band (e.g., the 2.4 GHz frequency). In some exemplary embodiments, the RF link is configurable to cover multiple license-free bands used throughout the world. As will be described in greater detail below, in some exemplary embodiments base station 300 is capable of using the RF link to link to a plurality of individual monitors simultaneously, for example, up to 25 individual monitors 200, or up to 30 individual monitors 200.

Figures 5, 6:
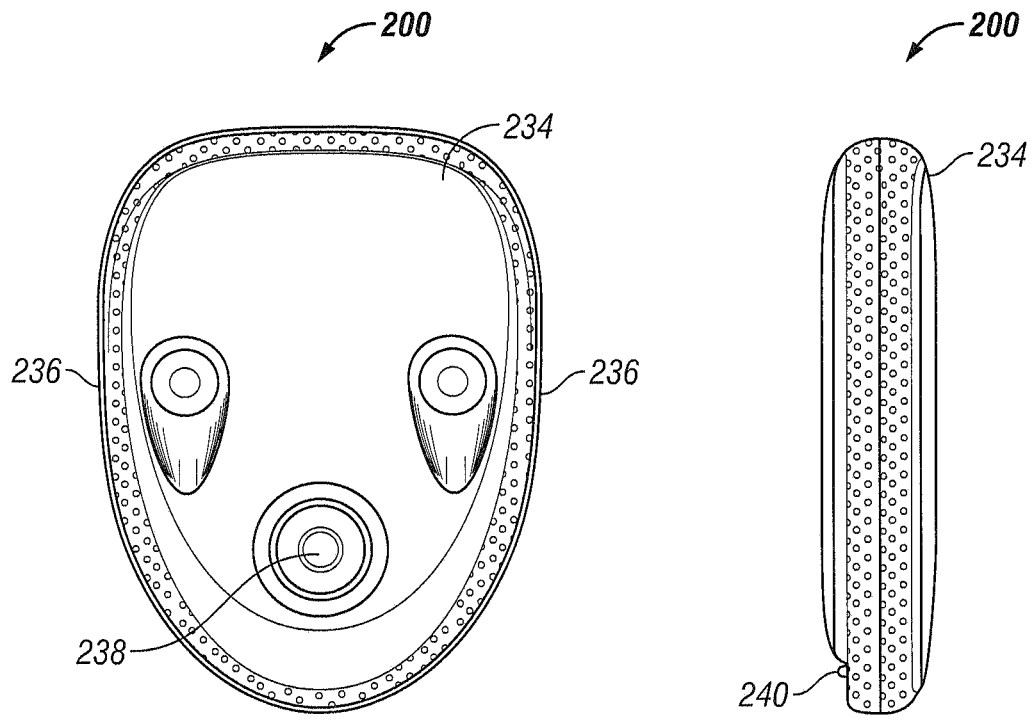
FIG. 5 depicts an individual monitor according to an exemplary embodiment of the present invention.
FIG. 6 depicts an individual monitor according to an exemplary embodiment of the present invention.
Figure 7:
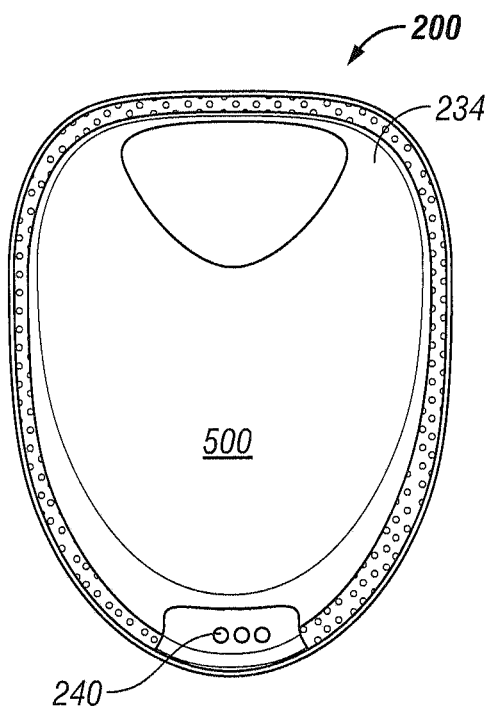
FIG. 7 depicts an individual monitor according to an exemplary embodiment of the present invention.

Individual monitor 200 may be, for example, a pod-like device, as shown in FIGS. 5-7, including a plastic housing 234 that contains components of individual monitor 200, such as the modules discussed above, for example. Individual monitor 200 may include connectors 236 that can provide connection to conductors to removably connect individual monitor 200 to, for example, sensors 202. Connectors 236 may removably connect to sensors 202 via, for example, snaps, clips, latches, or any other suitable technique. Individual monitor 200 may further include an input 238, which may be a button and which may function to turn individual monitor 200 on or off, when appropriately manipulated. Input 238 may include a background light indicator, which may be, for example, one or more light emitting diodes (LEDs) that indicate qualities of individual monitor 200. Such qualities may include, for example, state of operation (e.g., on, off, active, inactive, charging, low battery), memory status, and battery status. In some exemplary embodiments, individual monitor 200 includes a visual display, such as, for example, a liquid crystal display (LCD) screen, that can display this and other information.

Individual monitor 200 may further include a docking port 240, which facilitates wired communication with base station 300, and which can facilitate charging of battery 212 of individual monitor 200, when individual monitor 200 is docked with base station 300. Housing 234 of individual monitor 200 may be sized so as to accommodate components of individual monitor 200 while minimally interfering with individual 10's performance of the athletic activity. Housing 234 may be sized, for example, to fit into a pocket or cavity of a garment (e.g., sensor garment 204). In some exemplary embodiments, dimensions of housing 234 do not exceed 70 mm by 55 mm by 11 mm.

In some exemplary embodiments, housing 234 is water resistant, and all openings (e.g., docking port 240, connectors 236) are sealed while in use during athletic activity. Such water resistance can be achieved by a close fit between exposed parts of individual monitor 200 (particularly housing 234), by use of plugs (e.g., plastic or rubber) that fit into openings, by use of a water resistant sealing compound, by other techniques, or by any combination thereof.

Individual monitor 200 may include data processing capabilities, such as raw data reduction and filtering. For example, controller 220 may be configured to receive raw data from sensors 202 and to process such data at the individual monitor, prior to transmission to base station 300. For example, rather than transmitting raw data representing electrical activity sensed by heart rate monitor sensor 206, controller 220 of individual monitor 200 may process the raw data to calculate heart rate, number of heart beats in a given period, or other metrics of interest, which can be transmitted to base station 300. In some exemplary embodiments, controller 220 of individual monitor 200 may use a unique encryption key (assigned by data processing module 304 of base station 300) to encrypt data in order to securely transmit such data to base station 300. Such processing of data at individual monitor 200 is not necessary, however, and raw data can be transmitted directly to base station 300 without such processing.

Operation of individual monitor 200 may be controlled by software stored in individual monitor 200 (e.g., stored in memory 228). This software can be updated when necessary or appropriate. Software can be updated via communication with base station 300, which may send software updates to individual monitor 200 wirelessly. Alternatively or additionally, software of individual monitor 200 may be updated through direct connection with base station 300 via docking ports 318 (as will be described below), such that firmware of individual monitor 200 may be flashed appropriately.

Sensors 202 are selected and configured to provide a basis for determination of metrics of the individual 10 with which they are associated. As used herein, "metrics" may refer to representations of characteristics relevant to individual 10 or one or more groups of individuals 10, and may be, for example, physiological-, performance-, or location-based. A "metric" may simply be a representation of a characteristic sensed by one of sensors 202, or may be a representation of a quality derived from data indicative of characteristics measured by one of sensors 202. For example, an acceleration sensor 210 senses acceleration, and provides data indicative of this characteristic. This data can be represented as a metric. Additionally, this data can be further processed to determine further metrics such as velocity, direction of acceleration, and distance. Processing involving formulas and algorithms that work on the data received from sensors 202 (including data from different sensors 202) and other sources can be used to determine a wide variety of metrics determined to be useful to trainer 20, including custom-designed metrics. Metrics can provide useful information individually about multiple individuals and can provide useful information about groups of individuals 10. Metrics can also take into account attributes of a particular individual 10 or group of individuals 10, such as, for example, height, weight, endurance, and top speed.

Base station 300 may be a self-contained portable system, such as the exemplary embodiments depicted in FIGS. 21-26, containing all hardware required or desired to perform the functions of base station 300 described herein. In some exemplary embodiments, base station 300 weighs no more than 25 kilograms. In some exemplary embodiments, base station 300 is sized so as to fit easily into the trunk of a car or the overhead storage area of a passenger aircraft. In some exemplary embodiments, base station 300 includes a pair of wheels 322 at one end, and a handle 324 at the other end, to facilitate mobility of base station 300. In some exemplary embodiments, base station 300 is waterproof, and can withstand impacts associated with regular use and transport. In some exemplary embodiments, base station 300 is contained within a hard shell-style case 326. In some exemplary embodiments, base station 300 is contained within a soft duffel bag-style case 328.

In some exemplary embodiments base station 300 is configured to be portable. In some exemplary embodiments, base station 300 is configured to be positioned at an activity site. In some exemplary embodiments base station 300 is configured to be movable between activity sites such that it can be positioned at various activity sites. In some exemplary embodiments base station 300 is configured to be portable with respect to at least one of individual monitors 200 and group monitoring device 400. In some exemplary embodiments base station 300 is configured to be portable with respect to both individual monitors 200 and group monitoring device 400.

In some exemplary embodiments, base station 300 itself includes sensors, such as, for example, a GPS sensor (or other position sensor), a gyroscope, a magnetometer, a temperature sensor, a humidity sensor, and/or a wind sensor. Such sensors can provide valuable data that can be used in algorithms to determine metrics associated with individuals 10, as will be described below.

In some exemplary embodiments, base station 300 includes a reference sensor 334 (e.g., a GPS reference sensor), which may be physically included within base station 300 or independent of and located remote from base station 300 at a known position with respect thereto. Reference sensor 334 can be connected to base station 300 via wires or wirelessly. Reference sensor 334 can be used to detect a deviation signal and use it to calculate a correction signal for received position signals (e.g., GPS data). This correction signal can be sent to individual monitors 200 (e.g., via base station 300). This correction signal can be used to correct position determinations of individual monitors 200, thereby increasing their accuracy. Determining such a correction signal and then sending it to individual monitors 200 achieves efficient use of processing capacity, because individual monitors 200 are not burdened with determining a correction signal themselves, but simply receive and use a correction signal determined at base station 300 or reference sensor 334.

Figure 8:
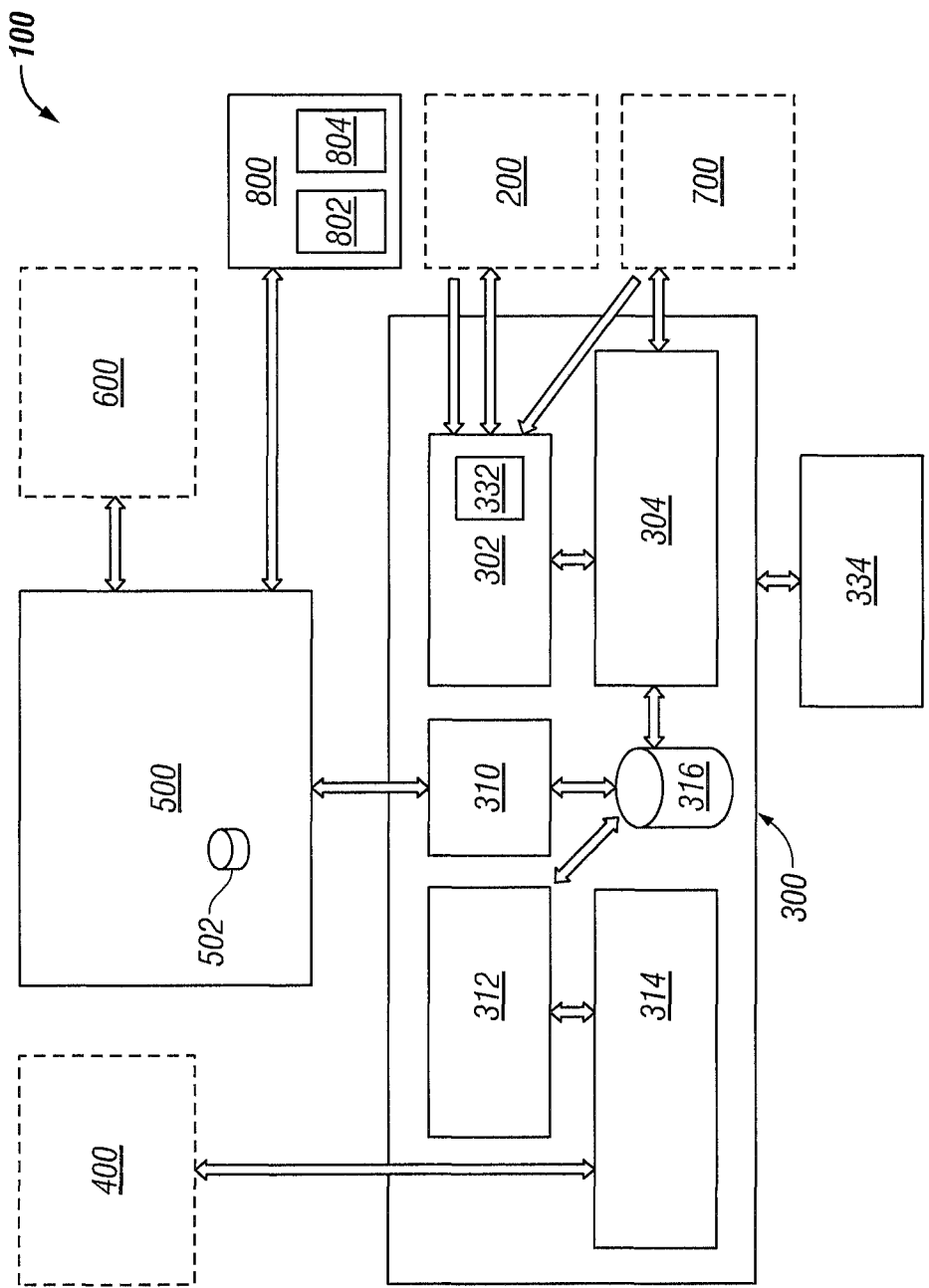
FIG. 8 depicts a diagram of a monitoring system according to an exemplary embodiment of the present invention.

Base station 300 may transmit and receive data from individual monitors 200 via an antenna 330 configured for one or more of RF communication, WLAN communication, ISM communication, cellular (e.g., GSM broad band 2.5G or 3G) communication, other suitable communication, or a combination thereof. Communication between base station 300 and individual monitors 200 may be bi-directional or uni-directional. Antenna 330 may be a high-gain antenna, and in some exemplary embodiments base station 300 includes multiple (e.g., 2) such antennas 330. In some exemplary embodiments, base station 300 includes an antenna configured to send and/or receive a positioning signal such as that of a satellite-based positioning system (e.g., GPS). Base station 300 can then determine metrics from the received data. FIG. 8 depicts a diagram of an exemplary embodiment of monitoring system 100. As shown in FIG. 8, base station 300 includes a data reception module 302, a data processing module 304, a central synchronization (sync) module 310, a logic module 312, a web server module 314, and a base station database 316.

As described above, base station 300 receives data from individual monitors 200. Data reception module 302 of base station 300 may be in communication with each active individual monitor 200. In some exemplary embodiments data reception module 302 receives data from individual monitors 200 via antenna 330 in communication with individual monitors 200 through the RF link described above. Data reception module 302 writes the received data to a data file, which may be, for example, a comma-separated values file or a tab delimited file. The file may be, for example, a single file used to write the data to, or a rolling file (file roll) based on, for example, time, number of entries, or size. The data file may be updated using any suitable interval and parameters. For example, 30 individual monitors 200 may be active and updating 5 data points at 2 Hz, in order to update the data file in near real time.

Data reception module 302 may perform a data integrity check on the received data. In some exemplary embodiments data reception module 302 decrypts the received data. In some exemplary embodiments data reception module 302 is agnostic to the received data, and does not decrypt the received data. In some exemplary embodiments data reception module 302 buffers content as needed.

Data reception module 302 may include a data read module 332 that reads the data from the data file and transmits it to data processing module 304. Data read module 332 may run at any suitable interval, such as, for example, 500 ms, to read the change in the data written to the data file.

Prior to individual monitors 200 being used by individuals 10 during a session of athletic activity, each individual monitor 200 is connected to base station 300 (e.g., by docking in docking port 318, or wirelessly) and is assigned an encryption key by data processing module 304. Individual monitors 200 can use this encryption key to securely transmit data to data reception module 304. Data processing module 304 receives data from data reception module 302, as described above, and de-crypts the data, if encrypted, by using the unique encryption key assigned to a particular individual monitor 200. Data processing module 304 transmits the decrypted data to base station database 316, for storage.

Base station database 316 is preferably configured for short term storage of data generated during sessions of athletic activity, while long term storage is accomplished by web server system 500, as will be discussed in greater detail below. Base station database 316 may include sufficient storage space for at least all data expected to be generated in 1 session of the athletic activity. In some exemplary embodiments, base station database 316 includes sufficient storage space for at least all data expected to be generated in 3 sessions of the athletic activity (e.g., greater than approximately 2 gigabytes). In some exemplary embodiments, base station database 316 is configured for long term storage, and includes sufficient storage space, for example, for at least all data expected to be generated in 10 years of use monitoring athletic activities (e.g., greater than approximately 600 gigabytes).

Logic module 312 polls base station database 316 and applies algorithms to the polled data to determine metrics and alerts. Logic module 312 can determine a wide variety of metrics, including custom-designed metrics, by application of appropriate algorithms. Logic module 312 can transmit such metrics to web server module 314. More detailed description of exemplary metrics and their use will be provided below.

In some exemplary embodiments, trainers 20 can create alerts for individuals 10 in order to inform trainer 20 of the occurrence of events. Such alerts can be used to, for example, measure workout effectiveness, manage training load, identify achievement of training targets, or identify dangerous situations. Alerts can be based on a number of metrics, such as, for example, distance (total and/or time within particular speed ranges), heart rate (present and/or cumulative time within particular heart rate zones, heart rate moving outside particular heart rate zones), and power or training load. Such alerts can be generally applied to all individuals 10 (individually or in groups), or can be tailored to be specific to a particular individual 10. Such alerts can be generally applied to all sessions of athletic activity, or can be tailored to be specific to a particular session of athletic activity.

Trainers 20 can create such alerts via an administrative device, which may be a device such as, for example, group monitoring device 400 or analysis device 600, described in greater detail below. In some exemplary embodiments, alerts can be created using a remote computer (e.g., by a team manager or medical support person) and can be transferred to the base station and to any of individual monitors 200, group monitoring devices 400, or analysis devices 600 (e.g., via the Internet, and/or any of the communications channels described herein). Trainers can create an alert by, for example, selecting a metric, selecting conditions (e.g., target metric value, time frame for maintaining target metric value, date range for achieving target, target metric range), specifying exceptions, assigning the alert to an individual 10 (or a group of individuals 10), and associating the alert with a session of athletic activity.

Figure 16:
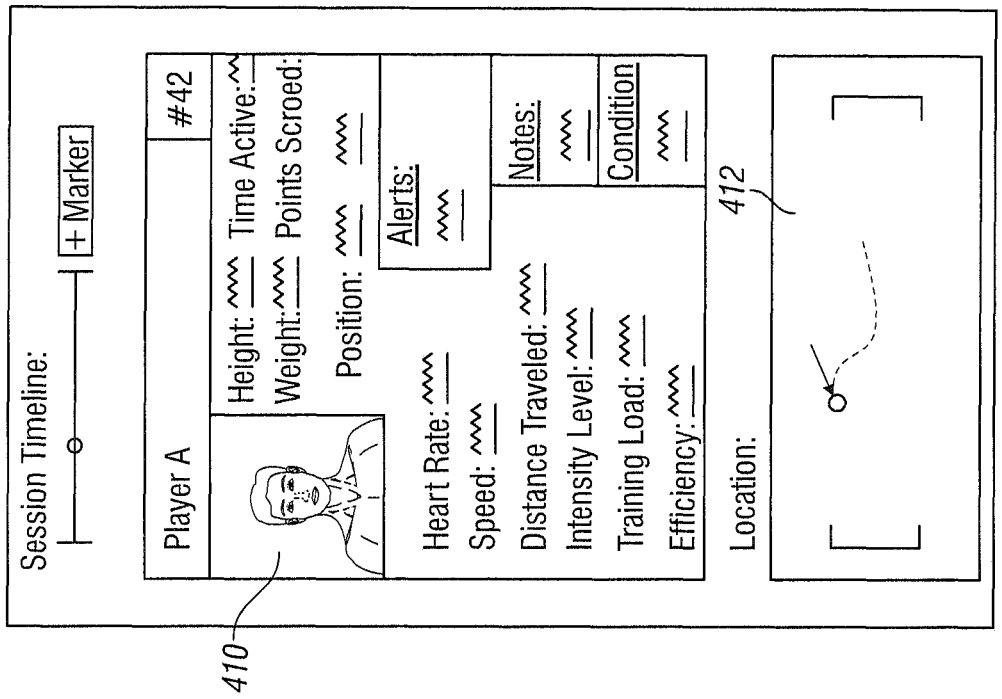
FIG. 16 depicts a display of a group monitoring device according to an exemplary embodiment of the present invention.
Figures 19, 20:
FIG. 19 depicts a display of a group monitoring device according to an exemplary embodiment of the present invention.
FIG. 20 depicts a display of a group monitoring device according to an exemplary embodiment of the present invention.
Figure 21:
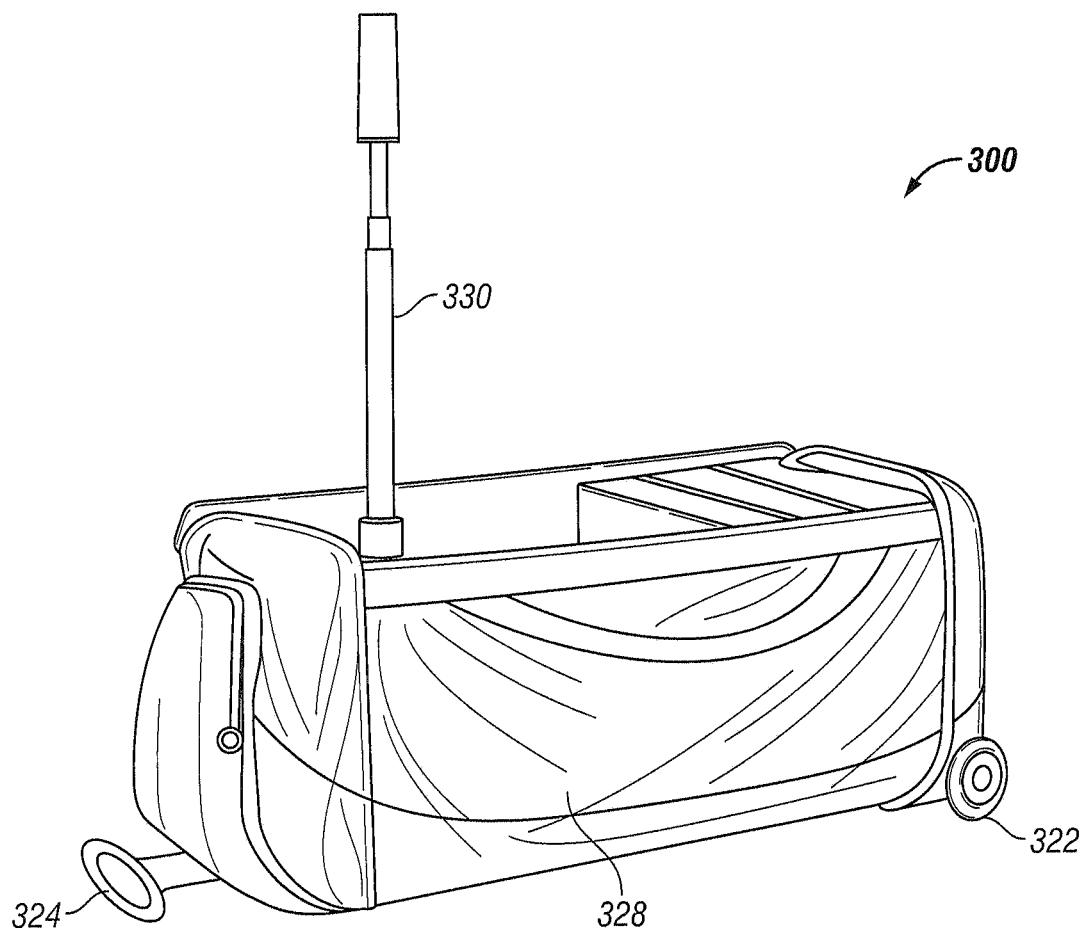
FIG. 21 depicts a base station according to an exemplary embodiment of the present invention.
Figure 22:
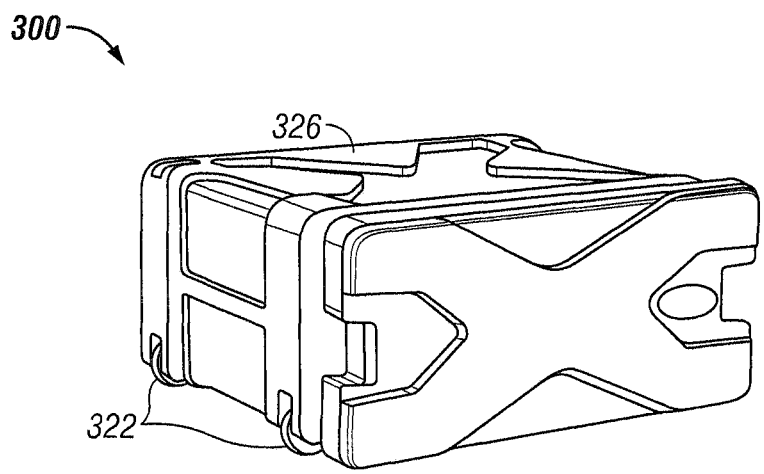
FIG. 22 depicts a base station according to an exemplary embodiment of the present invention.

The created alert may be viewed in association with its associated individual 10 when viewing a dashboard (such as that displayed by group monitoring device 400 or analysis device 600, see FIGS. 16 and 20) of associated individual 10. Progress of individual 10 toward triggering an alert (triggering occurs when the conditions of the alert are met) can be monitored during a session of athletic activity via group monitoring device 400. Past alerts that have been triggered can be stored in association with individual 10 or a group of individuals 10, and these alert histories may be viewed using, for example, group monitoring device 400 or analysis device 600. Examples of potential alerts include exhibiting an irregular heart rate, exhibiting a body temperature above 38 degrees C. (potentially a sign of hyperthermia), maintaining a heart rate of 85% of maximum or higher for 10 minutes or more, traveling a distance of 900 meters at a speed of 6.0 meters per second or more, achieving a training load of 700 Watt or more.

Logic module 312 can transmit information about such alerts (including, e.g., information indicating progress toward triggering an alert and information indicating an alert is triggered) to group monitoring device 400 (via web server module 314 of base station 300) during athletic activity of individual 10. The information about such alerts can be stored in base station database 316.

Web server module 314 can receive metric and alert information from logic module 312 for individual 10, or for multiple individuals 10 (including groups of individuals 10). Web server module 314 can render display code (such as, for example, html5 (hypertext markup language 5) compliant code) based on a request from a client device such as, for example, group monitoring device 400. In some embodiments, web server module 314 uses JavaScript® to open and maintain a web socket. Web server module 314 can also serve a security function, by ensuring that a requesting client device is properly authenticated and that all data is passed using https (hypertext transfer protocol secure). Web server module 314 may provide group monitoring device 400 with requested metrics and generated alerts during the athletic activity, via, for example, an API layer.

Group monitoring device 400 can wirelessly receive metrics, alerts, and other information (e.g., identification information and attributes of individuals 10, or statistics relevant to individuals 10 or the athletic activity generally) from base station 300. A single group monitoring device 400 may be in communication with base station 300, or multiple group monitoring devices 400 may be in communication with base station 300 simultaneously. Group monitoring devices 400 may be portable with respect to base station 300 and may communicate with base station 300 via, for example, WLAN (wireless local area network), 2.4 GHz ISM (industrial, scientific, and medical) band, Bluetooth® (or Bluetooth® Low Energy (BTLE)), or cellular protocols.

In some exemplary embodiments, group monitoring device 400 includes a module selection element 446 which allows selection of one or more operation modules to be displayed. The operation modules may be selectable using operation module icons. In some exemplary embodiments, selection of a plan module icon 464 may trigger display of a plan module including features designed to be used to plan a session of athletic activity. In some exemplary embodiments, selection of a monitor module icon 466 may trigger display of a monitor module including features designed to be used to monitor a session of athletic activity in real time during the session of athletic activity, as described further herein. In some exemplary embodiments, selection of an analyze module icon 468 may trigger display of an analyze module including features designed to be used to analyze a session of athletic activity in real time during the session of athletic activity, or after completion of the session of athletic activity, as described further herein. In some exemplary embodiments, selection of a report module icon 470 may trigger display of a report module including features designed to be used to develop reports (e.g., printable or displayable summaries of selected information) related to a session of athletic activity.

Figure 9:
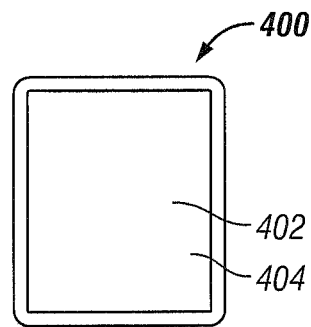
FIG. 9 depicts a group monitoring device according to an exemplary embodiment of the present invention.

In some exemplary embodiments, group monitoring device 400 includes a display 402 and an input 404, as shown, for example, in FIG. 9. In a preferred embodiment, group monitoring device 400 is a tablet computing-style device (such as a tablet personal computer or an iPad, marketed by Apple Inc.®). Group monitoring device 400 may be, however, any other suitable device, such as, for example, a laptop computer, a smartphone, a personal computer, a mobile phone, an e-reader, a PDA (personal digital assistant), a smartphone, or other similar device capable of receiving and displaying information and receiving input.

In some exemplary embodiments, during a session of athletic activity, trainer 20 may use group monitoring device 400 to receive real time information about individuals 10. This information may enable trainer 20 to more easily accomplish a variety of goals. In the case that the athletic activity is a fitness exercise, trainer 20 can leverage real time data received about the fatigue of particular individuals 10 or groups of individuals 10 in order to, for example, inform data-driven real time decisions that optimize the performance of individuals 10 and reduce the potential for injury. For example, trainer 20 may modify a current session of athletic activity (e.g., shorten, extend, pause, end, or change the schedule of activity for the session) based on the information received from group monitoring device 400. Trainer 20 may modify the session for particular individuals 10, or for groups of individuals 10. In the case that a present session of athletic activity has been scheduled using a plan module of monitoring device 400 (as described further herein), the planned schedule can be changed in real time to correspond to decisions of trainer 20. Similarly, in the case that the athletic activity is a competition (e.g., a soccer game), trainer 20 can leverage real time data received about the performance of particular individuals 10 or groups of individuals 10 in order to, for example, inform data-driven real time decisions that optimize the chance for success in the competition. In an exemplary embodiment, group monitoring device 400 can be used to monitor a single individual 10 alone, as well as a group of individuals 10.

In some exemplary embodiments, group monitoring device 400 may be used by broadcasters of an athletic activity in order to, for example, determine and relay to their audience information about individuals 10 participating in the athletic activity.

Figure 14:
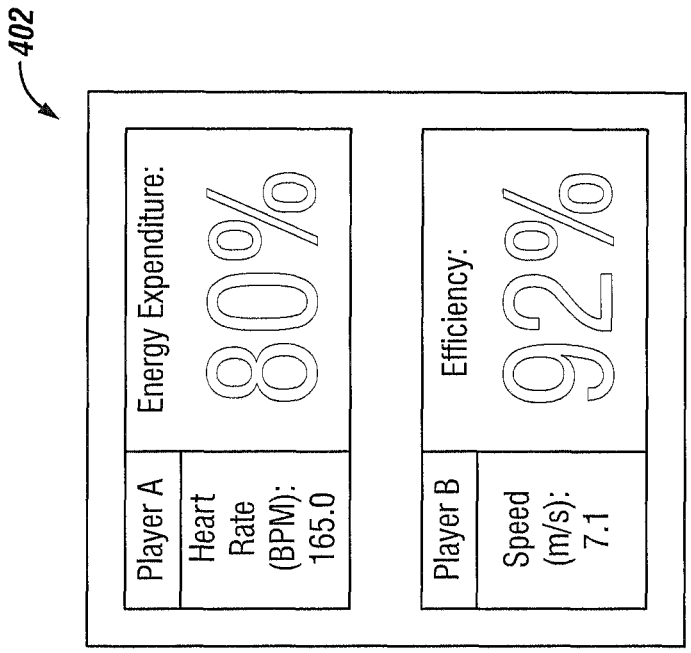
FIG. 14 depicts a display of a group monitoring device according to an exemplary embodiment of the present invention.
Figure 15:
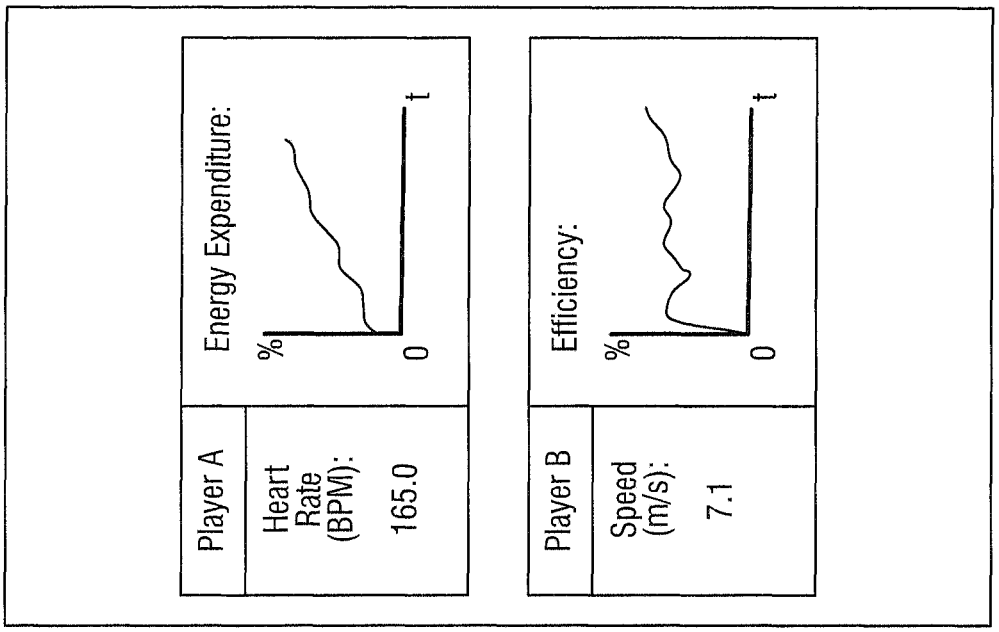
FIG. 15 depicts a display of a group monitoring device according to an exemplary embodiment of the present invention.

Display 402 functions to display representations of individuals 10 (including, for example, identification information, attributes, metrics, and alerts) during participation in a session of athletic activity by individuals 10. The representations can take many forms, including, for example, charts (see FIGS. 13 and 14), dashboards (see FIG. 16), graphs (see FIG. 15), maps (see FIG. 16), colors, symbols, text, images, and icons.

Input 404 is an interface that allows a user, such as trainer 20, to manipulate the representations displayed by display 402. In a preferred embodiment input 404 is a touch-screen input. Input 404 may be, however, any other suitable input, such as, for example, a keyboard, a voice-recognition audio input, or push-button inputs. Input 404 may further include a combination of various types of inputs. Input 404 may be manipulated by trainer 20 to cause display 402 to show desired representations. The representations can update in real time during the athletic activity through the communication of group monitoring device 400 with base station 300, which is in turn in communication with individual monitors 200 worn by individuals 10 participating in the athletic activity, as described above.

In an exemplary embodiment, trainer 20 accesses group monitoring device 400 by inputting unique login credentials via input 404. Alternatively, trainer 20 accesses group monitoring device 400 without inputting login credentials. Upon accessing group monitoring device 400, trainer 20 may manipulate input 404 to use group monitoring device 400 to monitor individuals 10 in real time. Display 402 of group monitoring device 400 can be fully customizable, and different persons using different displays 402 may customize their displays differently. Multiple monitoring devices 400 can be used simultaneously by multiple trainers 20, and each can be customized independently from the others. Each of multiple monitoring devices 400 may monitor different individuals 10 or groups thereof. Each of multiple monitoring devices 400 may monitor present different information and/or the same information in different formats. Each of multiple monitoring devices 400 may be customized to include different alerts and/or markers (as discussed further herein). Such customizability may allow each of a group of trainers 20 to focus on and monitor different aspects of individuals 10 or groups thereof. Each display feature described herein can be modified and/or included in a particular view of display 402 at the option of a user of display 402 (e.g., trainer 20). For ease of description, however, display 402 will be presented herein as representing a variety of different "dashboards", a dashboard being a visual representation of one or more elements. In some exemplary embodiments, dashboards can be defined as default views, which can then be used or modified at the option of the user. For example, a team view dashboard may represent information relating to each individual 10 on a team, as well as information relating to the team as a whole, while an individual view dashboard may represent information relating to a particular individual 10.

Figure 13:
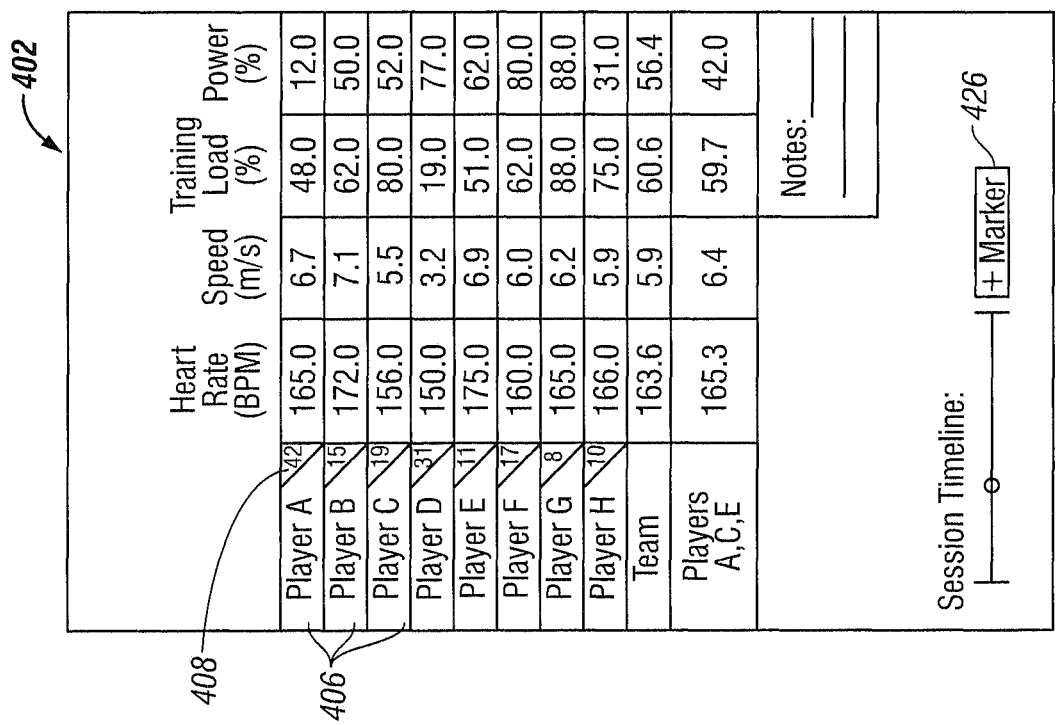
FIG. 13 depicts a display of a group monitoring device according to an exemplary embodiment of the present invention.

In an exemplary embodiment, display 402 of group monitoring device 400 shows a team view dashboard (see, for example, the exemplary display 402 of FIGS. 13, 17, 18, and 27-32, 33A, 33B, 34, and 35A-35D). The team view dashboard may simultaneously display identification information and summary metrics for all individuals presently participating in the monitored athletic activity, or a group thereof. The identification information may include individual name 406 and individual jersey number 408, for example. In some embodiments, a photograph 410 of each individual 10 is also included as identification information (see, e.g., FIGS. 27, 28, 31, 32, and 33A). The summary metrics shown in the team view dashboard can be configured to be the metrics most applicable or most beneficial to trainer 20. In the exemplary display 402 of FIG. 13, present heart rate, speed, training load, and power are shown for each of Player A through Player H (Player A through Player H being individuals 10 presently participating in the monitored athletic activity). The metrics shown in FIG. 13 are shown as numerical values. Display of metrics is not limited to display of numerical values, however. Metrics may be represented in other suitable ways as would be appreciated by one of skill in the art, such as, for example, graphically (see, e.g., FIG. 15), or in map form (see, e.g., FIGS. 16 and 17).

Figure 27:
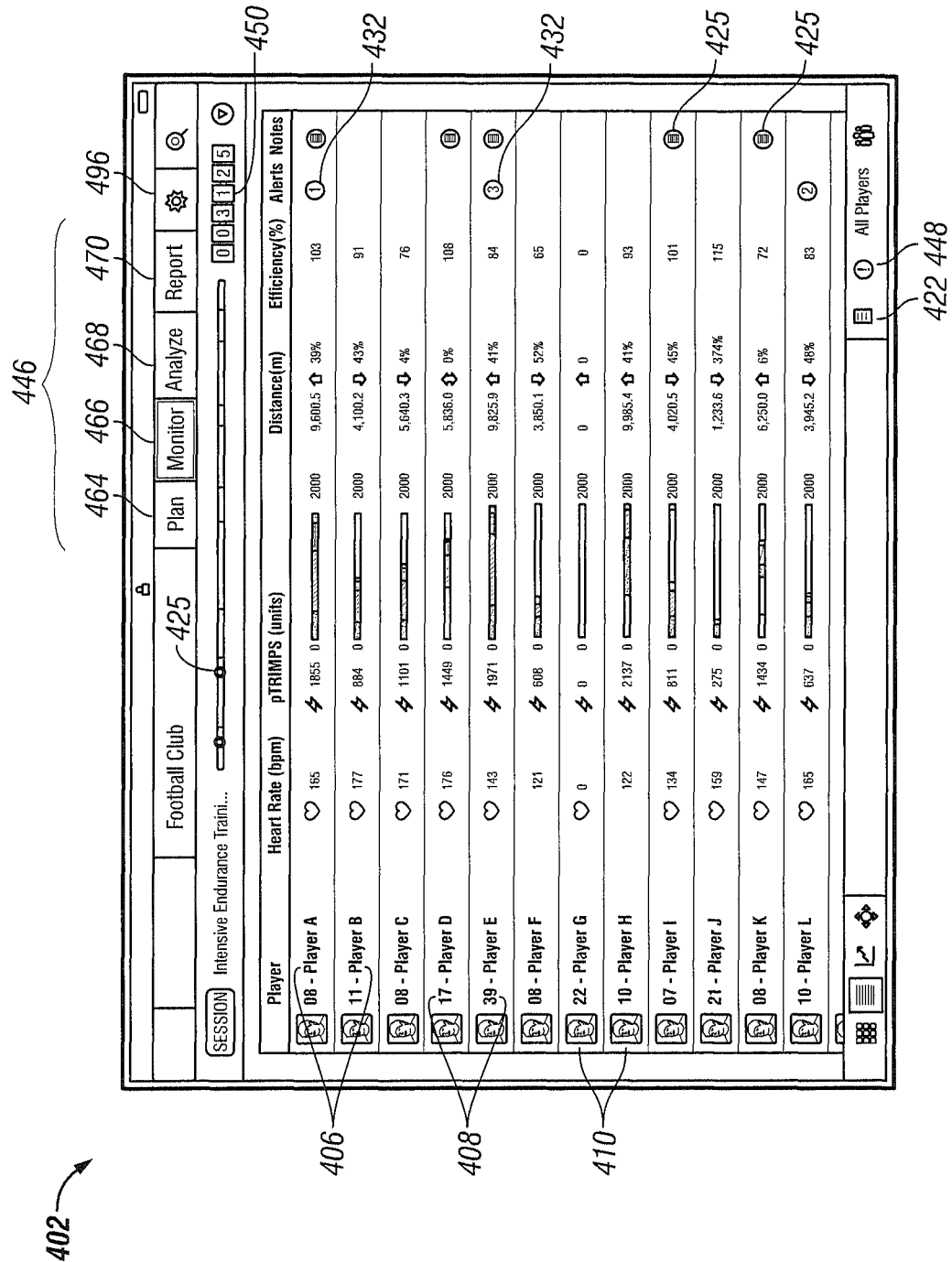
FIG. 27 depicts a display of a group monitoring device according to an exemplary embodiment of the present invention.
Figure 28:
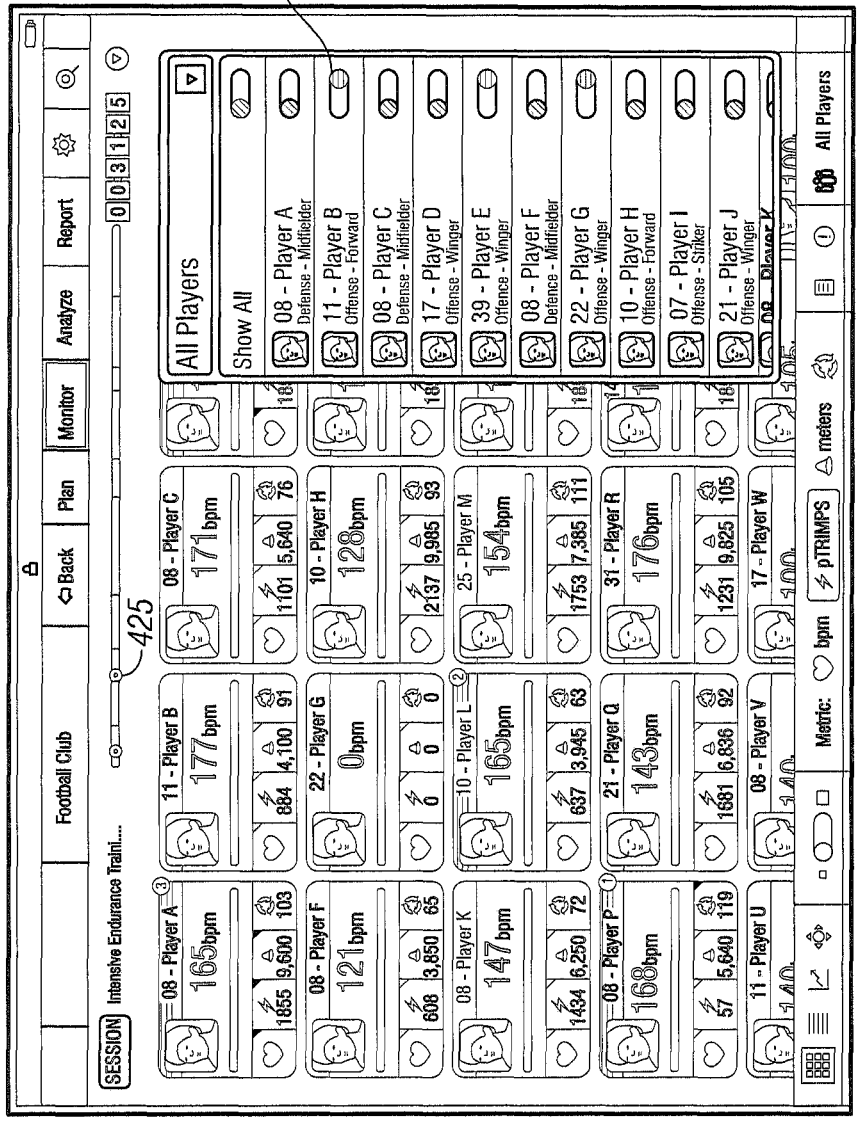
FIG. 28 depicts a display of a group monitoring device according to an exemplary embodiment of the present invention.
Figure 29:
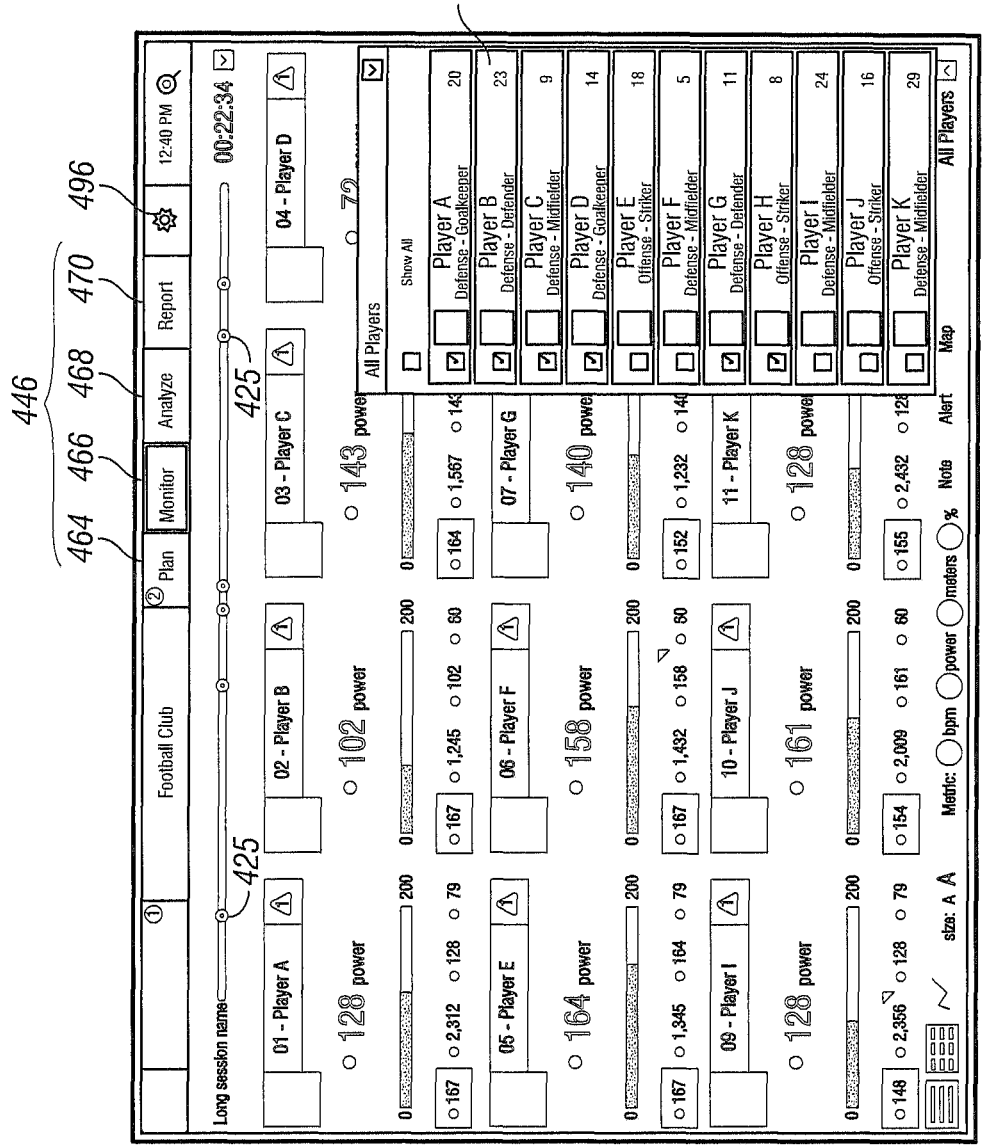
FIG. 29 depicts a display of a group monitoring device according to an exemplary embodiment of the present invention.
Figure 30:
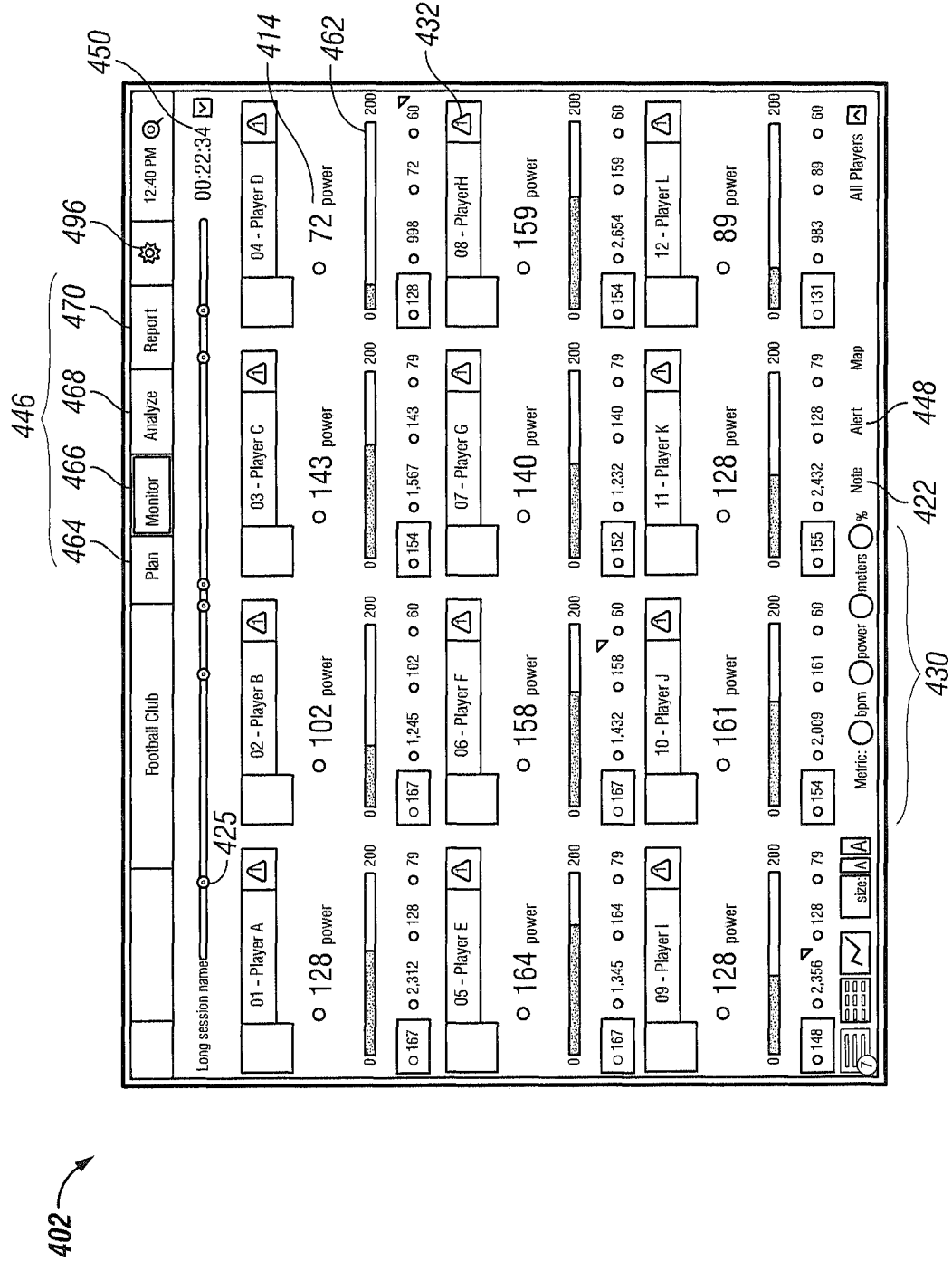
FIG. 30 depicts a display of a group monitoring device according to an exemplary embodiment of the present invention.
Figure 31:
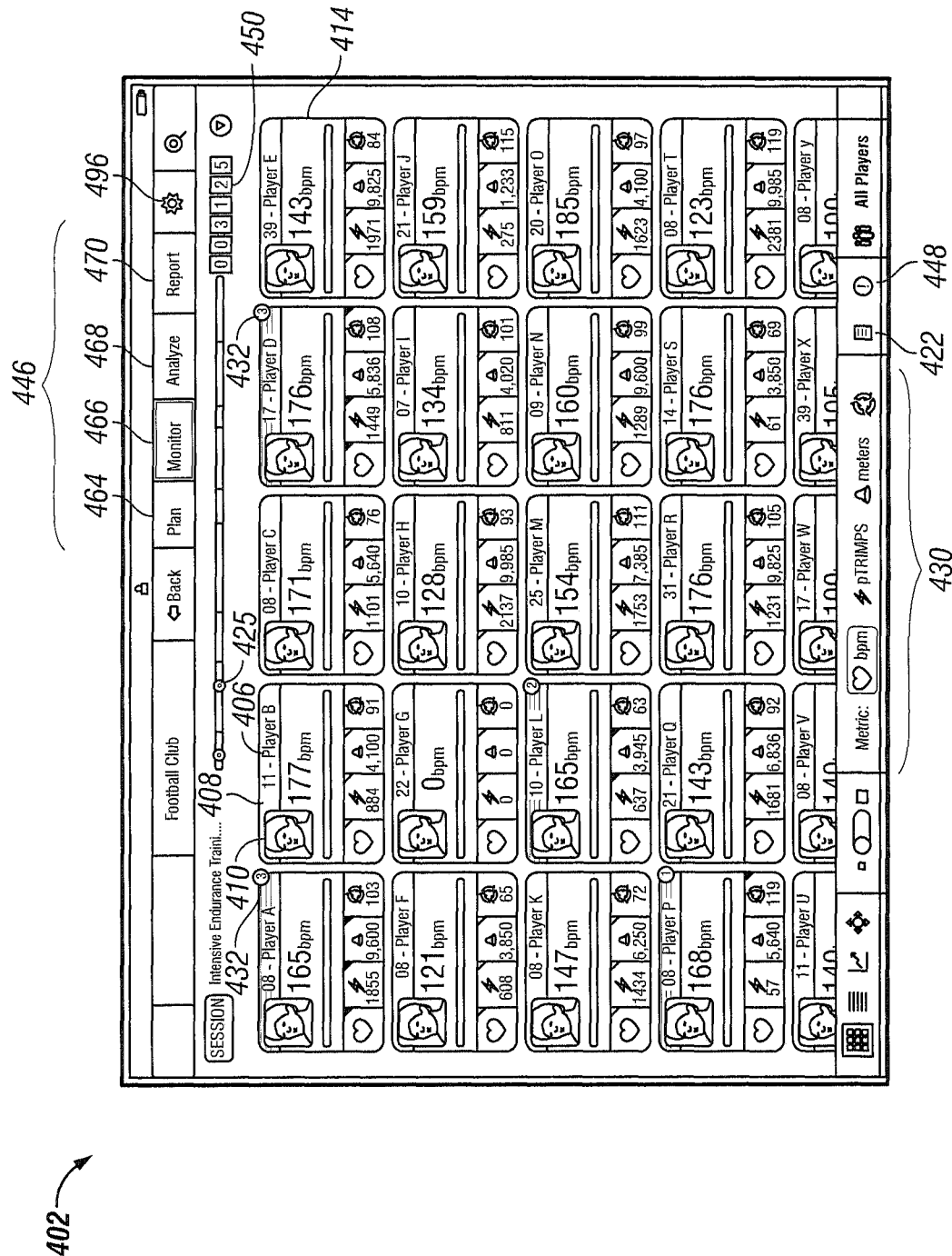
FIG. 31 depicts a display of a group monitoring device according to an exemplary embodiment of the present invention.
Figure 32:
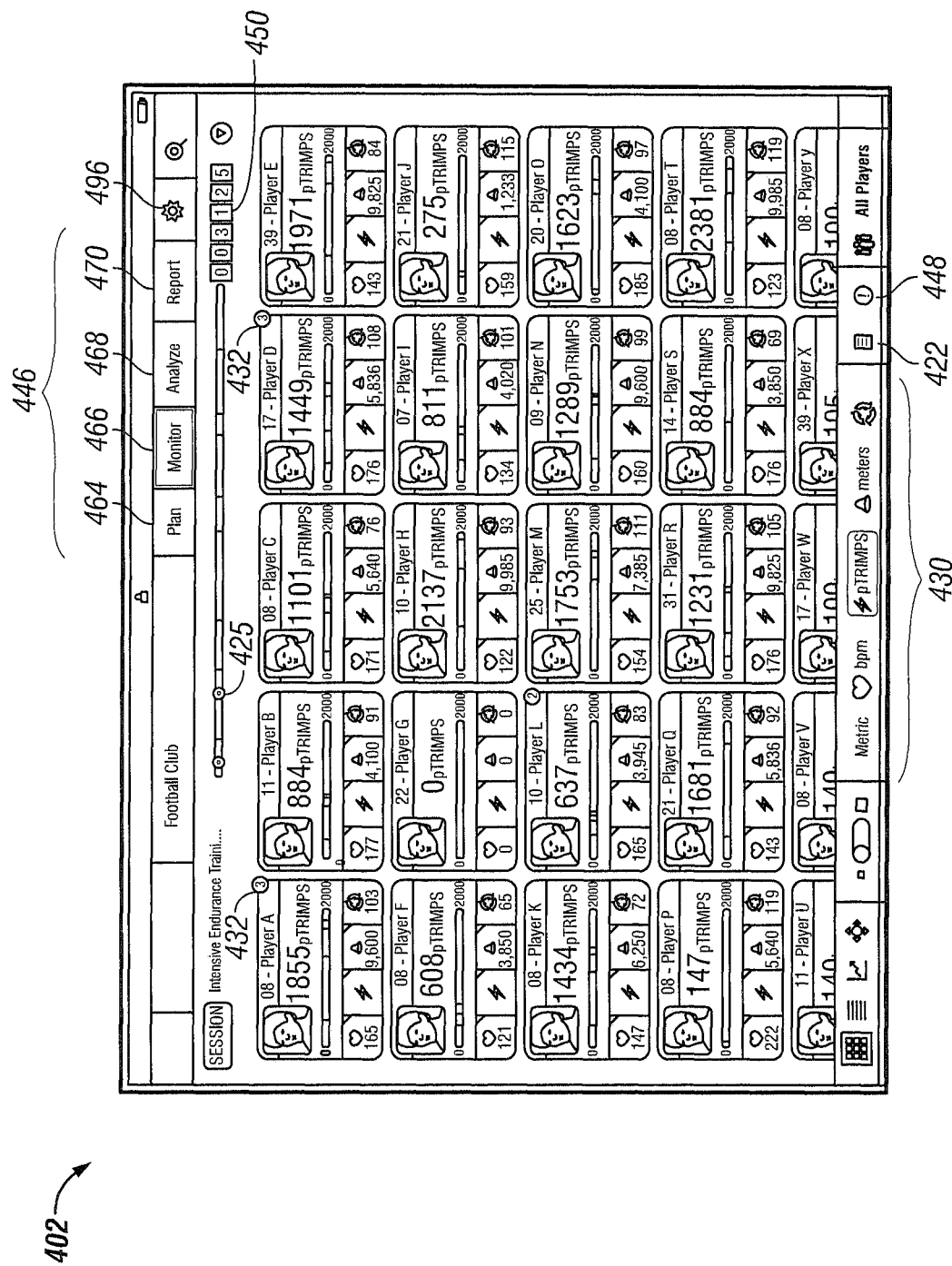
FIG. 32 depicts a display of a group monitoring device according to an exemplary embodiment of the present invention.

In some exemplary embodiments, for example, display 402 of FIG. 27, heart rate, power, distance, and efficiency are shown for each of Player A through Player L, with these values for additional players available to be viewed by scrolling down past Player L. Also shown for each of Player A through Player L are fields for alerts and notes. In some exemplary embodiments, as depicted in, for example, FIGS. 27 and 31, note icons 425 and alert icons 432 may indicate the presence of notes or alerts. Selection of such note icons 425 and alert icons 432 may trigger display of additional information related to an associated note or icon. For example, the team view dashboard of FIG. 27 indicates that player A has 1 alert, Player E has 3 alerts, and Player L has 2 alerts, and that each of Players A, D, E, I, and K have notes associated with their entries. Such notes and alerts are described in greater detail herein.

In some exemplary embodiments, display 402 displays a subset of all monitored individuals 10. In this way trainer 20 can focus on particular individuals 10. In some exemplary embodiments, the subset of individuals 10 displayed can be defined by trainer and display 402 can include a selection feature, for example, selection feature 428 of FIGS. 28 and 29, that allows trainer 20 to select to include or not include particular individuals 10 in the viewable subset.

Additionally or alternatively, the team view dashboard may show group summary metrics for groups of individuals 10 participating in the monitored athletic activity. The group summary metrics may be averages of the corresponding metrics for each individual belonging to the group, or the group summary metrics may be calculated using an independent algorithm designed to reflect a desired attribute of the group as a whole. In the exemplary display 402 of FIG. 13, present average heart rate, speed, training load, and power are shown for the team (i.e., Player A through Player H), and for a group including a sub-set of the team (i.e., Player A, Player C, and Player E). The values for heart rate, speed, training load, and power may update in real time during the athletic activity so as to reflect present values.

Team view dashboard is not limited to display of heart rate, speed, training load, and power, and is not limited to the display of 4 metrics. Team view dashboard can be customized to display those metrics most applicable or most beneficial to trainer 20, and may display, for example 3 to 5 distinct metrics for each individual 10. In some exemplary embodiments the metrics displayed can be set prior to the athletic activity during a setup procedure. In some exemplary embodiments the metrics displayed can be changed during the athletic activity by manipulation of input 404.

A particular metric of the displayed metrics in team dashboard view may be designated as a featured metric 414, which may be displayed with emphasis relative to other metrics. A featured metric may be independently designated (e.g., by trainer 20) for an individual 10, or for a group of individuals 10. Featured metric 414 may be displayed more prominently or in greater detail than other metrics, in order to allow trainer 20 to easily get an at-a-glance view of the featured metric across all individuals 10 participating in the athletic activity. In some exemplary embodiments featured metric 414 may be changed during monitoring of the athletic activity to any available metric, by appropriate manipulation of input 404 (e.g., selecting the metric desired to be featured, such as by selecting one of featured metric options 430 shown in, for example, FIG. 30). In some exemplary embodiments trainer 20 can toggle back and forth between featured metric views.

Featured metric 414 may be featured in a variety of ways. For example, it may be displayed in a color (or with a background color) different from that of the other displayed metrics, it may be displayed larger than the other metrics, it may flash or blink, it may include a larger background area than that of other metrics, it may be positioned closest to the identification information of individuals 10, it may include a status bar, chart, or graph (e.g., status bar 462), or it may exhibit a combination of these or other characteristics. In the exemplary display 402 of FIG. 13, heart rate is featured by including a larger background area than that of the other metrics and by being positioned closest to the identification information of individuals 10. In the exemplary display 402 of FIG. 27, power is featured by including a status bar next to the power entry for each individual 10. In the exemplary display of FIGS. 30 and 32, power is further featured by additionally displaying a value representing power larger than other values. In the exemplary display 402 of FIG. 31, heart rate is featured by including a status bar and by presenting a value representing heart rate larger than other values.

Some exemplary embodiments may, if alerts have been established for a metric of an individual 10, include an indication of whether a value of the metric is within particular zones relative to the alert parameters. For example, a color of the background area of the metric may change, or an icon may appear, based on, for example, whether the value is within or outside the zone, or on the proximity of the value to a threshold. In an exemplary embodiment where an alert is established for maintaining a heart rate of 85% of maximum or higher for 10 minutes or more, when a value of the heart rate of individual 10 is at 85% of maximum or higher, the background of the area containing the heart rate value of individual 10 is green, and when the heart rate has been at 85% of maximum or higher for 10 minutes or more, a star icon appears in the area containing the heart rate value of individual 10, and an audio sound is played by a speaker of group monitoring device 400. In some exemplary embodiments, as shown in, for example, FIGS. 31-33A, an indication that an alert has been triggered can be provided by a change in color of the area around the name of an associated individual 10, and a circle or other alert icon 432 representing the alert can be presented indicating the presence and/or number of alerts that are associated with the individual 10. The change in color may be maintained as long as an alert is active, or may change at the triggering of the alert, and fade or change back to its original color after a period of time. In some exemplary embodiments, individual monitors 200 can provide indication of an alert to an associated individual 10 via, for example, emitting an audible noise, vibrating, or providing a visual indication (e.g., via an LED or LCD display).

Figure 33A:
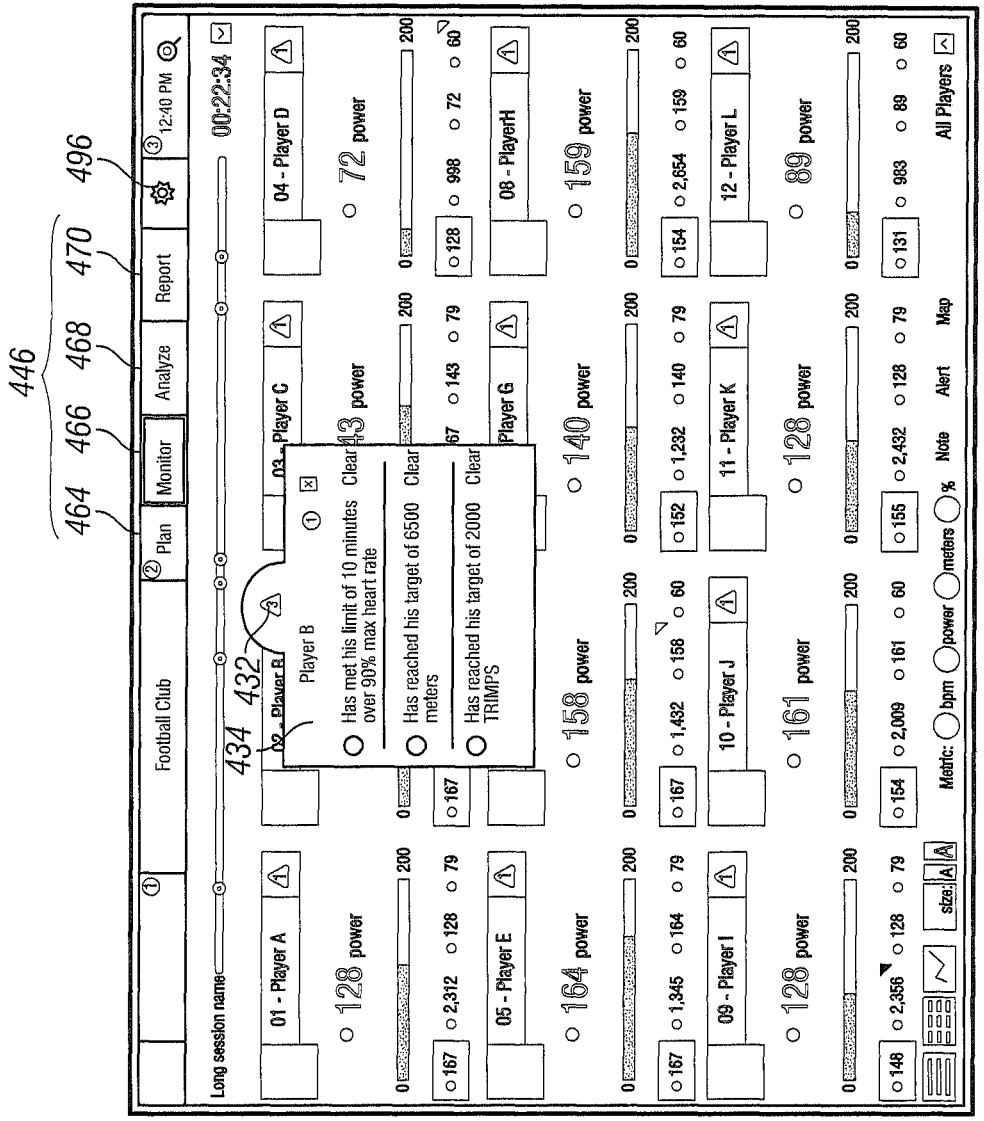
FIG. 33A depicts a display of a group monitoring device according to an exemplary embodiment of the present invention.
Figure 33B:
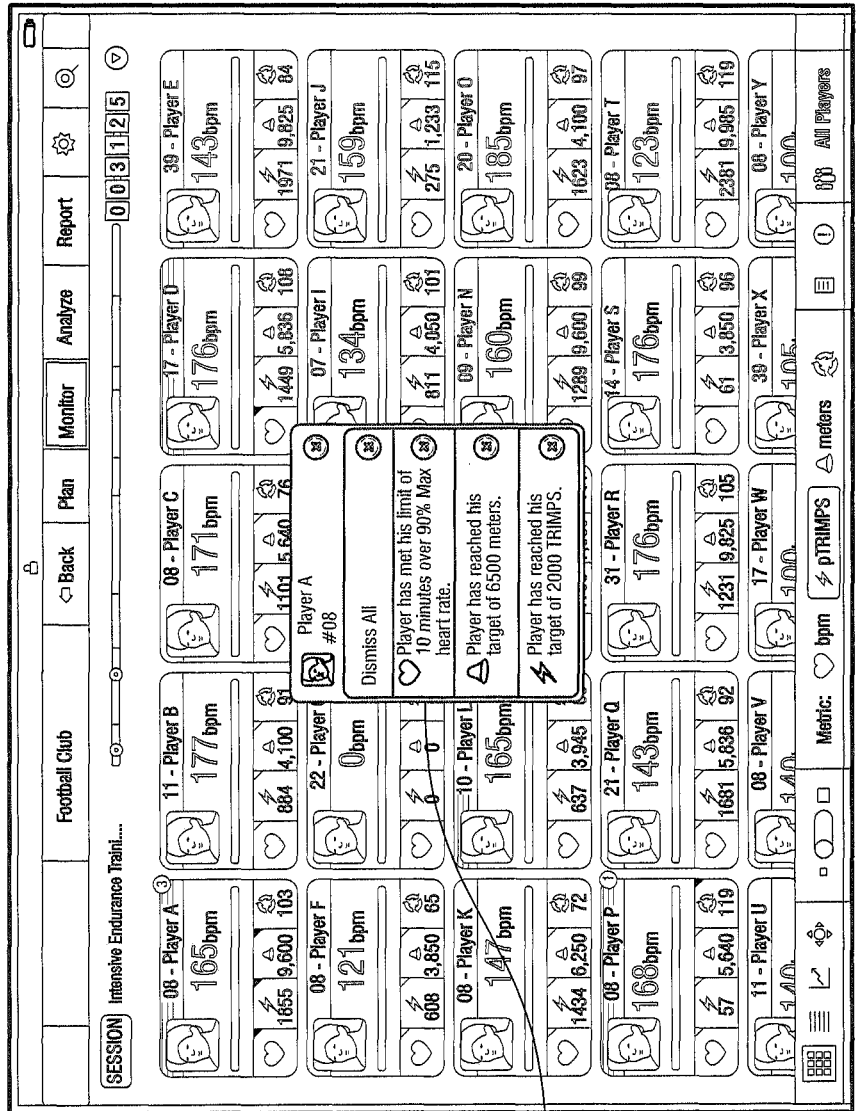
FIG. 33B depicts a display of a group monitoring device according to an exemplary embodiment of the present invention.
Figure 34:
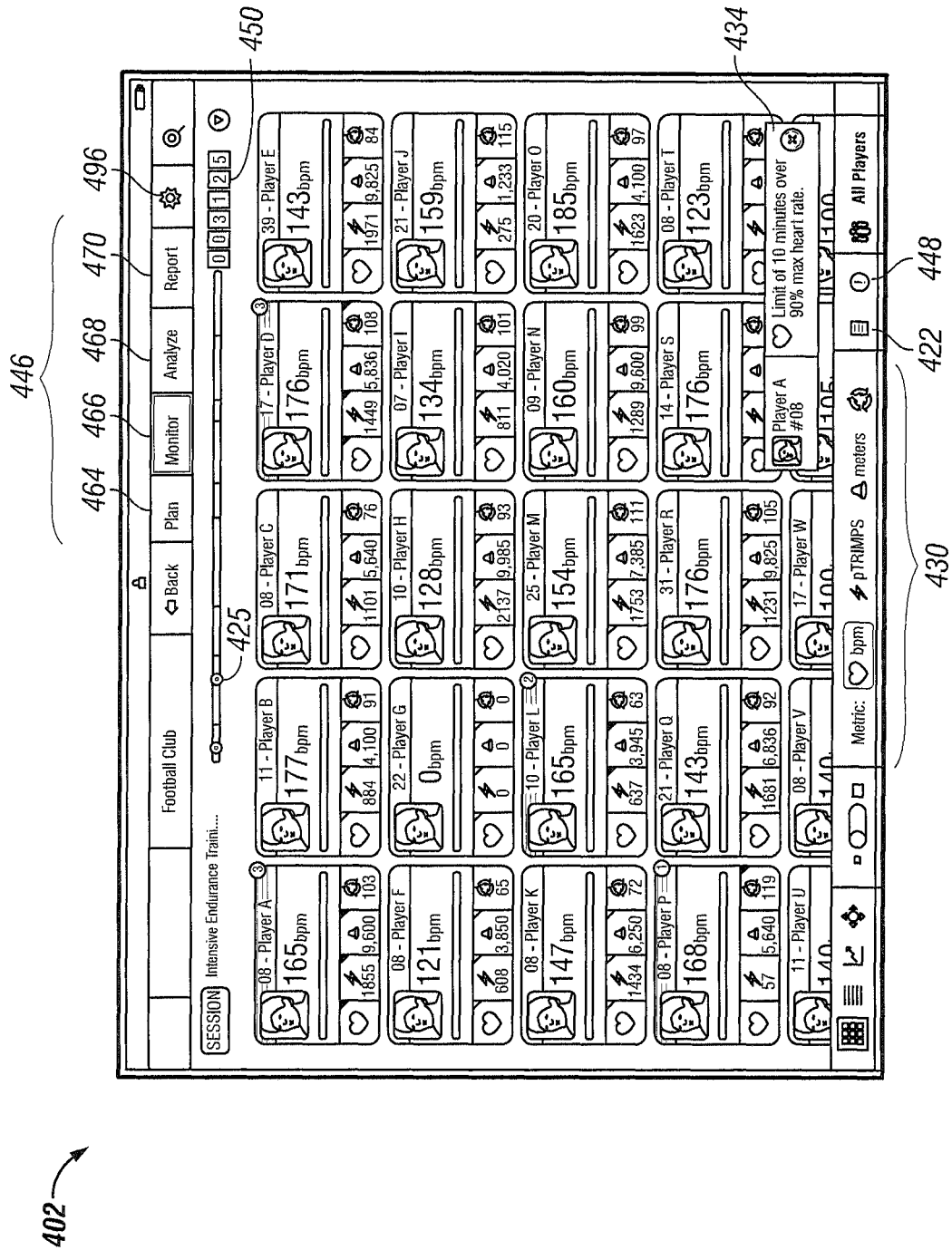
FIG. 34 depicts a display of a group monitoring device according to an exemplary embodiment of the present invention.

In some exemplary embodiments, if an alert is triggered, trainer 20 can select a representation of the alert to thereby access more information about the alert, as shown in, for example, FIGS. 33A and 34. In some exemplary embodiments, selecting the representation of the alert leads to a detailed chart view of the metric that triggered the alert. In some exemplary embodiments, display 402 may display all active alerts, at a point or period in time, for all monitored individuals 10 or subsets thereof. In some exemplary embodiments, new alerts can be indicated by, for example, a flashing icon or a temporary pop-up box 434 showing information relating to the new alert, as is shown in the exemplary embodiments of FIGS. 33A, 33B, 34, and 35A-35D, for example.

In some exemplary embodiments, pop-up box 434 includes information about a single alert (e.g., FIG. 33A). In some exemplary embodiments, pop-up box 434 includes information about multiple alerts (e.g., FIG. 33B). The multiple alerts can be displayed according to any suitable criteria, for example, the multiple alerts may be active alerts related to a particular individual 10 or group of individuals 10, or may be alerts triggered within some time period prior to the present time. In some exemplary embodiments, pop-up box 434 indicates the presence and/or number of alerts triggered. This number may include, for example, all active alerts, all unviewed alerts, or the number of alerts triggered within some time period prior to the present time (e.g., FIG. 35C). In some exemplary embodiments, a pop-up box 434 indicating the number of alerts triggered appears in the place of a pop-up box 434 including additional alert information when the number of alerts to be displayed is above some threshold number.

Figure 35A:
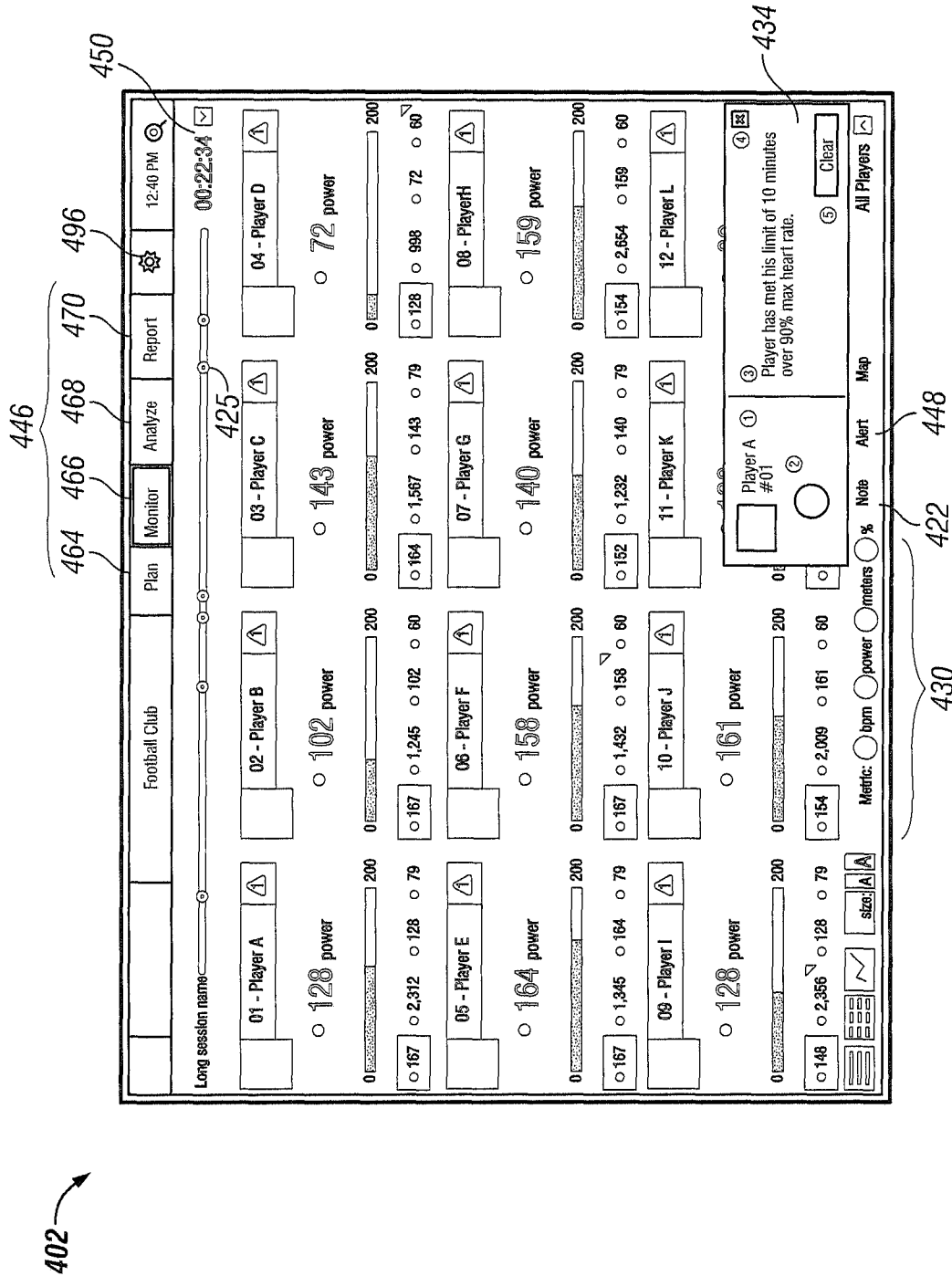
FIG. 35A depicts a display of a group monitoring device according to an exemplary embodiment of the present invention.
Figure 35B:
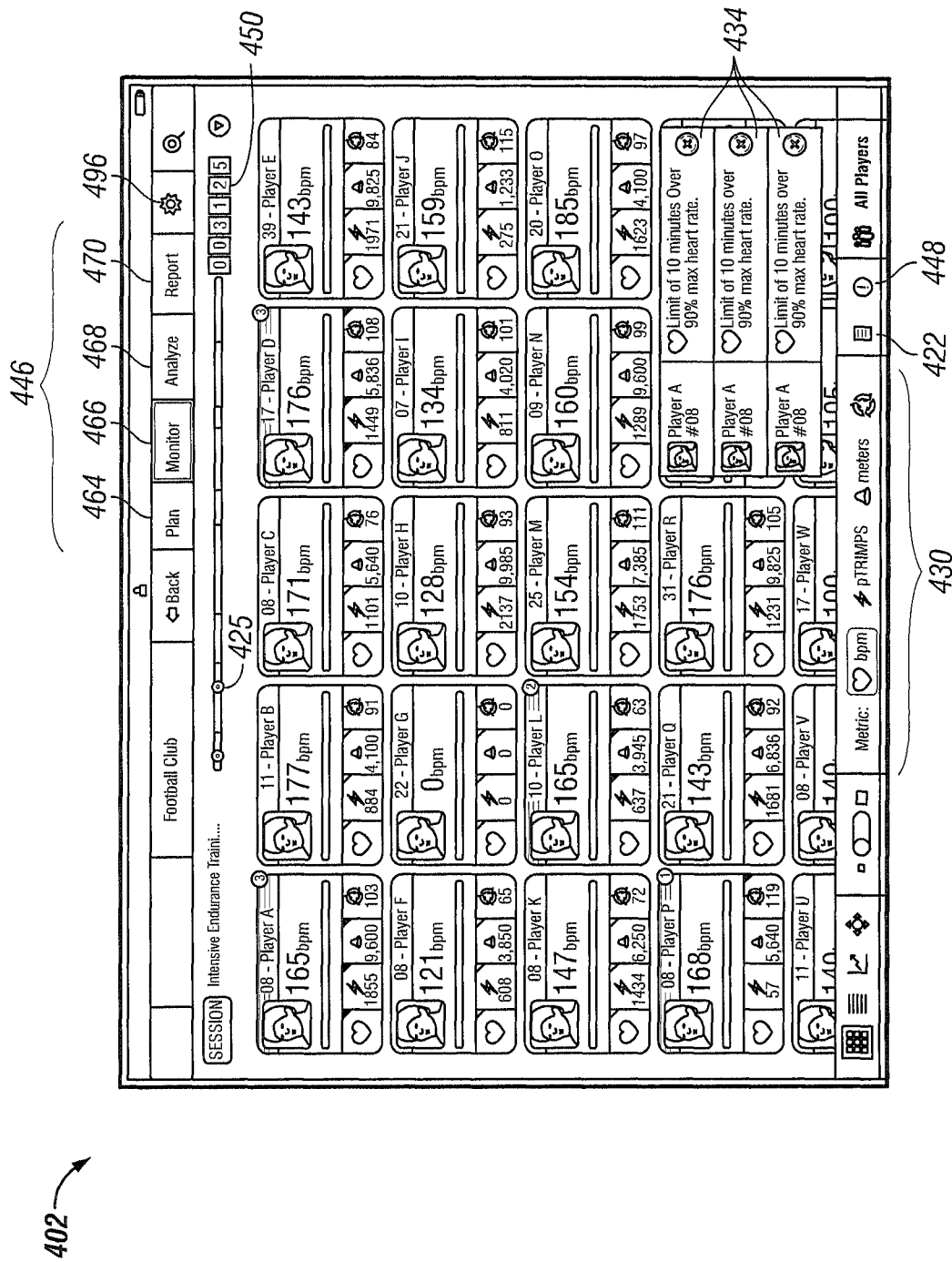
FIG. 35B depicts a display of a group monitoring device according to an exemplary embodiment of the present invention.
Figure 35C:
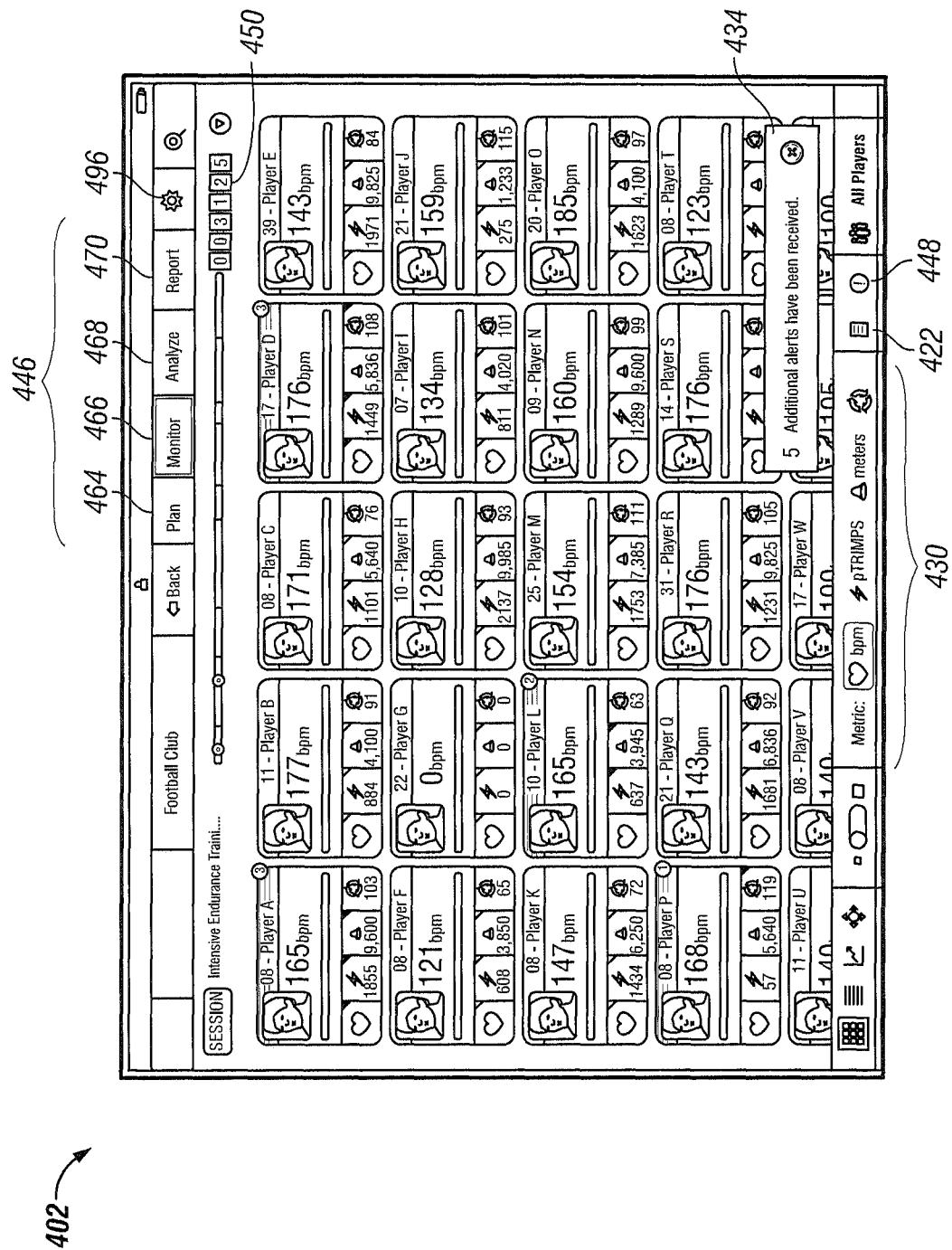
FIG. 35C depicts a display of a group monitoring device according to an exemplary embodiment of the present invention.
Figure 35D:
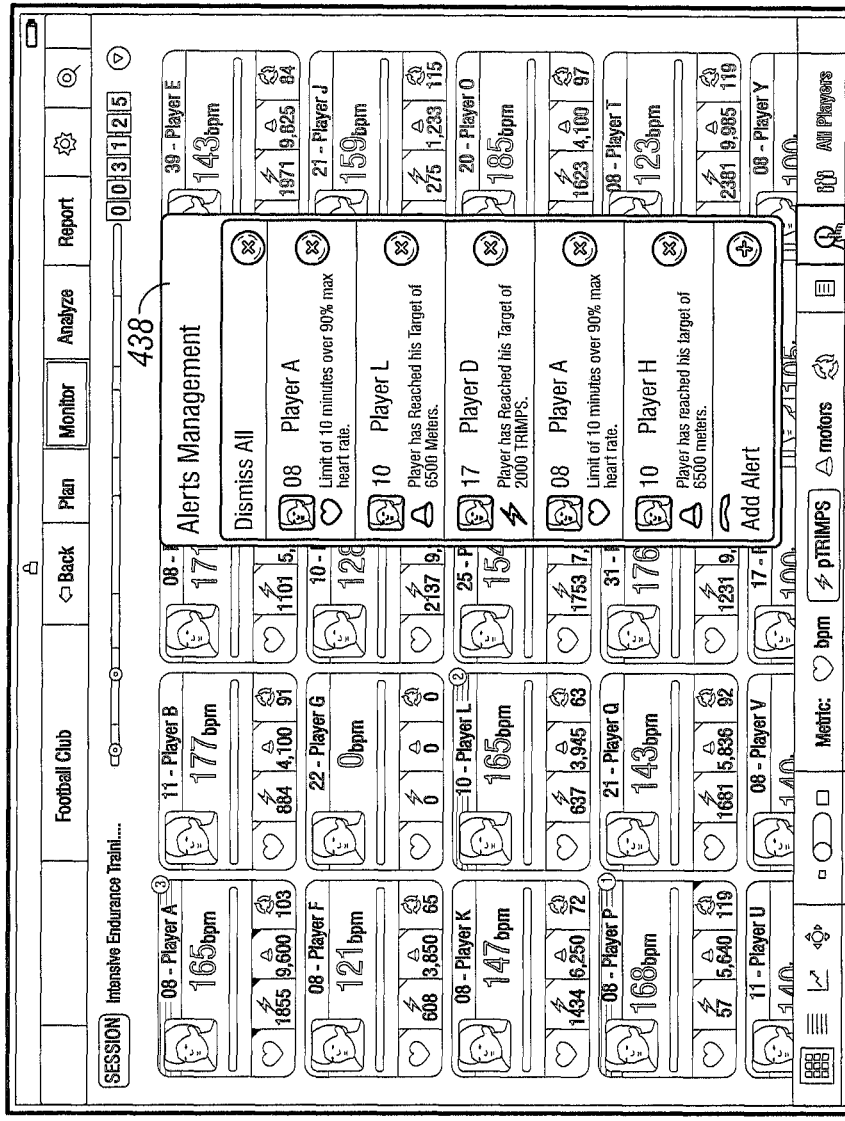
FIG. 35D depicts a display of a group monitoring device according to an exemplary embodiment of the present invention.
Figure 36A:
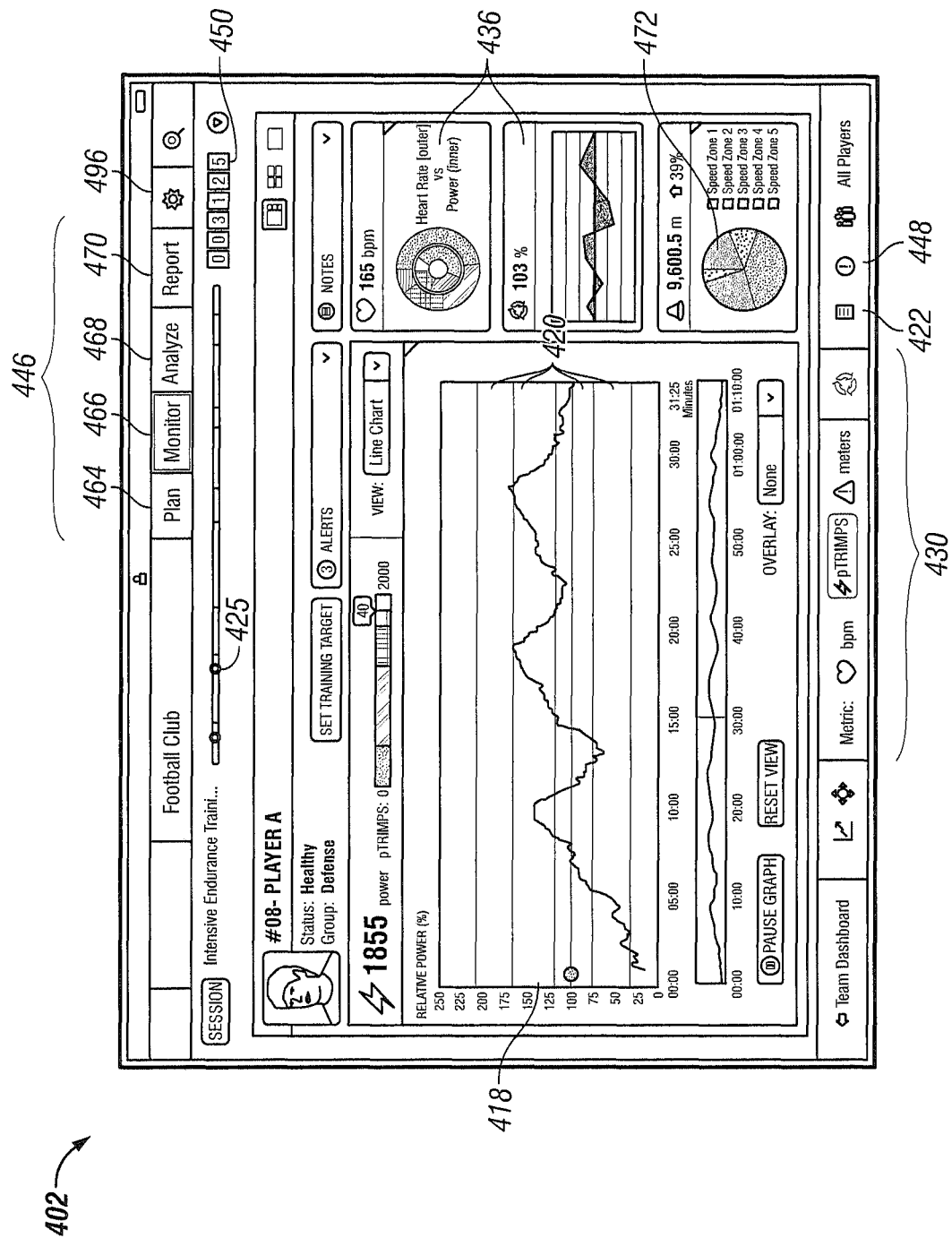
FIG. 36A depicts a display of a group monitoring device according to an exemplary embodiment of the present invention.
Figure 36B:
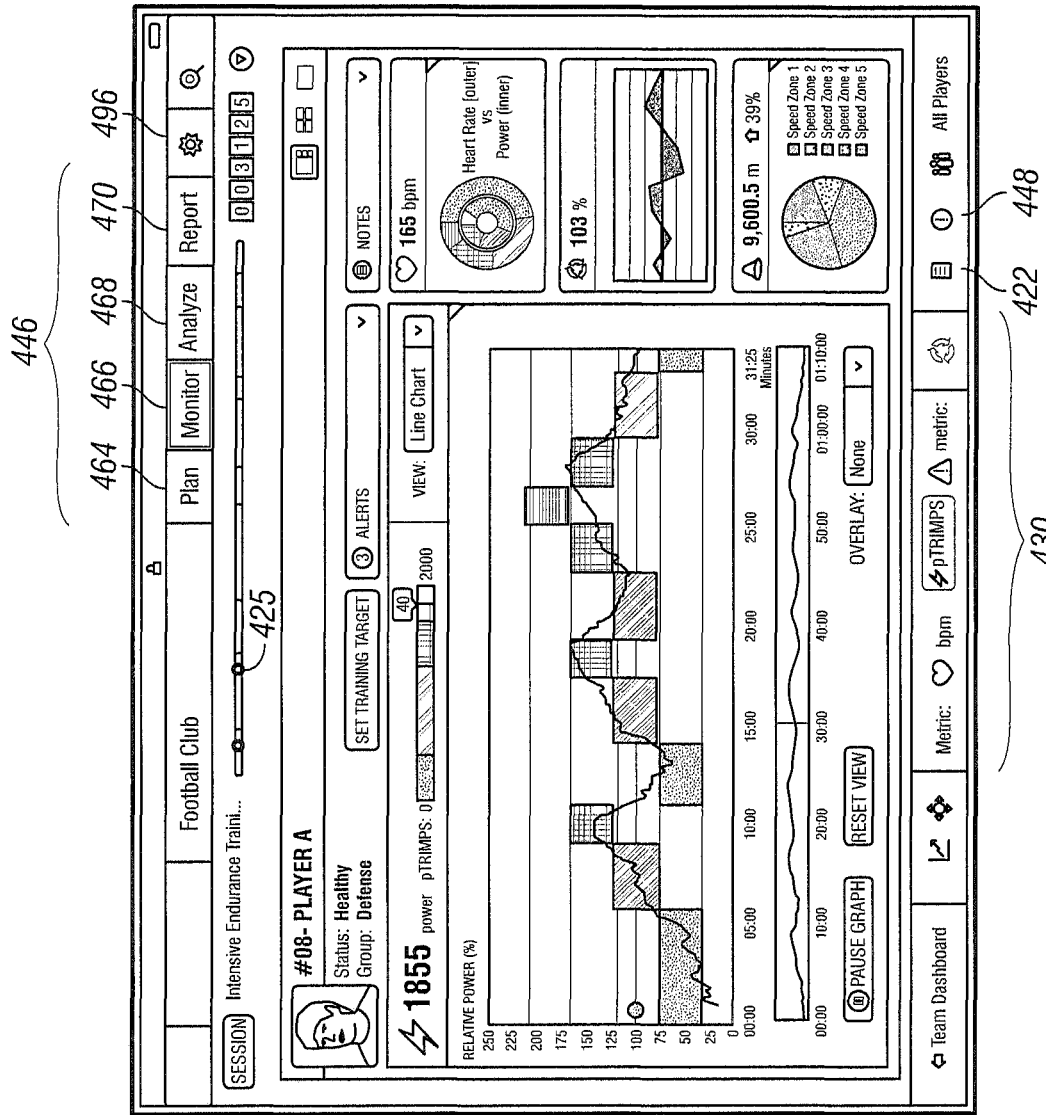
FIG. 36B depicts a display of a group monitoring device according to an exemplary embodiment of the present invention.
Figure 37A:
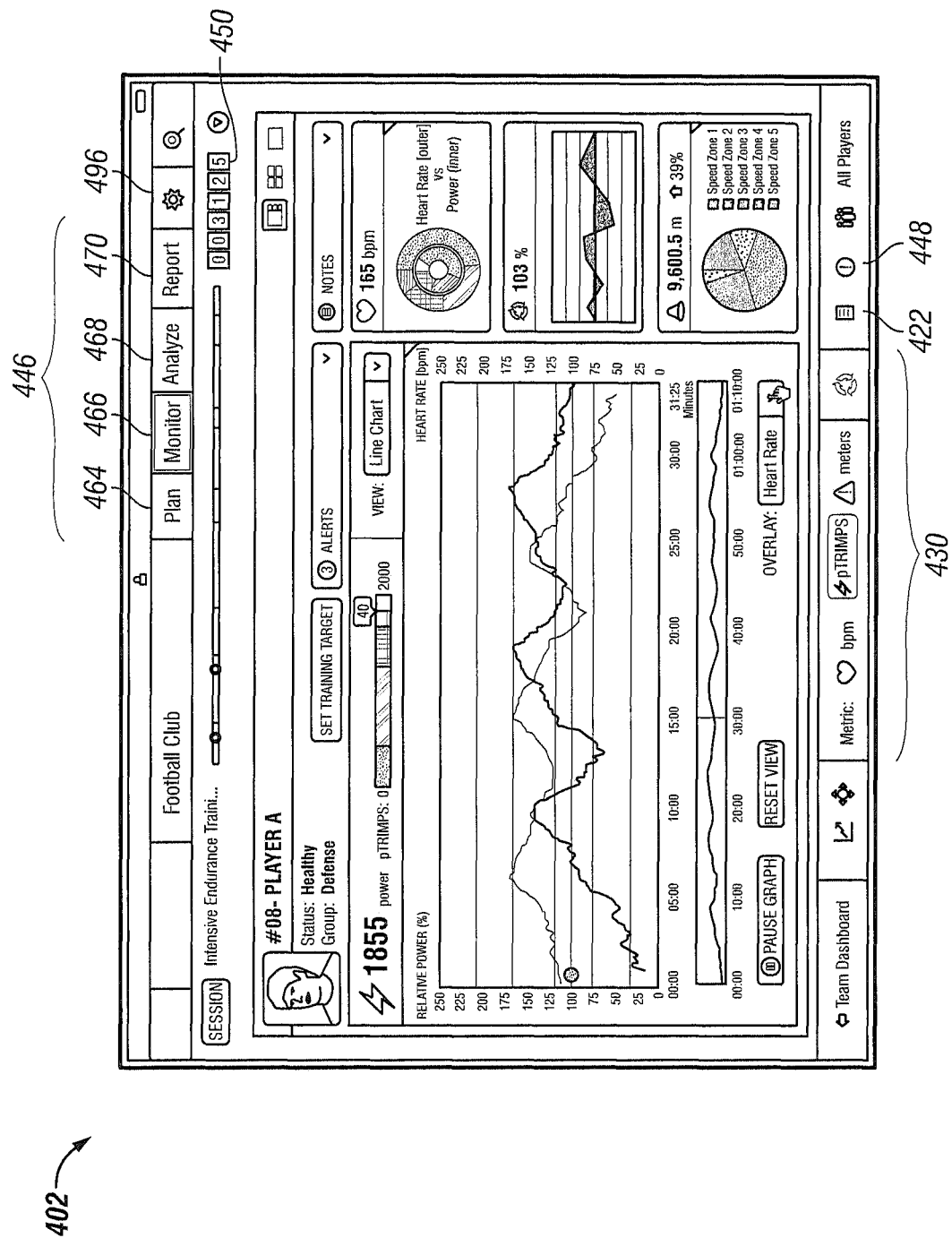
FIG. 37A depicts a display of a group monitoring device according to an exemplary embodiment of the present invention.
Figure 37B:
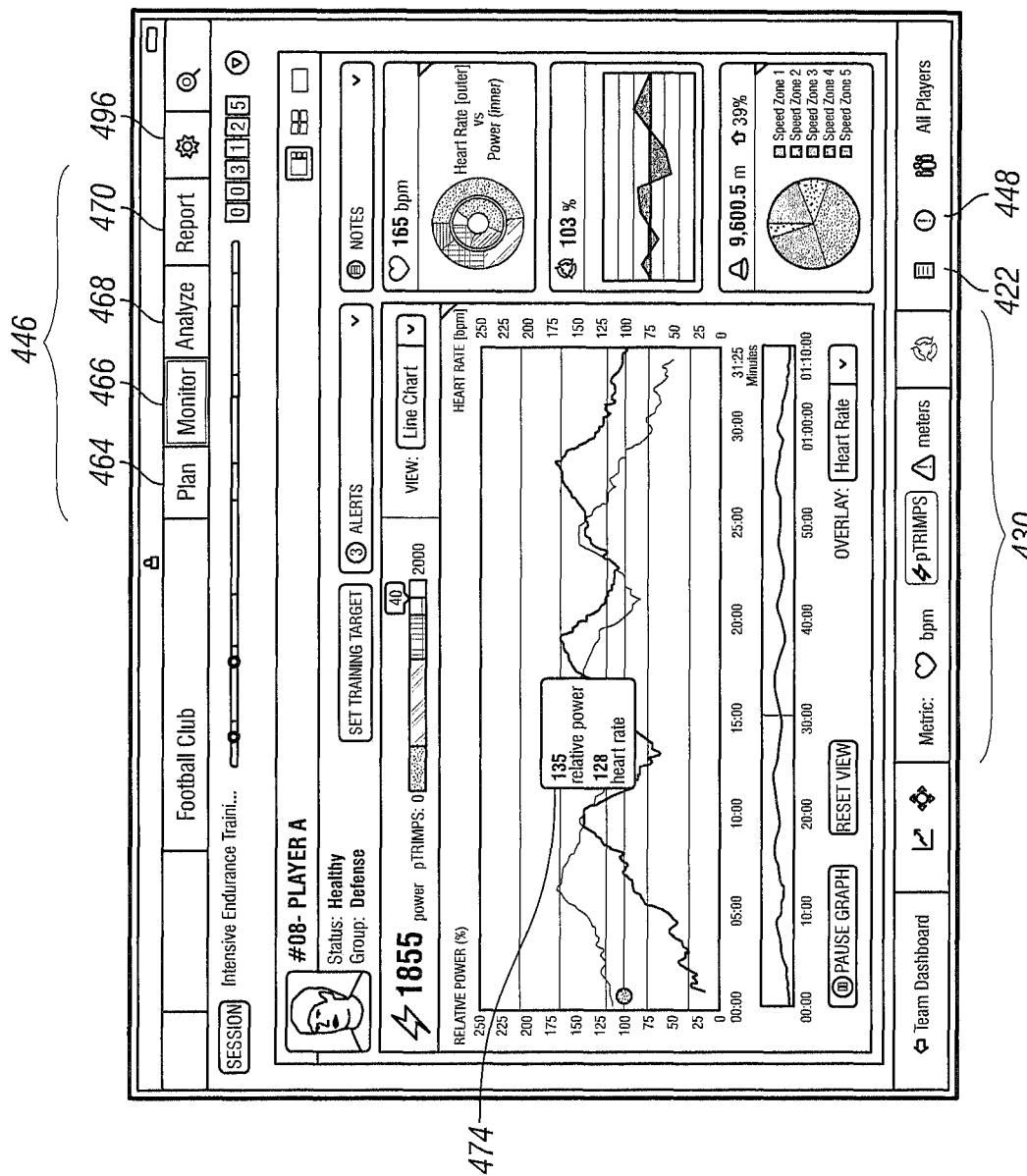
FIG. 37B depicts a display of a group monitoring device according to an exemplary embodiment of the present invention.
Figure 38:
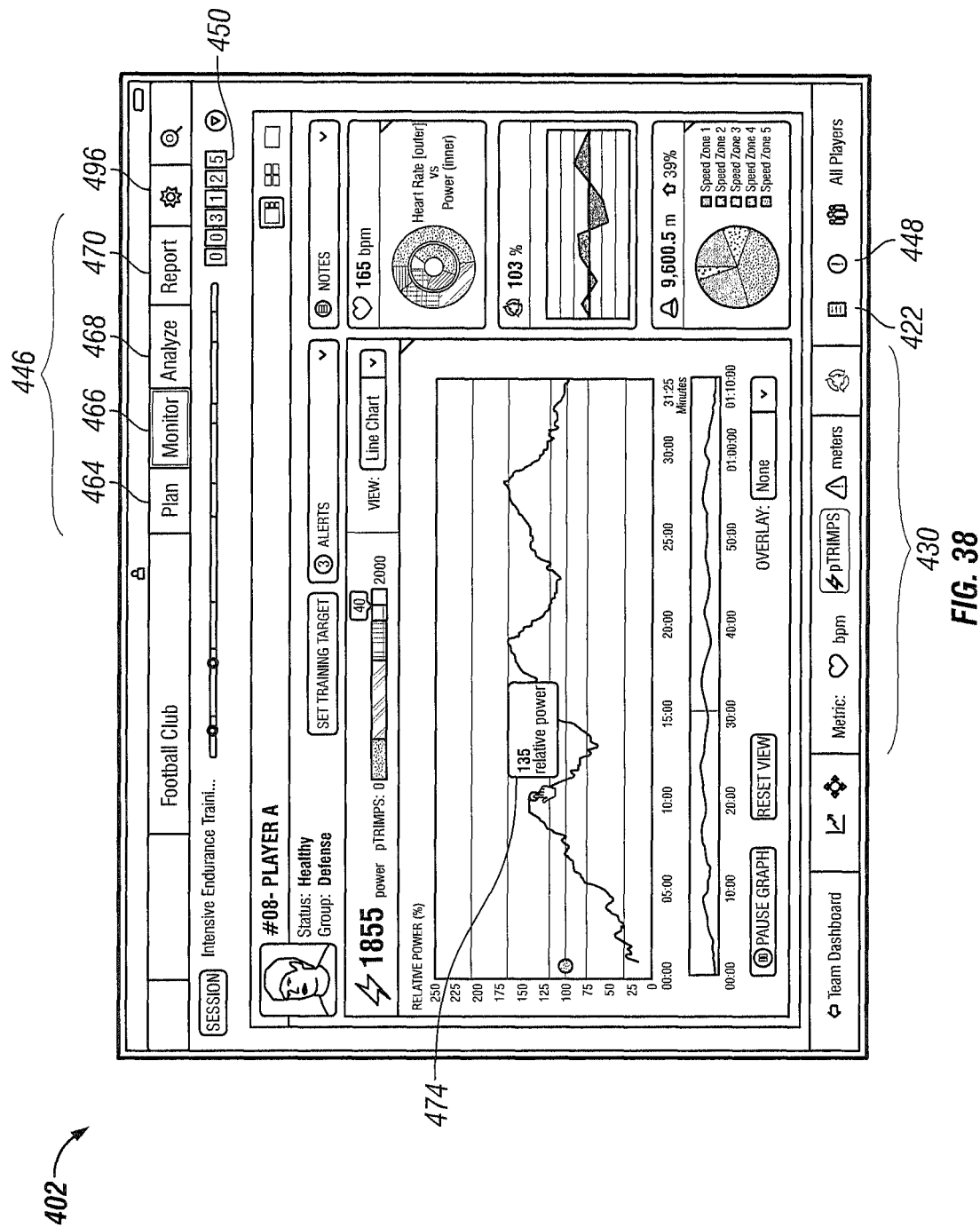
FIG. 38 depicts a display of a group monitoring device according to an exemplary embodiment of the present invention.
Figure 39:
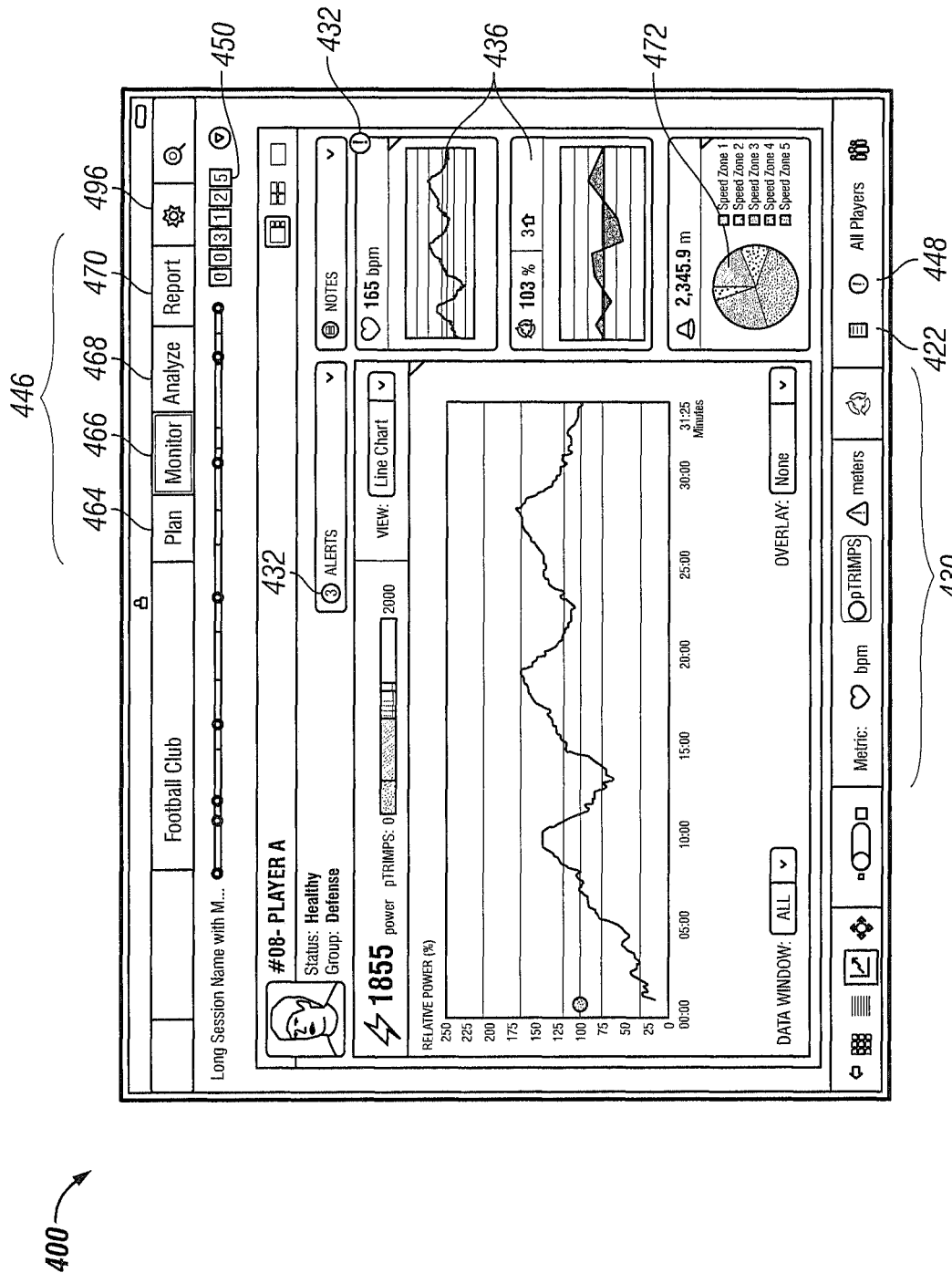
FIG. 39 depicts a display of a group monitoring device according to an exemplary embodiment of the present invention.

In some exemplary embodiments, an alert management window 438 can be displayed in response to selection of an alert management icon 448, as depicted in, for example, FIG. 35D. Alert management window 438 may include information about all active alerts or a subset thereof, and may allow dismissal or acknowledgement of such alerts.

In some exemplary embodiments, the team view dashboard is sortable in real time. Trainer 20 may manipulate input 404 so as to cause display 402 to show information for individuals 10 sorted by a desired metric. For example, trainer 20 may select a displayed heart rate metric (by, for example, selecting the metric label or a sort icon associated with the metric), and the information for individuals 10 may be rearranged so as to be represented in ascending or descending order. For example, FIG. 19 shows individuals 10 rearranged from the individual 10 with the lowest heart rate to the individual 10 with the highest heart rate. Further selections of the heart rate metric may cause the information for individuals 10 to change from ascending to descending representations, and vice versa. In some exemplary embodiments, trainer 20 may similarly sort by, for example, name 406, position in space (e.g., location on the field or court), position on team (e.g., goalkeeper, defender, point guard), jersey number 408, physiological status, connection status, or active alerts. Such features can allow trainer 20 to easily see which individuals 10 have high and low metrics relative to other individuals 10.

In some exemplary embodiments, the team view dashboard is filterable in real time. Trainer 20 may manipulate input 404 so as to cause display 402 to show information for a subset of individuals 10. For example, trainer 20 may select one or more groups representing a subset of individuals 10. Groups can be selected in a variety of ways. In some exemplary embodiments trainer 20 selects a group label or a filter icon associated with the group. In some exemplary embodiments trainer 20 selects individuals to create a group in real time. In some exemplary embodiments trainer 20 inputs information used to identify members of a group, such as, for example, all individuals 10 having higher than a particular a heart rate, all individuals 10 having higher than a particular training load percentage, all individuals assigned a particular position, or all individuals having a particular physiological status. When a group is selected the display may change such that information for only those individuals 10 that are included in the group is displayed. Such features can allow trainer 20 to easily focus on the metrics associated with a group of individuals 10.

In some exemplary embodiments, the team view dashboard can also be used to monitor the status of connection of individual monitors 200 to base station 300. If, for example, an individual 10 travels out of range of base station 300, base station 300 may not receive normal transmissions from the individual monitor 200 of that individual 10. The team view dashboard can indicate that no data is being received by base station 300 for that individual 10 by, for example, graying out the identification information of that individual 10 (see, e.g., Player G of FIGS. 27, 31, 32, and 34), by including a strikethrough through information relating to that individual 10, or by including an icon in association with the identification information of that individual 10.

Figures 17, 18:
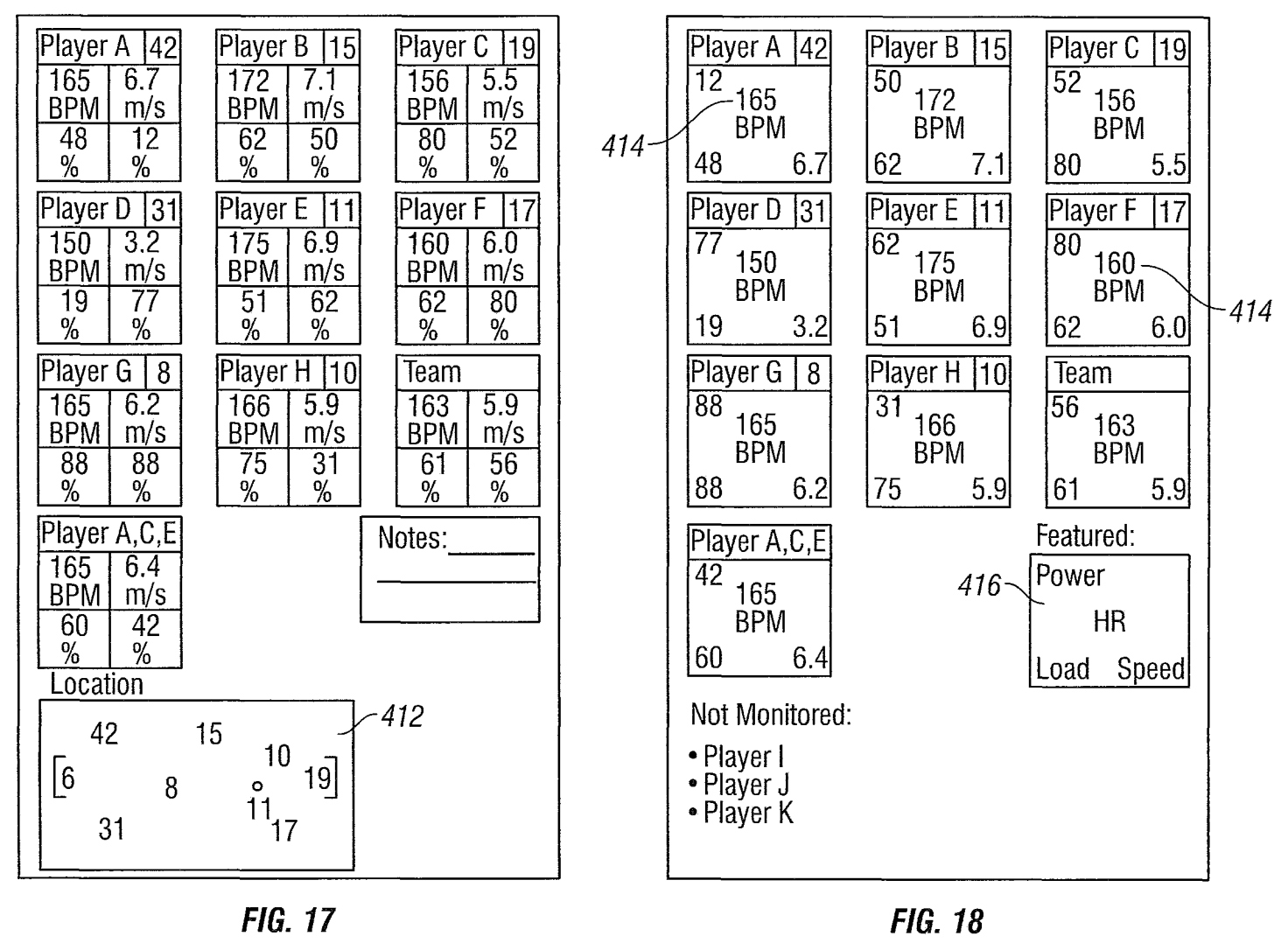
Figure 60:
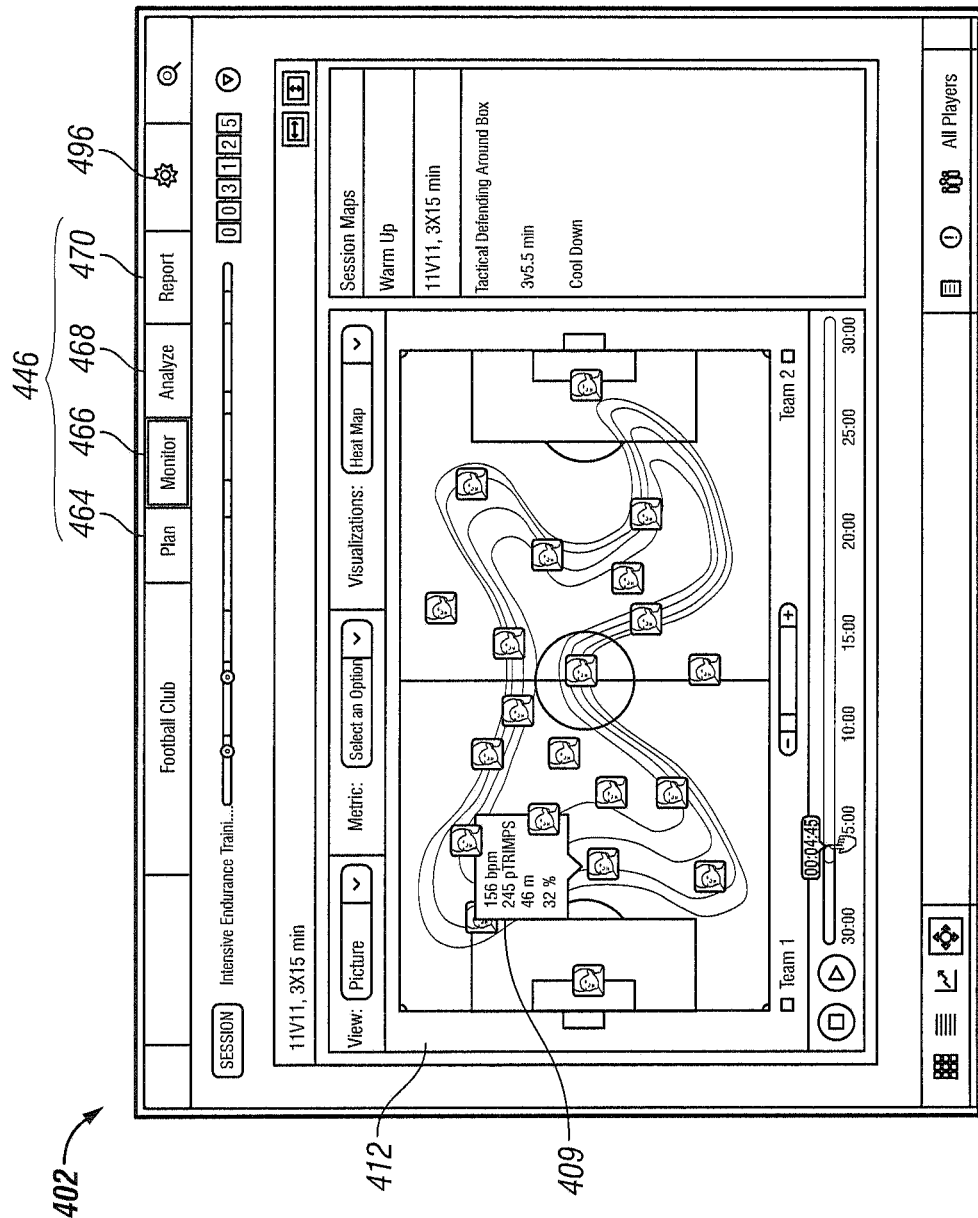
FIG. 60 depicts a display of a group monitoring device according to an exemplary embodiment of the present invention.

In some exemplary embodiments, alternative representations can replace the above-described representation of FIG. 13, or can be used as selectable alternative views, allowing trainer 20 to choose between the above-described representation and the alternative representations. The alternative representations of FIGS. 17 and 18 include multiple panels, each showing information for a particular individual 10. FIG. 17 includes a location component 412 showing the present location of individuals 10 on playing field 30, where individuals 10 are depicted represented by their identifying numbers. In some exemplary embodiments, as depicted in, for example, FIG. 60, individuals 10 are represented by their photographs. FIG. 18 includes a featured metric 414 (heart rate) displayed prominently in the center of each panel, as well as a key 416 showing what metric the values in each panel represent. Trainer 20 may select a metric on key 416 to have it displayed as the featured metric 414. FIG. 18 also includes a list of individuals 10 not actively monitored. Trainer 20 may select an individual 10 from this list to actively monitor that individual. Operation of the alternative representations of FIGS. 17 and 18 is similar to operation of the above-described representation of FIG. 13.

In some exemplary embodiments, location component 412 shows the present location of individuals 10 on the playing field, and selection of a representation of one of individuals 10 triggers display of a status box displaying information about the current status of the selected individual 10. In some exemplary embodiments, as depicted in, for example, FIG. 60, location component 412 may include a heat map 413, providing a visual indication of concentrations of individuals 10 in areas of the playing field, which information may help trainer 20 determine whether to redistribute individuals 10. Such visual indication may include coloring areas of higher concentration of individuals 10 differently from areas of lower concentrations of individuals 10. Location component 412 can be used to monitor individuals 10 in real time, or can be used to review the locations of individuals 10 from a past session of athletic activity or earlier in the present session of athletic activity.

In an exemplary embodiment, display 402 of group monitoring device 400 shows an individual view dashboard (see, for example, the exemplary displays 402 of FIGS. 16 and 36A, 36B, 37A, 37B, and 38-41). Trainer 20 may access an individual view dashboard by, for example, selecting an individual 10 on the team view dashboard. The individual view dashboard may show information about the selected individual 10, such as, for example, biographical information (e.g., photograph 410, name 406, jersey number 408, position), attributes (e.g., height, weight), metrics (e.g., time active, heart rate, speed, distance traveled, intensity level, training load, efficiency, location), statistics (e.g., points scored), alerts, notes, and condition (e.g., active, healthy, rehabilitation). In some exemplary embodiments the individual view dashboard shows different information about the selected individual 10 than that shown in the embodiment of FIG. 16.

In some exemplary embodiments, when trainer 20 selects an information entry, a detailed view of that information may be displayed. For example, if trainer 20 selects 'heart rate' on the individual view dashboard for Player A shown in FIG. 16, display 402 may display a detailed chart and/or graph 418 showing a history of Player A's heart rate throughout the present athletic activity (see, e.g., FIG. 20). In some exemplary embodiments, trainer 20 may select a 'power' indicator on the individual view dashboard, and display 402 may display a detailed chart and/or graph 418 showing a history of the selected player's power (see, e.g., FIG. 36A).

In some exemplary embodiments, any applicable alert information (e.g., training zones, thresholds) specific to the selected metric for selected individual 10 is displayed in the detailed view. For example, as shown in the detailed views of FIGS. 20 and 36A, training zones 420 for Player A's heart rate are overlaid on graph 418 of Player A's heart rate. In some exemplary embodiments, areas of zones 420 may be highlighted where coincident with data of graph 418, as depicted in, for example, FIG. 36B. Also, for example, as shown in the detailed view of FIG. 36A, training zones 420 (e.g., for a player's speed) may be displayed in a pie chart 472. In some exemplary embodiments, alerts relevant to a particular metric may be indicated by an icon displayed in association with the chart and/or graph indicative of that metric. For example, in the detailed view of FIG. 39, an alert icon 432 indicates an alert associated with the player's heart rate, and an alert icon 432 indicates 3 alerts associated generally with the player.

Figure 40:
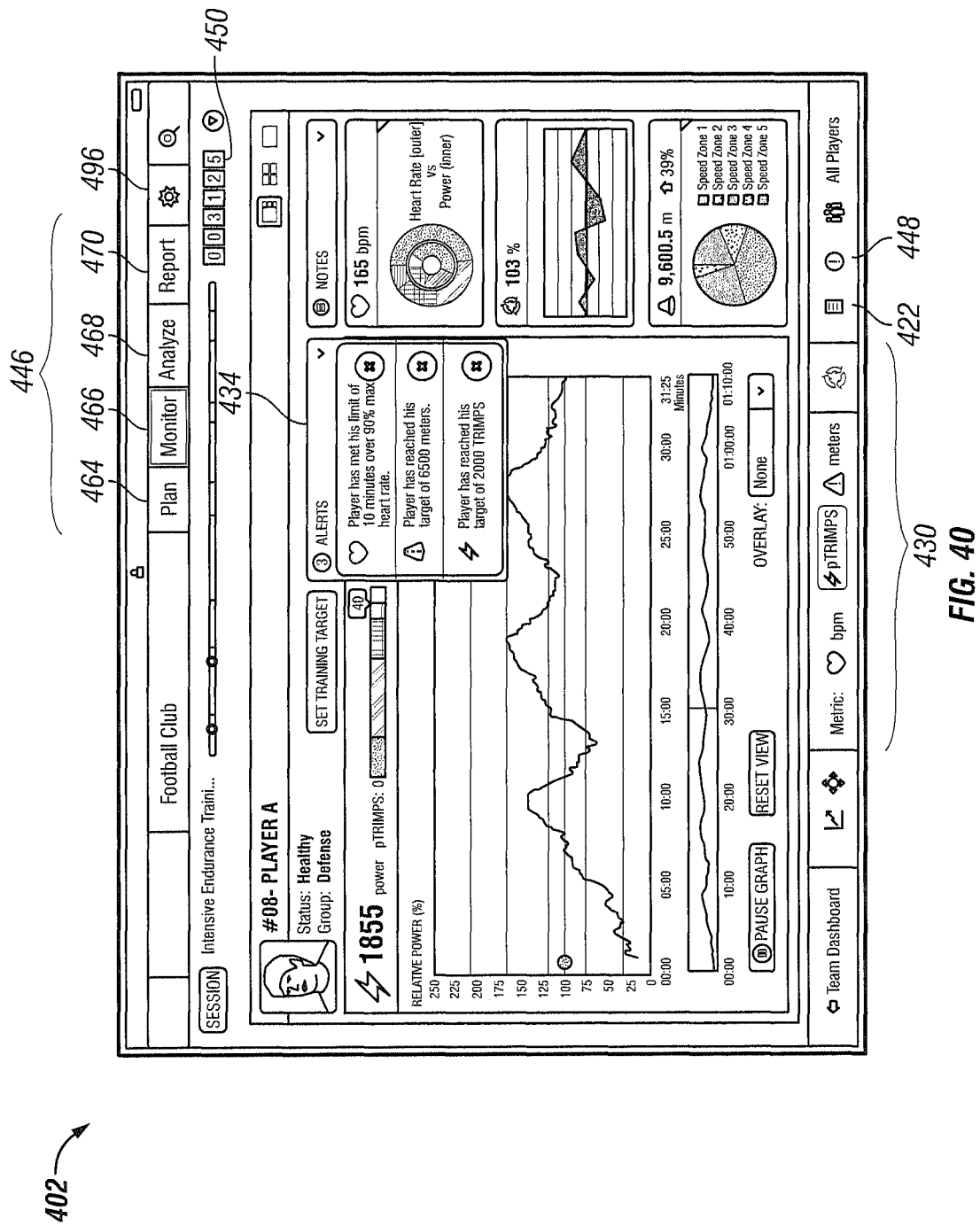
FIG. 40 depicts a display of a group monitoring device according to an exemplary embodiment of the present invention.

Selection of these alerts may trigger presentation of more detailed information about the alert, for example, in the form of a pop-up graphic 434, as shown in FIG. 40. In some exemplary embodiments, trainer 20 can select multiple information entries and display 402 can incorporate information regarding the selected multiple information entries in the detailed view. For example, FIG. 20 shows Player A's speed shown in graph 418 of display 402. In some exemplary embodiments, display 402 may display additional detailed charts and/or graphs 436 while displaying the primary chart and/or graph 418. In some exemplary embodiments, the additional detailed charts and/or graphs 436 are displayed less prominently (e.g., smaller) than the primary chart and/or graph 418, as depicted in, for example, FIGS. 36A and 39. In some exemplary embodiments, if an area on chart and/or graph 418 is selected (e.g., by trainer 20), more detailed information about the displayed metric may be displayed. For example, selecting a particular point on a line graph may trigger display of a graphic 474 indicating the value of one or more metrics at that point (see, e.g., FIGS. 37B and 38). In some exemplary embodiments, chart and/or graph 418 may include information indicative of more than one metric. For example, chart and/or graph 418 may include power and heart rate on the same chart and/or graph (see, e.g., FIGS. 37A and 37B).

In some exemplary embodiments, chart and/or graph 418 may include metric information for past sessions of athletic activity, which may be stored within group monitoring device 400 or transmitted thereto by, for example, base station 300. In some exemplary embodiments, chart and/or graph 418 may include information indicative of more than one time period for one or more metrics. For example, chart and/or graph 418 may include heart rate information for the present or most recent session of athletic activity separate from or overlaid with heart rate information for one or more prior sessions of athletic activity on the same chart and/or graph.

Figure 41:
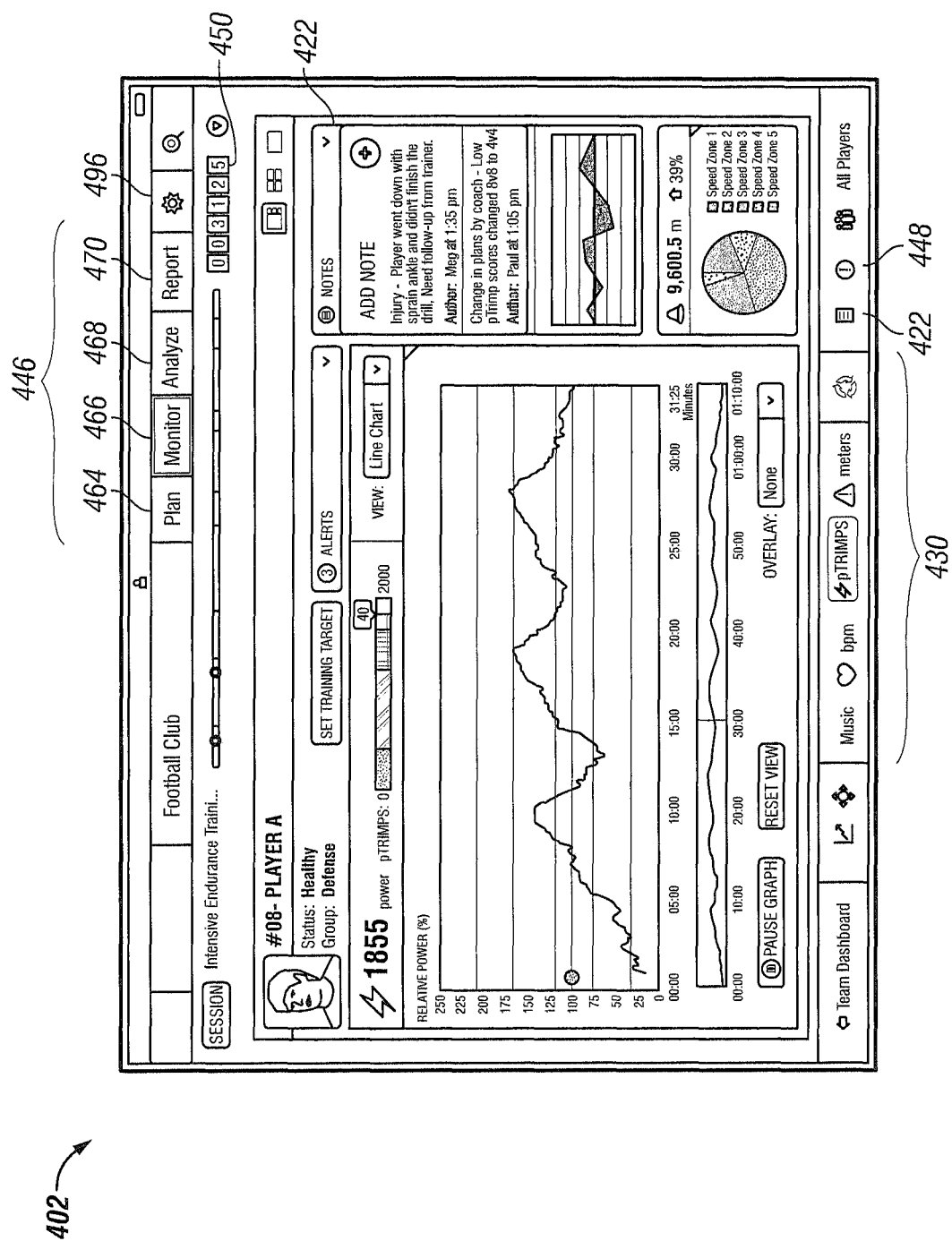
FIG. 41 depicts a display of a group monitoring device according to an exemplary embodiment of the present invention.
Figure 44:
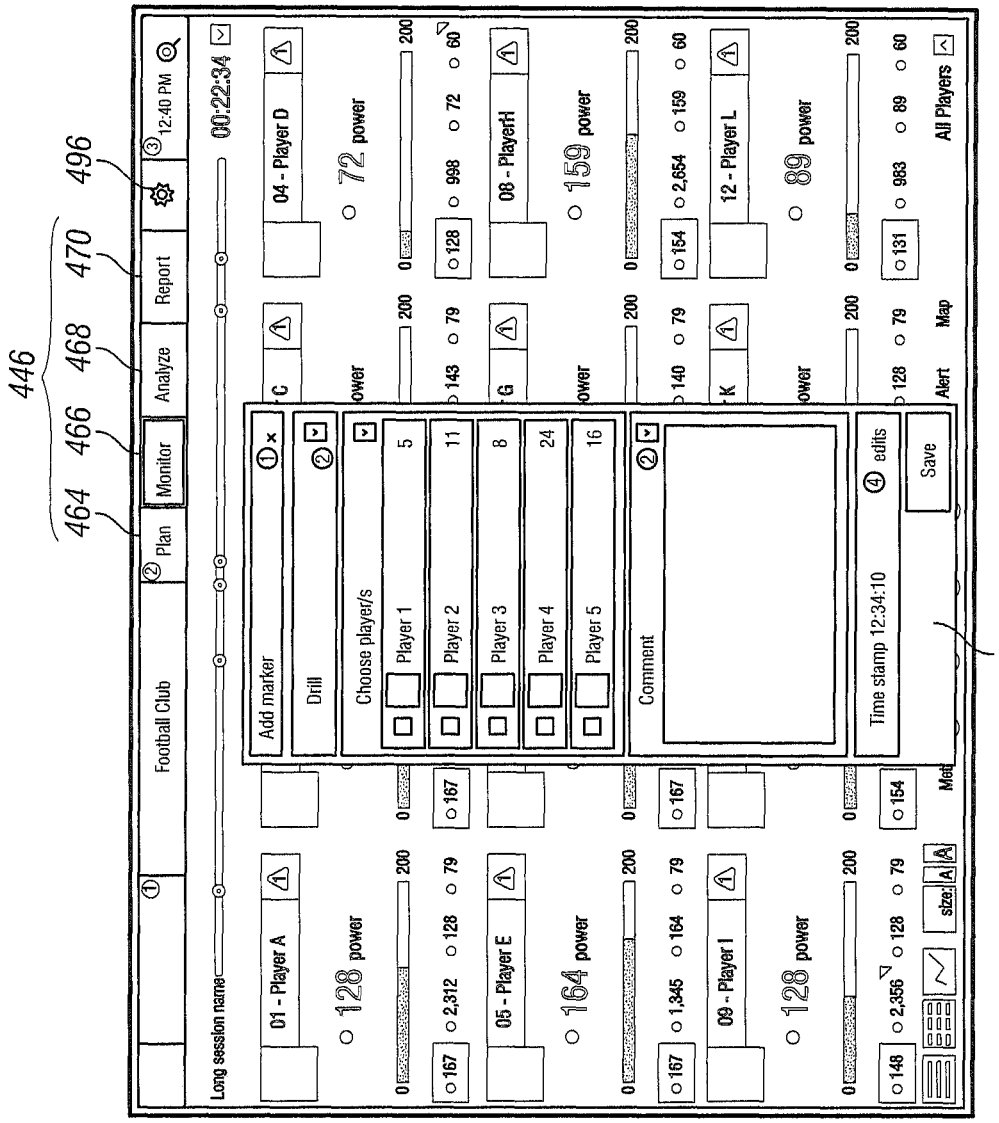
FIG. 44 depicts a display of a group monitoring device according to an exemplary embodiment of the present invention.
Figure 45:
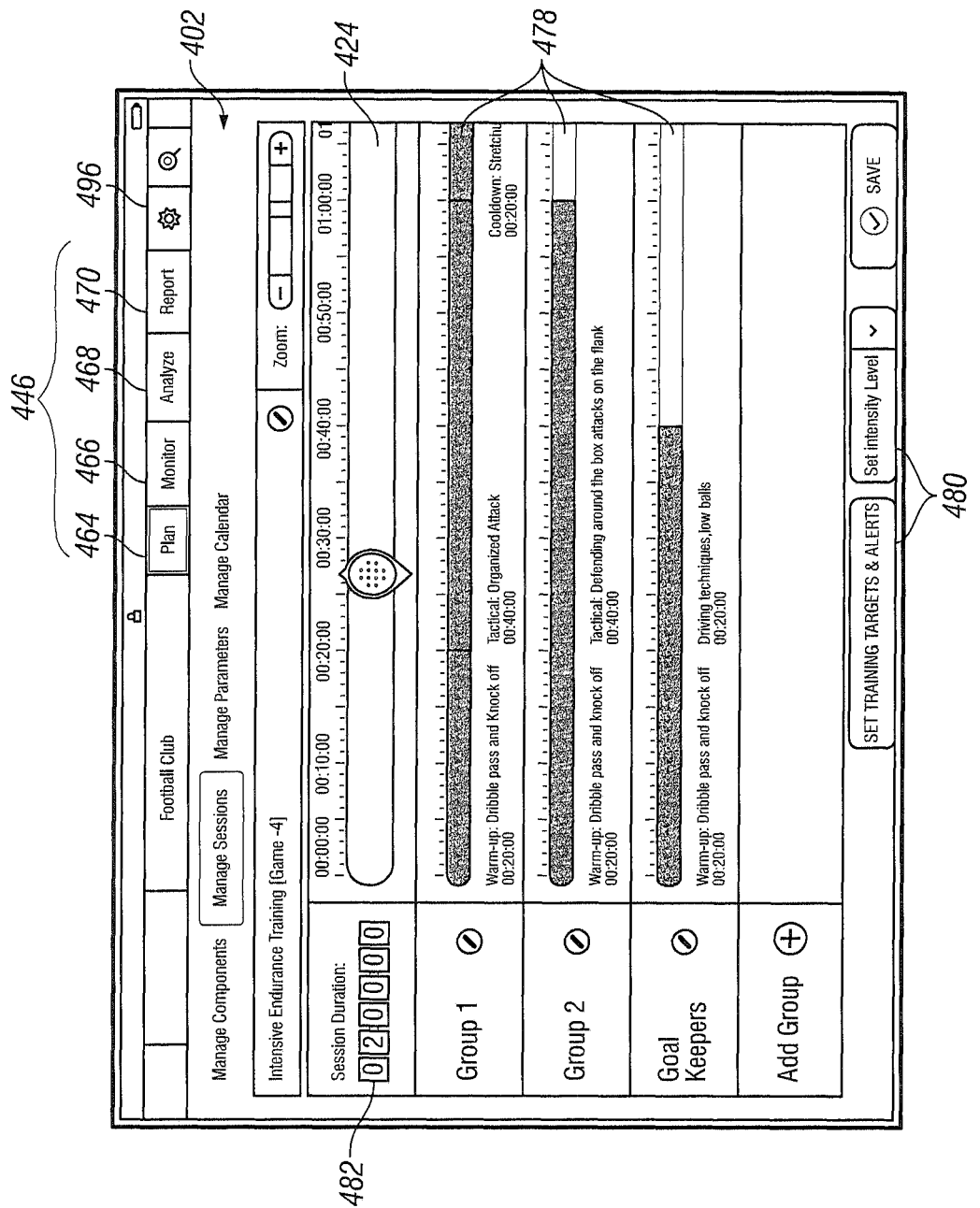
FIG. 45 depicts a display of a group monitoring device according to an exemplary embodiment of the present invention.
Figure 46:
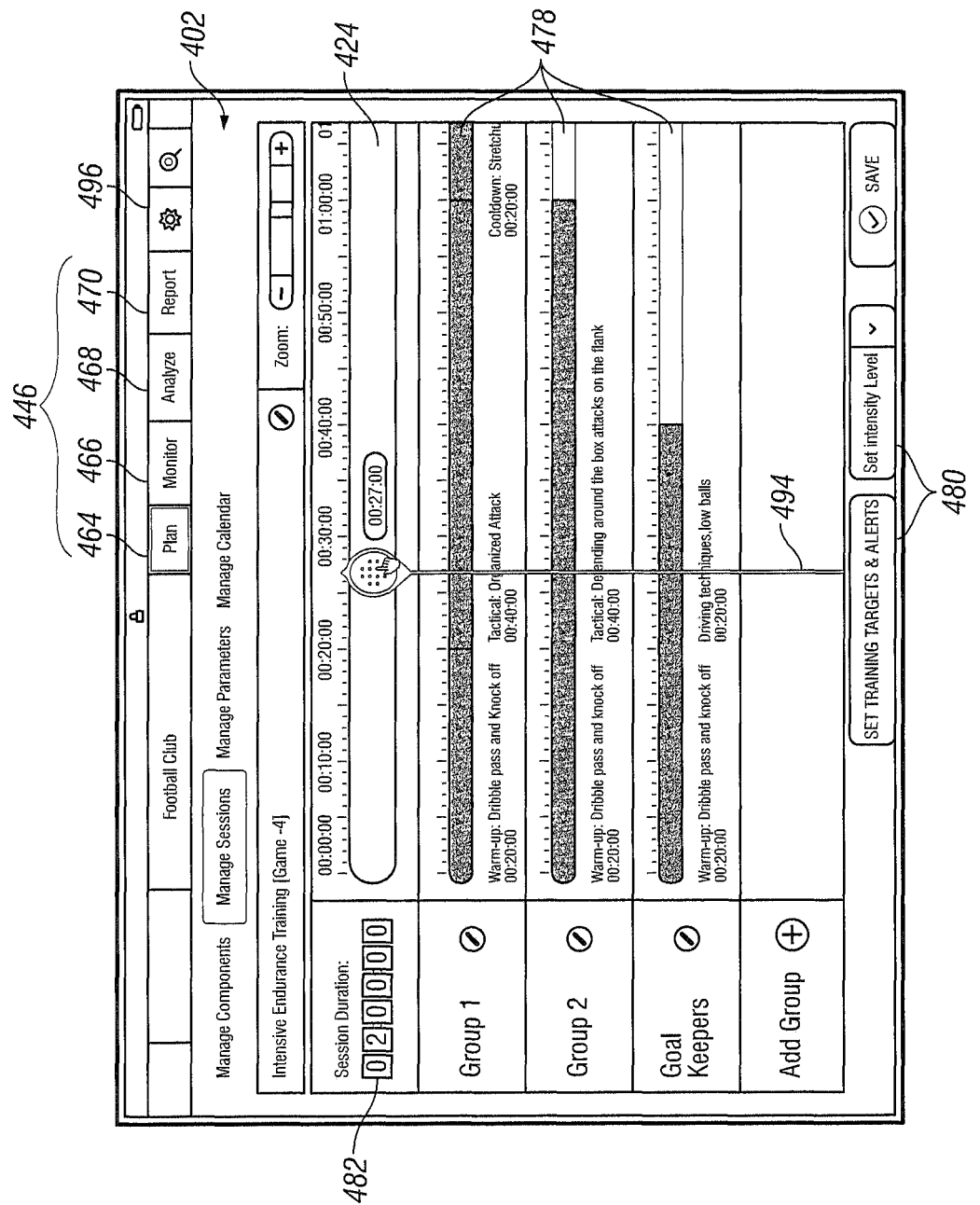
FIG. 46 depicts a display of a group monitoring device according to an exemplary embodiment of the present invention.

In some exemplary embodiments, trainer 20 may input notes about a particular individual 10, group of individuals 10, or team, by, for example, selecting a note field 422 of the individual view dashboard, as shown in, for example, FIGS. 16 and 41. In some exemplary embodiments, note field 422 may indicate the presence of notes, display notes, and/or provide an option or input to create new notes. In some exemplary embodiments, selection of note field 422, or otherwise accessing note adding capability, may cause display 402 to display a create note window 438 where trainer 20 can input a note, as shown in, for example, FIG. 44.

Selecting note field 422 may cause a free-text note entry field to appear, into which trainer 20 can enter text. In some embodiments, selecting note field 422 causes a microphone in group monitoring device 400 to activate and record voice input of trainer 20, allowing trainer 20 to record a voice note. Trainer 20 may input desired information in note field 422, such as, for example, a reminder to closely monitor the heart rate of individual 10, a reminder that individual 10 appears dehydrated, a determination that individual 10 should be congratulated for a good play, or a determination that the team should practice a particular play. In some exemplary embodiments, notes include time information, indicating, for example, the time to which a note pertains, or the time a note was created or modified, which can be useful for a later correlation between recorded data and the notes. Such time information may be entered manually or determined automatically.

In some exemplary embodiments, trainer 20 may select markers 440 to include in a session timeline 424. Such markers 440 may be selected before (e.g., using a plan module, as described further herein), during, or after the athletic activity. Session timeline 424 may keep track of the time elapsed or remaining in a session of athletic activity, or in a subset or interval of the session of athletic activity, and may be represented by, for example, numerical values (e.g., numerical value 450) or a moving point on a line representing total session time, as shown in, for example, FIGS. 13, 16, 19, 20, and 27-44. A marker 440 may be used to identify events within a training session. A trainer 20 may select a marker 440 by, for example, selecting an add marker button 426 (see, e.g., FIGS. 13, 16, 20, and 42A), or by selecting a point on session timeline 424, for example.

Figure 42A:
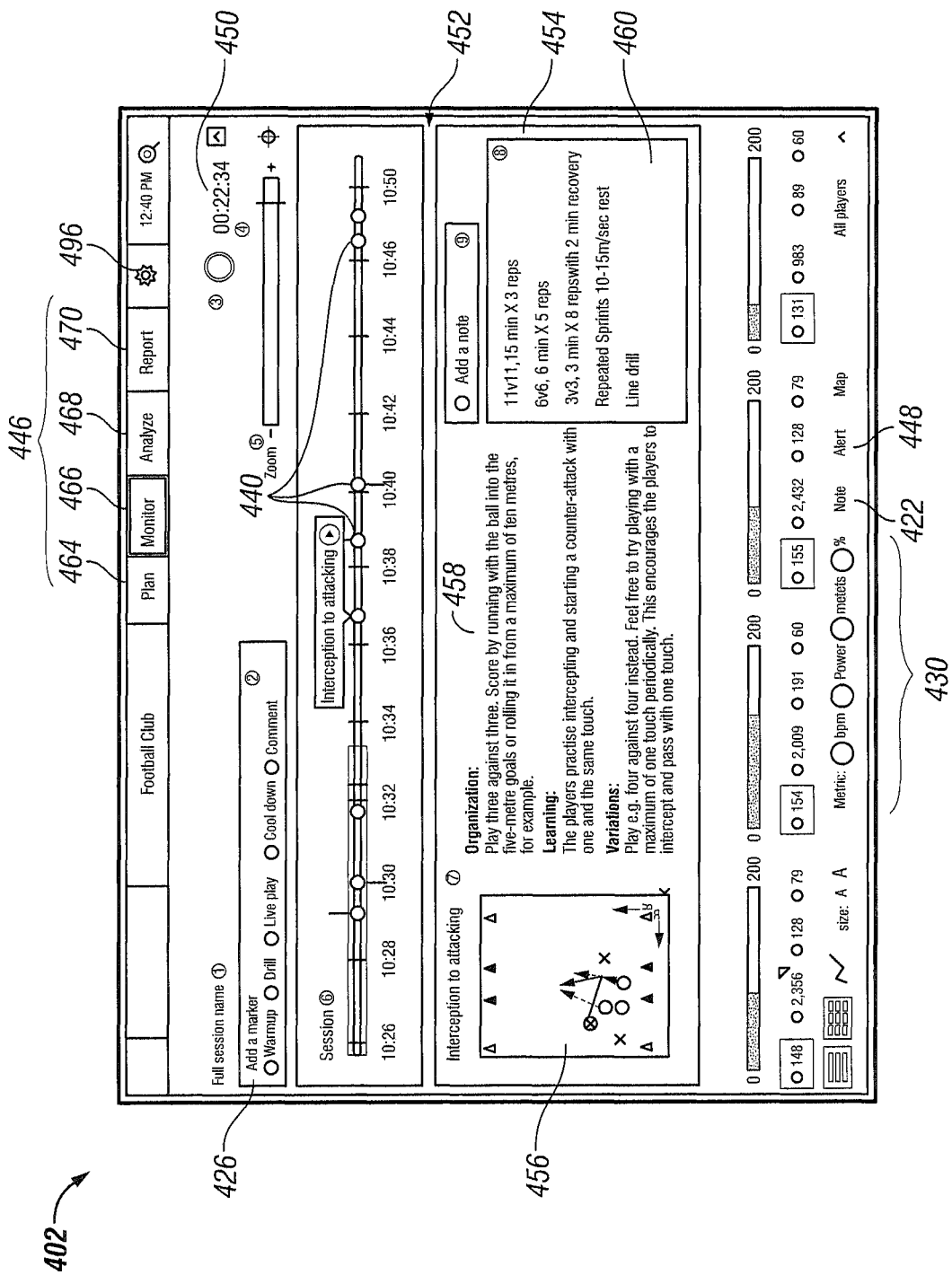
FIG. 42A depicts a display of a group monitoring device according to an exemplary embodiment of the present invention.
Figure 42B:
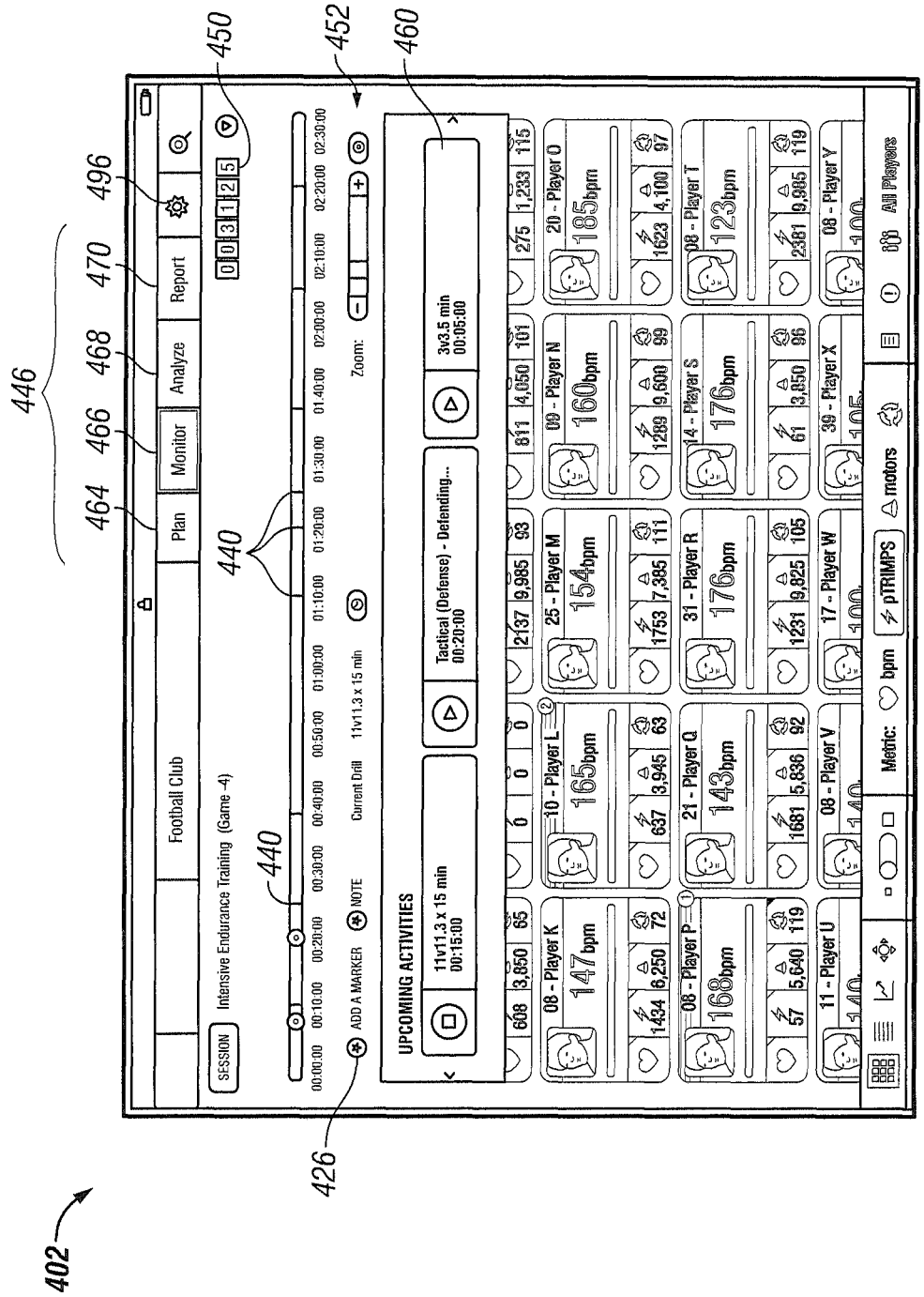
FIG. 42B depicts a display of a group monitoring device according to an exemplary embodiment of the present invention.
Figure 42C:
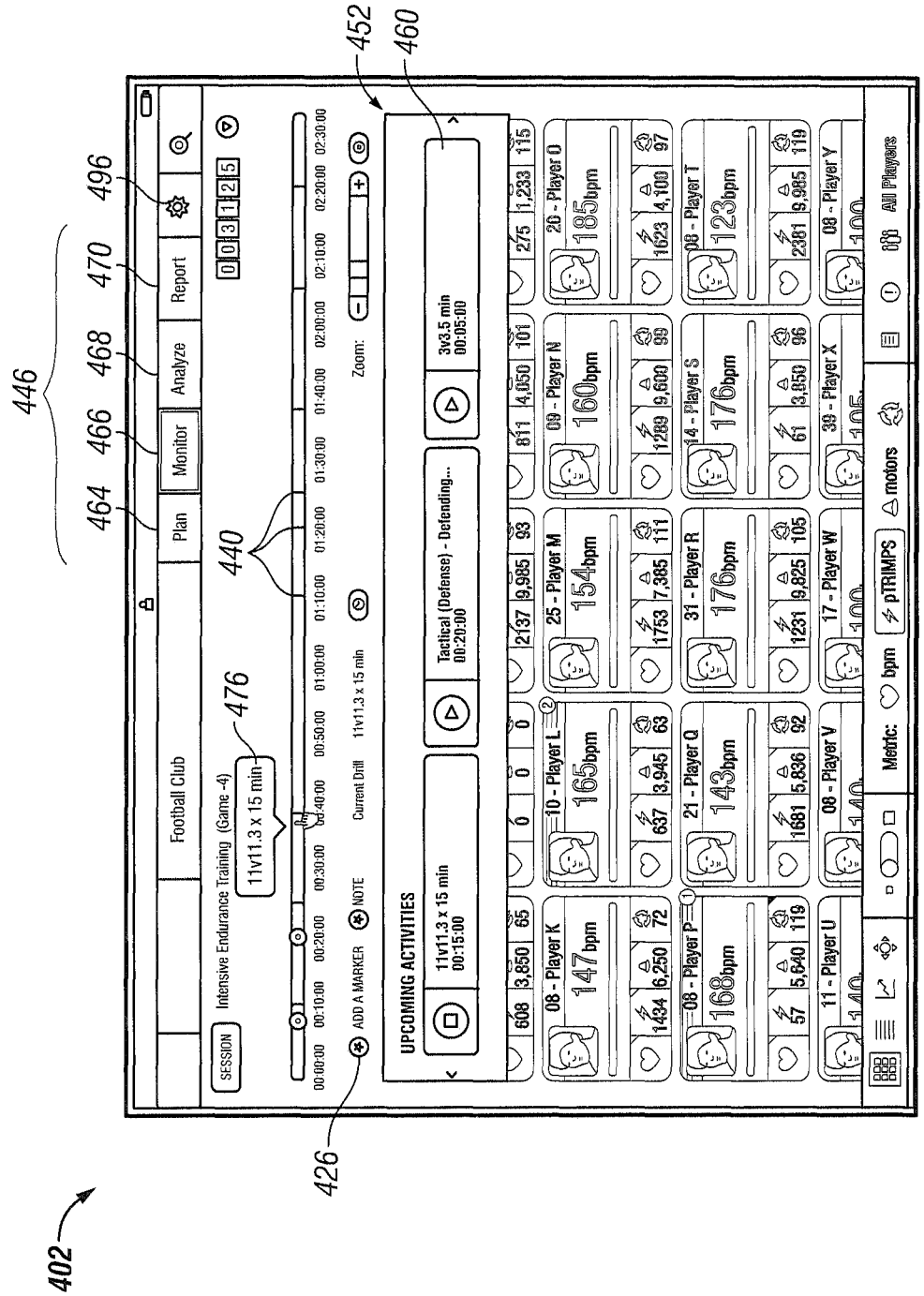
FIG. 42C depicts a display of a group monitoring device according to an exemplary embodiment of the present invention.
Figure 42D:
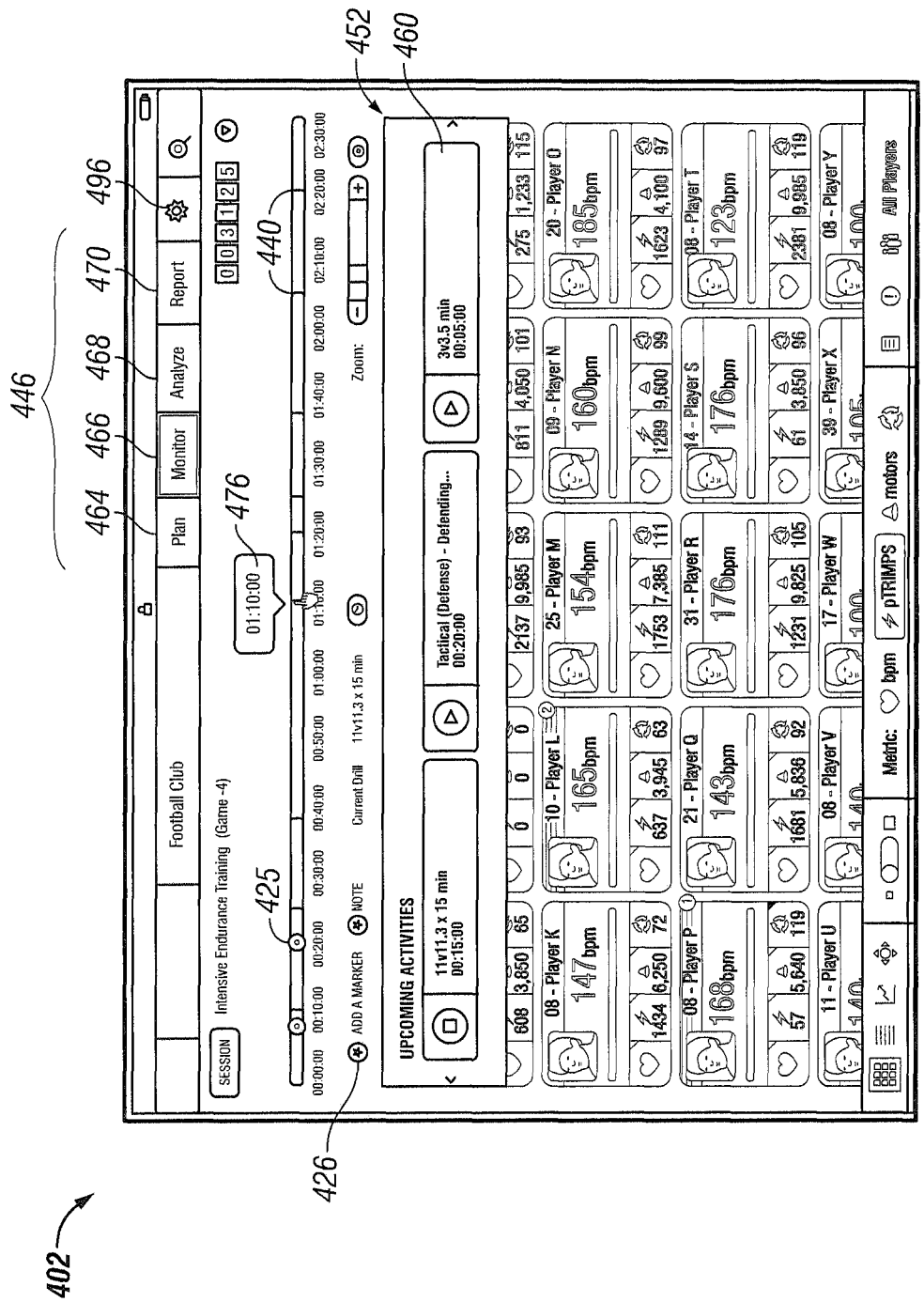
FIG. 42D depicts a display of a group monitoring device according to an exemplary embodiment of the present invention.
Figure 42E:
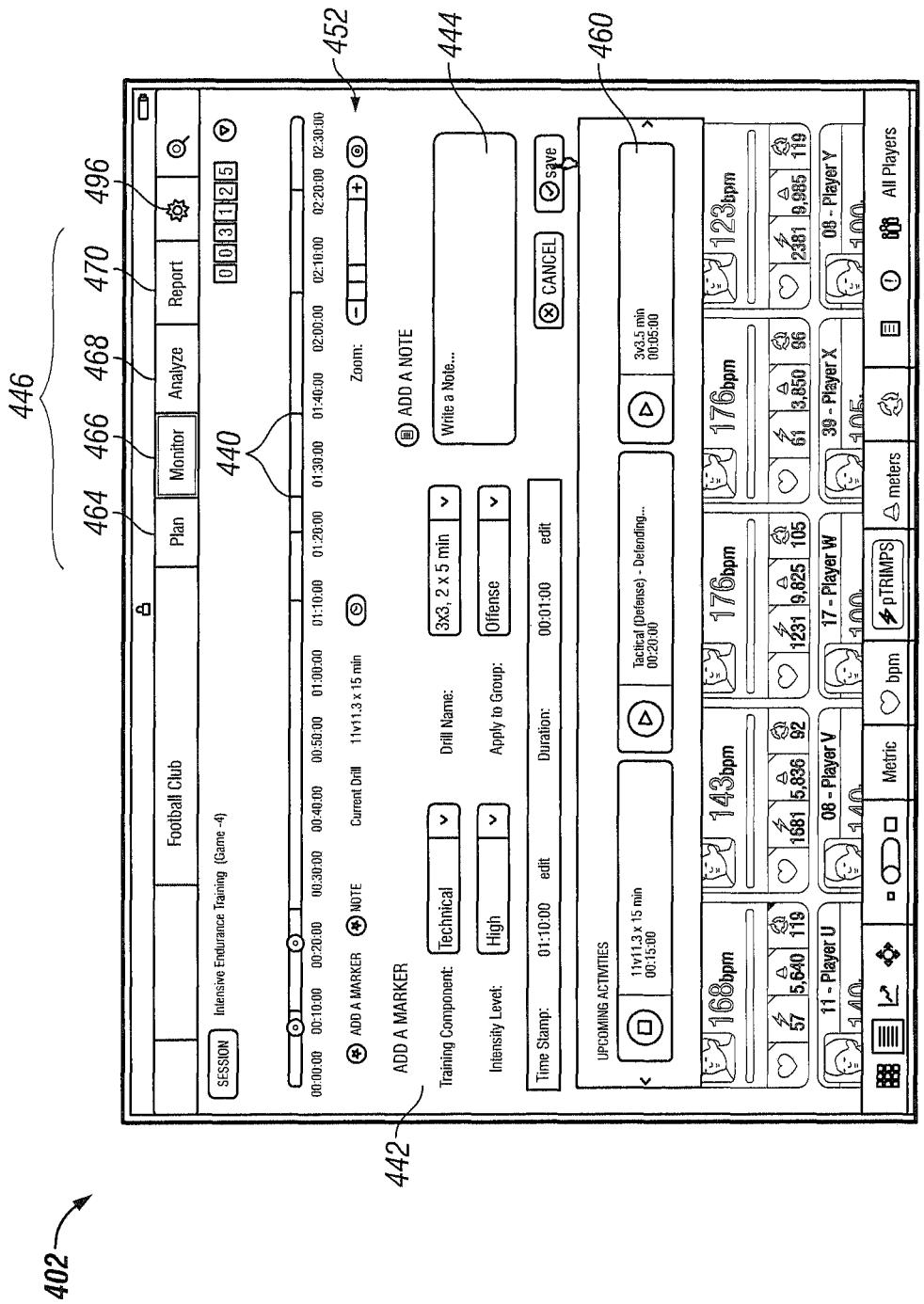
FIG. 42E depicts a display of a group monitoring device according to an exemplary embodiment of the present invention.
Figure 43:
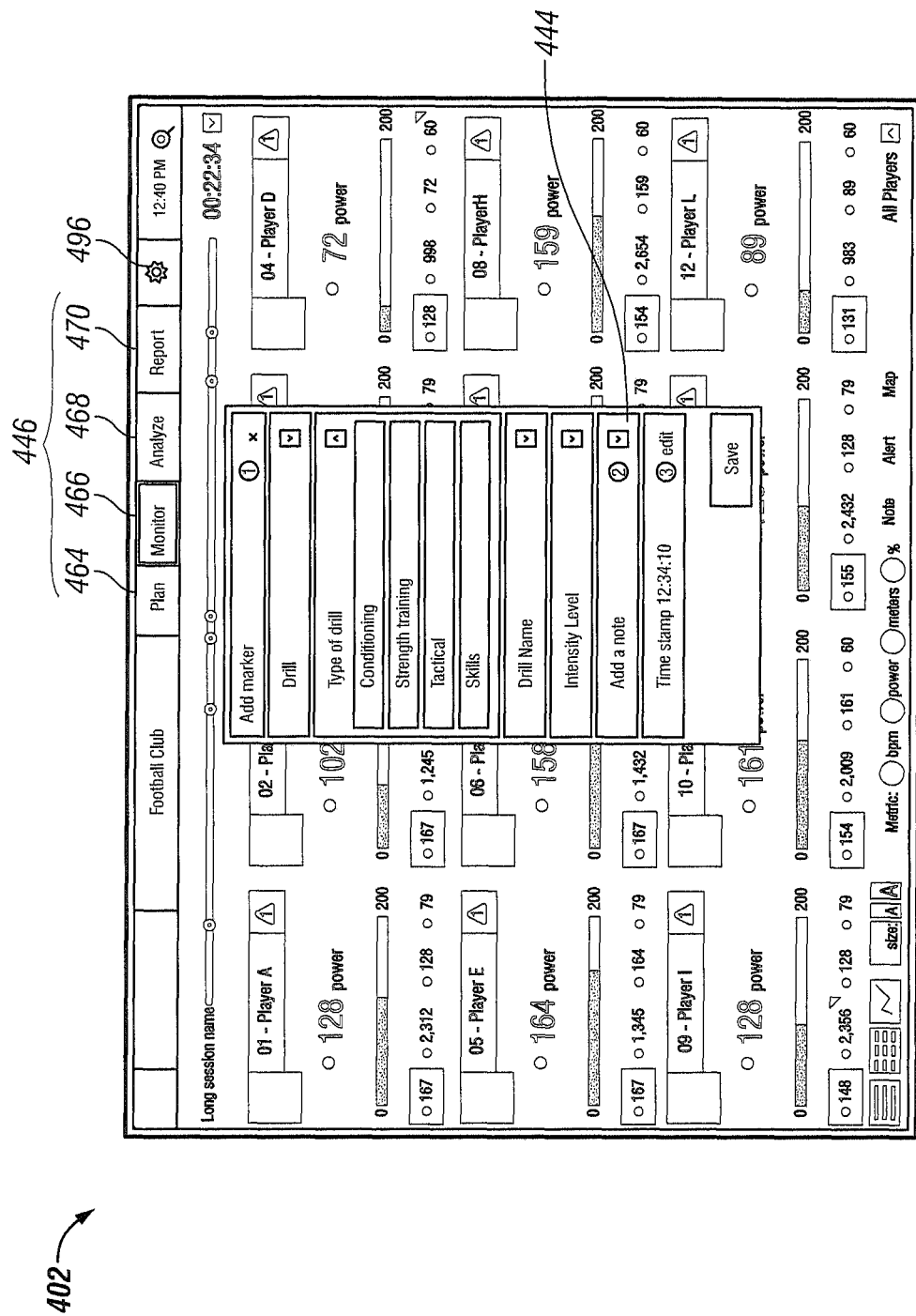
FIG. 43 depicts a display of a group monitoring device according to an exemplary embodiment of the present invention.

In some exemplary embodiments, selection of add marker button 426 causes display 402 to display an add marker window 442, allowing input of parameters to define the marker, as shown in, for example, FIGS. 42E and 43. Add marker window 442 may include a note input area 444 where trainer 20 can input a note associated with a marker 440. A marker 440 may be associated with a team as a whole, with sub-groups of individuals 10, or with a particular individual 10. When selecting a marker 440, trainer 20 may designate the marker type, which can be, for example, an "activity start" marker to designate the point at which an activity starts, an "activity stop" marker to designate the point at which an activity stops, or a "flag marker" to designate the point at which a particular event occurs. For activity-based markers, marker attributes may include the type of activity (e.g., cardio, drill, strength, recovery, other) and the activity name, for example. For flag-based markers, marker attributes may include the type of flag (e.g., injury, rest, off field, out of range).

In some exemplary embodiments, markers 440 include time information, indicating, for example, the time to which a marker 440 pertains, or the time a marker 440 was created and/or modified, which can be useful for a later correlation between recorded data and the markers. Such time information may be entered manually or determined automatically. In some exemplary embodiments, trainer 20 can input notes to be associated with the marker, or with a particular point on session timeline 424. In some exemplary embodiments, as depicted in, for example, FIGS. 27 and 31, note icons 425 positioned at points on session timeline 424 can represent such notes. Attributes of markers 440 may be designated by trainer in real time, or can be pre-defined. Markers 440 can be associated with session timeline 424 at the time they are created, or can be associated with any other time on session timeline 424. Markers can be useful to trainer 20 in analyzing the performance of individuals 10 during the athletic activity as well as after the athletic activity, by associating contextual information with particular times and individuals. In some exemplary embodiments, if a part of a session is marked with activity markers, past data from the same types of activities of an individual 10 can be retrieved and overlaid with more recent (including presently generated) data of the individual 10, thereby facilitating comparison of data for an individual 10. Markers 440 and their use, as described herein, can apply to a particular individual 10, or to groups of individuals 10 (e.g., one or more teams or leagues of individuals 10, or one or more sub-groups of one or more teams or leagues of individuals 10).

In some exemplary embodiments, analysis markers 440 can be defined and manipulated by a user (e.g., trainer 20). Analysis markers 440 can be used as boundaries to define a subset of metric information as a function of an interval parameter. Group monitoring device 400 may then display metric information (e.g., performance metric information, such as, for example, heart rate) corresponding only to the subset of metric information defined by analysis markers 440. Analysis markers 440 can be defined for a particular individual 10, or for a group of individuals 10. An interval parameter may be any parameter that can have a designated first point and second point, which can be designated by, for example, a first analysis marker 440 and a second analysis marker 440, thereby defining an interval therebetween suitable to measure performance. For example, the interval parameter may be time or distance.

In some exemplary embodiments, analysis markers 440 define a portion of the athletic activity engaged in by individuals 10. The portion of athletic activity may be, for example, warmup, a drill, live play, cool down, a line drill, sprints, repeated sprints, a conditioning drill, a strength training drill, a tactical drill, or a skills drill for a particular sport. For example, if a conditioning drill begins 10 minutes into an athletic activity, and ends 15 minutes into the athletic activity, a first analysis marker 440 may designate a time 10 minutes into the athletic activity, and a second analysis marker 440 may designate a time 15 minutes into the athletic activity, thereby defining a 5 minute interval therebetween, corresponding to the conditioning drill.

In some exemplary embodiments, analysis markers 440 may be defined based on past metric information, by manipulating input 404 after the session of athletic activity (e.g., defining an interval in the past). In some exemplary embodiments, analysis markers 440 may be defined based on present metric information, by manipulating input 404 during the session of athletic activity (e.g., defining a beginning point in real time during the athletic activity, and then an ending point in real time). In some exemplary embodiments, analysis markers 440 may be defined based on expected future metric information or expected activity, by manipulating input 404 before the session of athletic activity (e.g., defining expected beginning and ending points in time during a planned session of athletic activity).

When defined based on expected future metric information, group monitoring device 400 can be used to coordinate the planned session of athletic activity, by scheduling intervals of particular athletic activity. For example, analysis markers 440 may define a conditioning drill to take place in the first 5 minutes of athletic activity, a strength training drill in the following 5 minutes, and a skills drill in the following 5 minutes. Group monitoring device 400 may indicate to trainer 20 when an interval is scheduled to begin and end, and when a transition between intervals is scheduled to take place, and trainer 20 may communicate this information to individuals 10. In some exemplary embodiments, base station 300 may send a signal to individual monitors 200 indicating the transition between intervals, or the beginning or end of a particular interval, and individual monitors 200 may communicate this information to individuals 10 via, for example, emitting an audible noise, vibrating, or providing a visual indication (e.g., via an LED or LCD display). In this way, individuals 10 can be alerted as to the start or end of a portion of athletic activity corresponding to a defined interval.

In some exemplary embodiments, to facilitate planning a session of athletic activity, display 402 may display a plan module, which may include utilities useable to plan the session of athletic activity, as depicted in, for example, FIGS. 45-51. Display 402 may include session duration 482, which may be manipulated by a user to define the duration of a session of athletic activity. Display 402 may display a session timeline 424, which may indicate a timeline for a planned session of athletic activity. Trainer 20 may select points and portions of session timeline 424 in order to define intervals of athletic activity scheduled at the selected times. Such intervals of athletic activity may be scheduled for an entire team of individuals 10, for other groups of individuals 10, or for single individuals 10. In an exemplary embodiment, depicted, for example, in FIG. 45, intervals of athletic activity are scheduled for groups of individuals 10, and these groups are displayed with their own timelines 478. In some exemplary embodiments, timelines 478 are aligned with session timeline 424 such that, upon selection of a point on session timeline 424, or upon occurrence of a time corresponding to the point, a line or other indicator 494 extends to corresponding points on timelines 478, as depicted in, for example, FIG. 46.

Various parameters can be defined in association with a planned session of athletic activity and/or the intervals thereof, including, for example, markers, training targets and alerts, as well as intensity levels. In some exemplary embodiments, such parameters can be defined by selection using options and/or menus 480, as depicted in, for example, FIGS. 45-47, selection of which may trigger display of a training target and alert window 486, as depicted in, for example, FIG. 49. Training target and alert window 486 may allow selection of a metric (e.g., heart rate, power, speed), and definition of training or alert zones relative to a percentage of a maximum value for the metric. Training target and alert window 486 may also allow for definition of training or alert zones bounded by definite values of the metric. In some exemplary embodiments, markers 440 defined in association with a planned session of athletic activity may be displayed on session timeline 424 during the session of athletic activity, as depicted in, for example, FIG. 42E. Display 402 may be configured to allow modification, addition, or deletion of such markers 440 by trainer 20 during the session of athletic activity.

Figure 47:
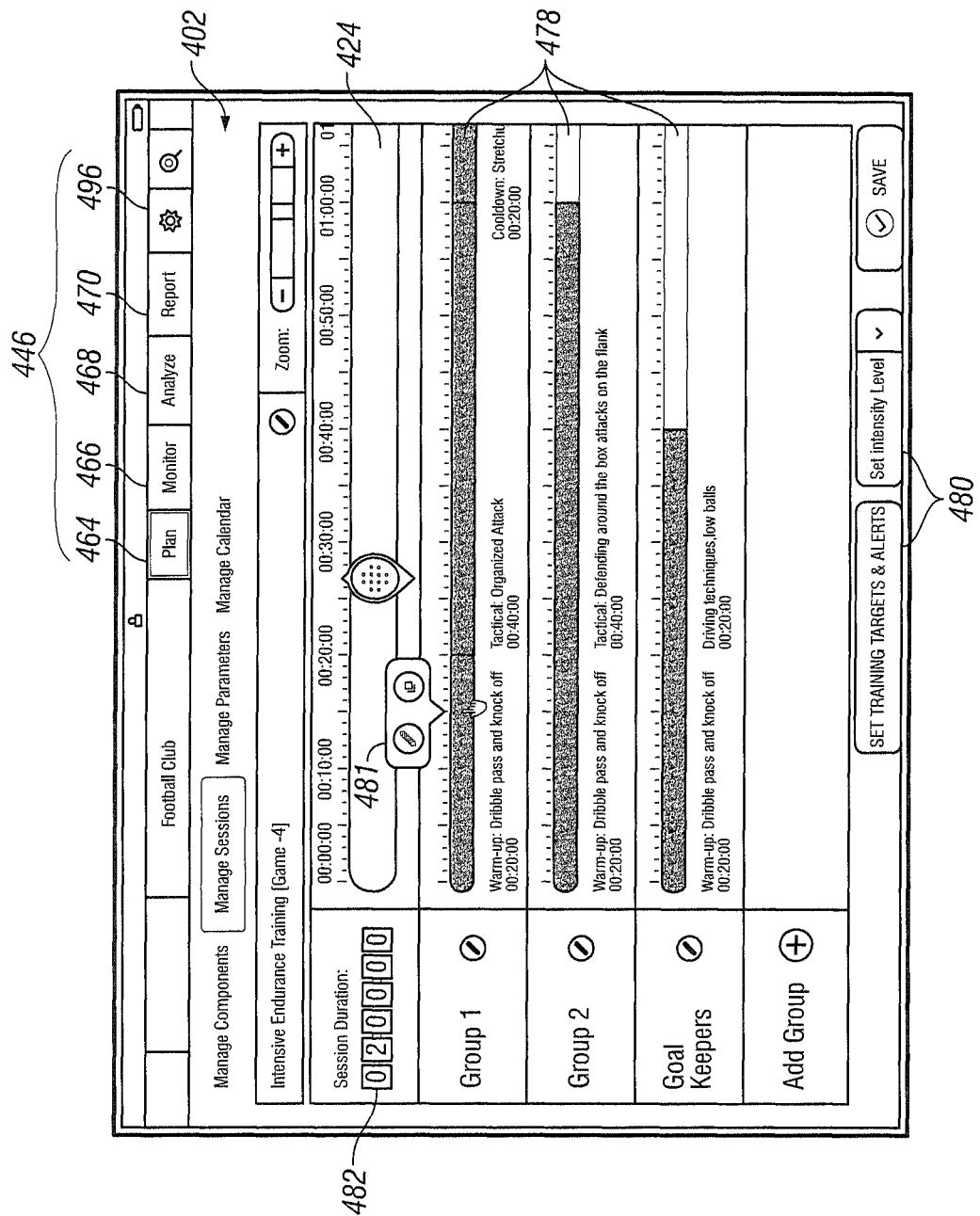
FIG. 47 depicts a display of a group monitoring device according to an exemplary embodiment of the present invention.

In some exemplary embodiments, such parameters (e.g., markers, training targets, alerts, intensity levels) can be defined by selection of a point on timeline 478, as depicted in, for example, FIG. 47. In some exemplary embodiments, such selection of a point on timeline 478 may trigger display of options and/or menus 481 for input of markers, training targets, alerts, and/or intensity levels associated with a point in time or interval corresponding to the selected point. In some exemplary embodiments, such selection of a point on timeline 478 may trigger a window for input of an alert or marker associated with the point in time or interval corresponding to the selected point.

Figure 48:
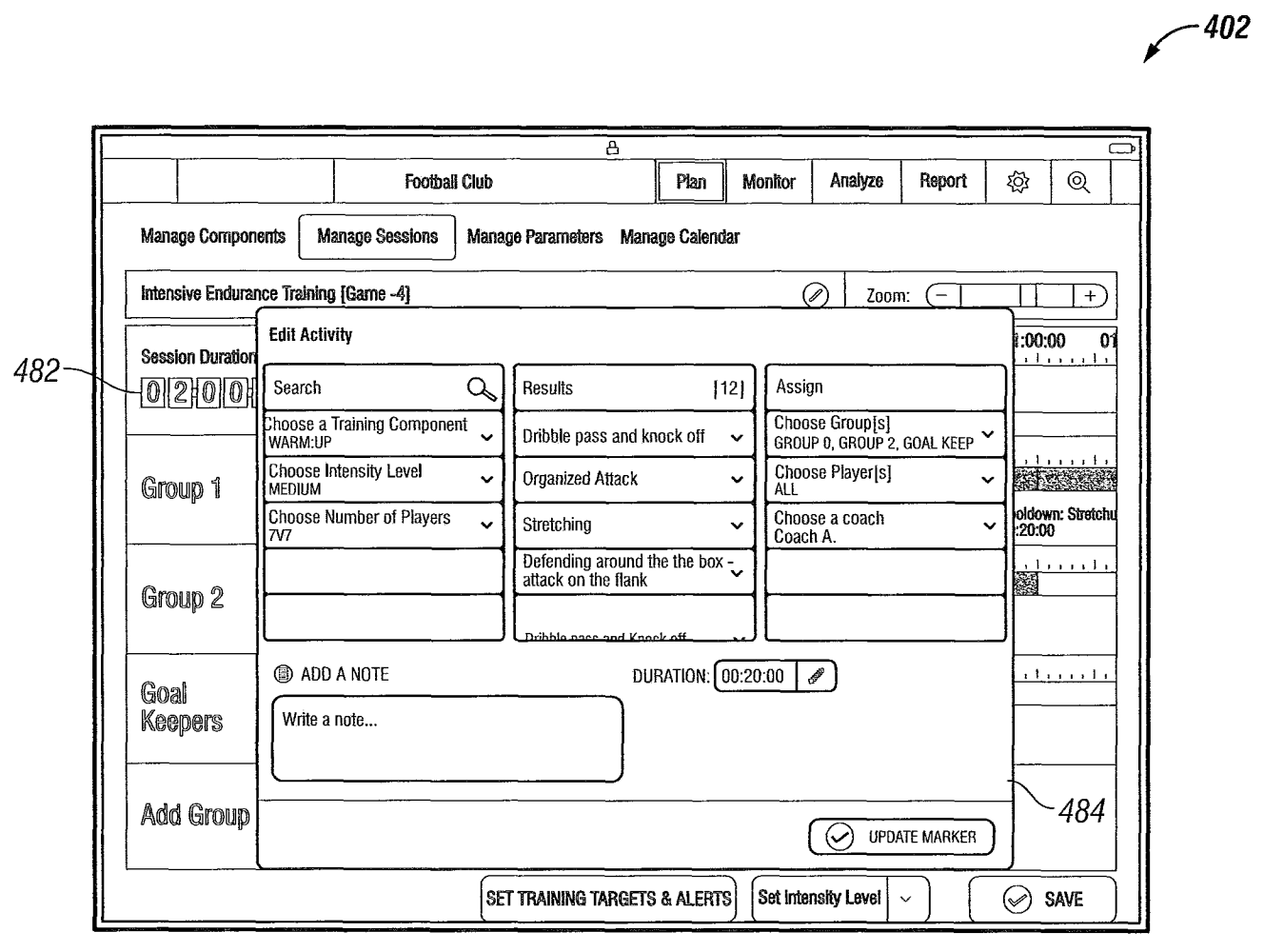

In some exemplary embodiments, as depicted in, for example, FIG. 48, display 402 displays an edit activity window 484, which includes options and inputs facilitating defining of various aspects of an activity associated with an interval of a session of athletic activity. Various activities (e.g., drills, games, tests, training components) may be stored in a database (e.g., base station database 316, or a memory included in group monitoring device 400). Edit activity window 484 may allow a user to search for an activity by choosing a training component (e.g., warm up, drills, competition), choosing an intensity level (e.g., low, medium, high), and choosing the number of players involved. Edit activity window 484 may provide results showing activities matching the input search criteria. Edit activity window 484 may provide an option to assign the resultant activities to individuals 10 or groups thereof, and to choose coaches or trainers 20 to manage the assigned activities. Edit activity window may also allow association of such an activity with a time and duration, thereby scheduling an interval of the session of athletic activity. Such activities may be designated by markers 440, which may be displayed on session timeline 424 during the session of athletic activity, as depicted in, for example, FIG. 42E. Such activities may be designated prior to a session of athletic activity (e.g., using a plan module of group monitoring device 400), during a session of athletic activity, or after a session of athletic activity.

Figure 50:
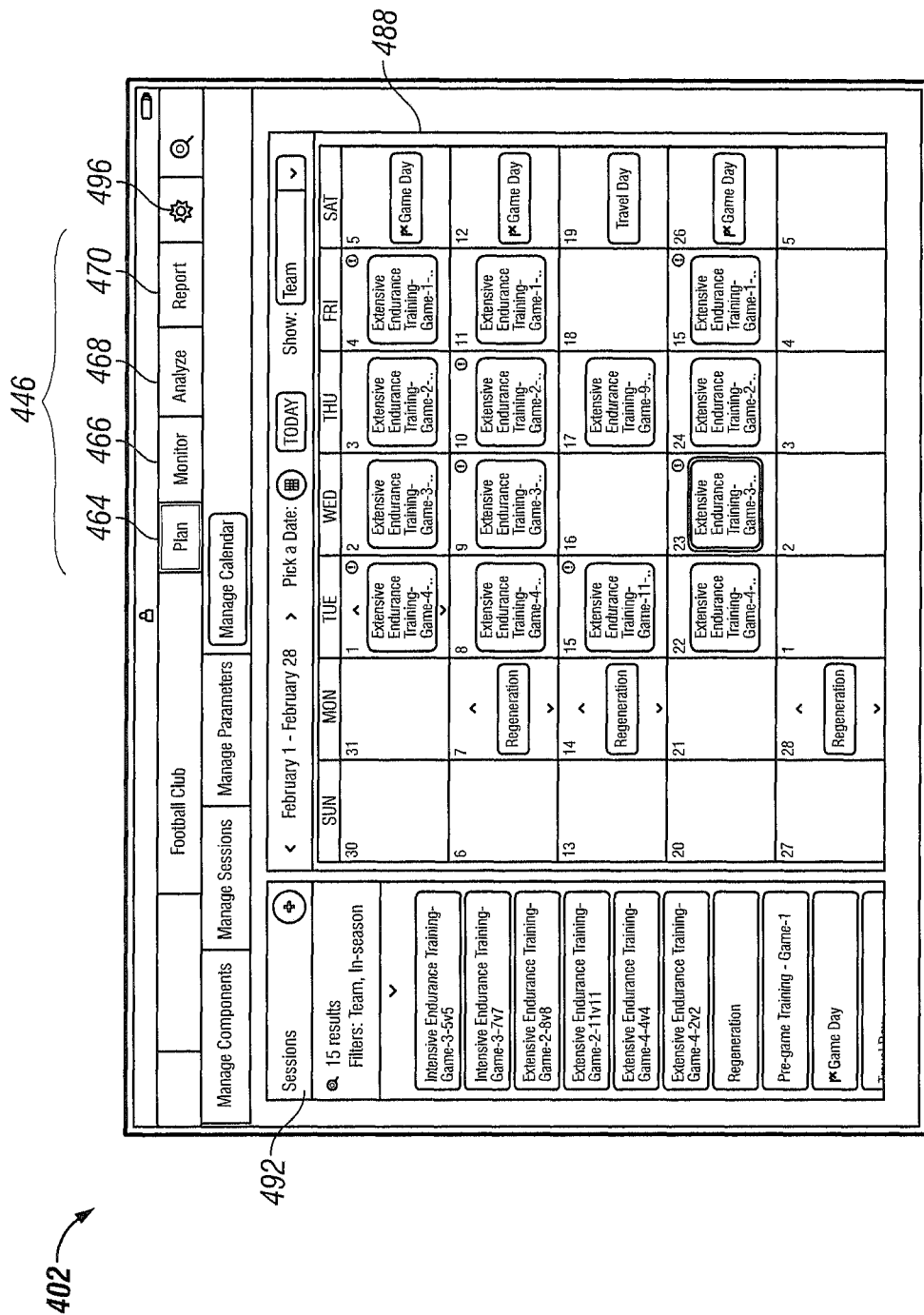
FIG. 50 depicts a display of a group monitoring device according to an exemplary embodiment of the present invention.

In some exemplary embodiments, as depicted in, for example, FIG. 50, display 402 may display a calendar 488 representing sessions of athletic activity and intervals thereof that are scheduled for a set time period (e.g., one week, one month, five days, one day). The displayed time period may be defined by a user. Display 402 may display sessions of athletic activity and intervals thereof scheduled for the past, present, and/or future. In some exemplary embodiments, the types of sessions of athletic activity and intervals thereof displayed may be filtered according to criteria input or selected by a user.

Figure 51:
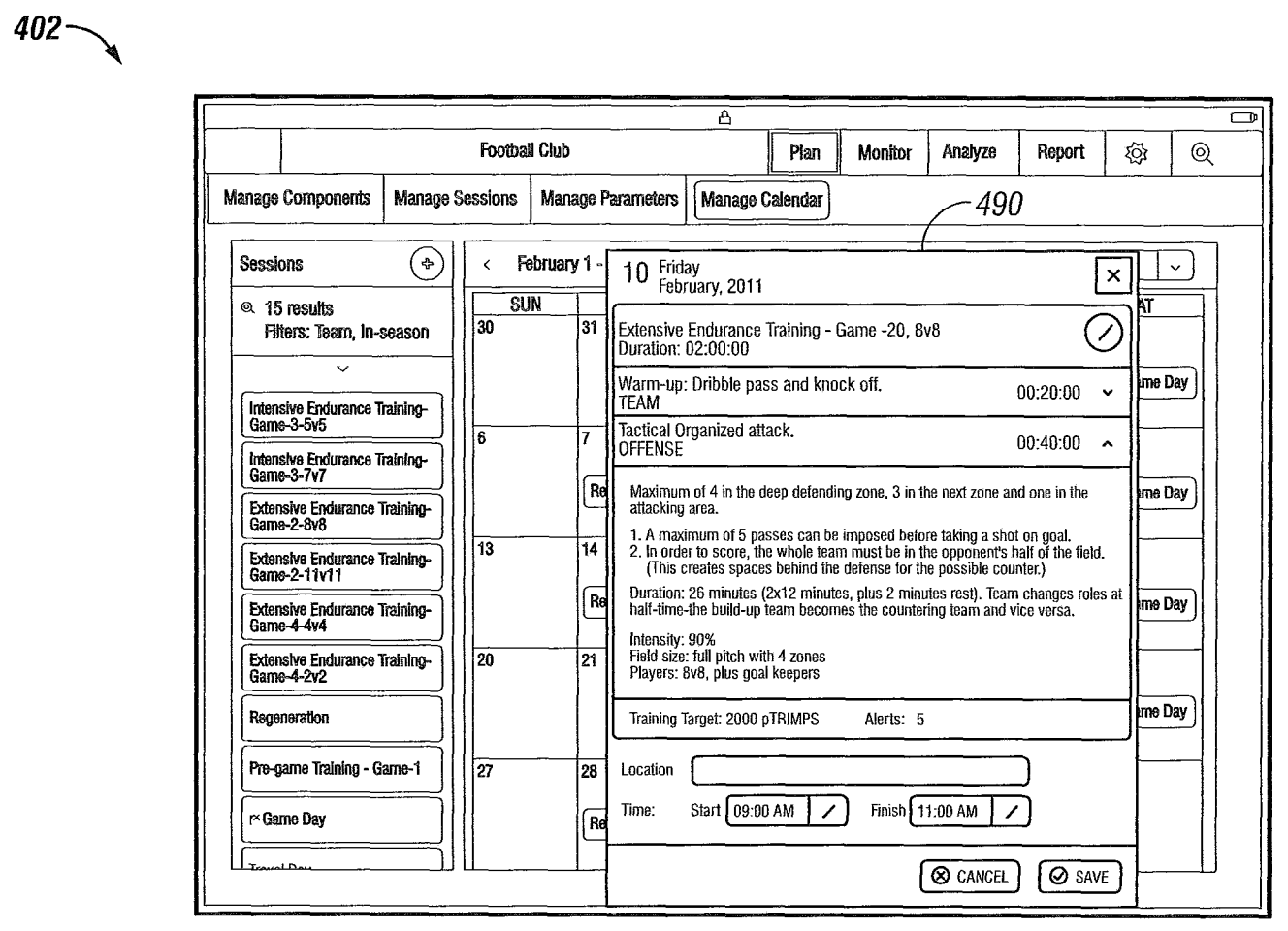

In some exemplary embodiments, as depicted in, for example, FIG. 51, selection of a particular time period displayed in calendar 488 (e.g., a particular day), may trigger display of a detailed view of scheduled events for the selected time period. For example, a detailed schedule window 490 may display an overall session of athletic activity scheduled for the selected time period, as well as intervals of the session of athletic activity and their characteristics (e.g., type of interval, applicability of interval to particular groups or individuals 10, beginning and end times of interval, description of activities to be performed during interval, location of interval).

Figure 52:
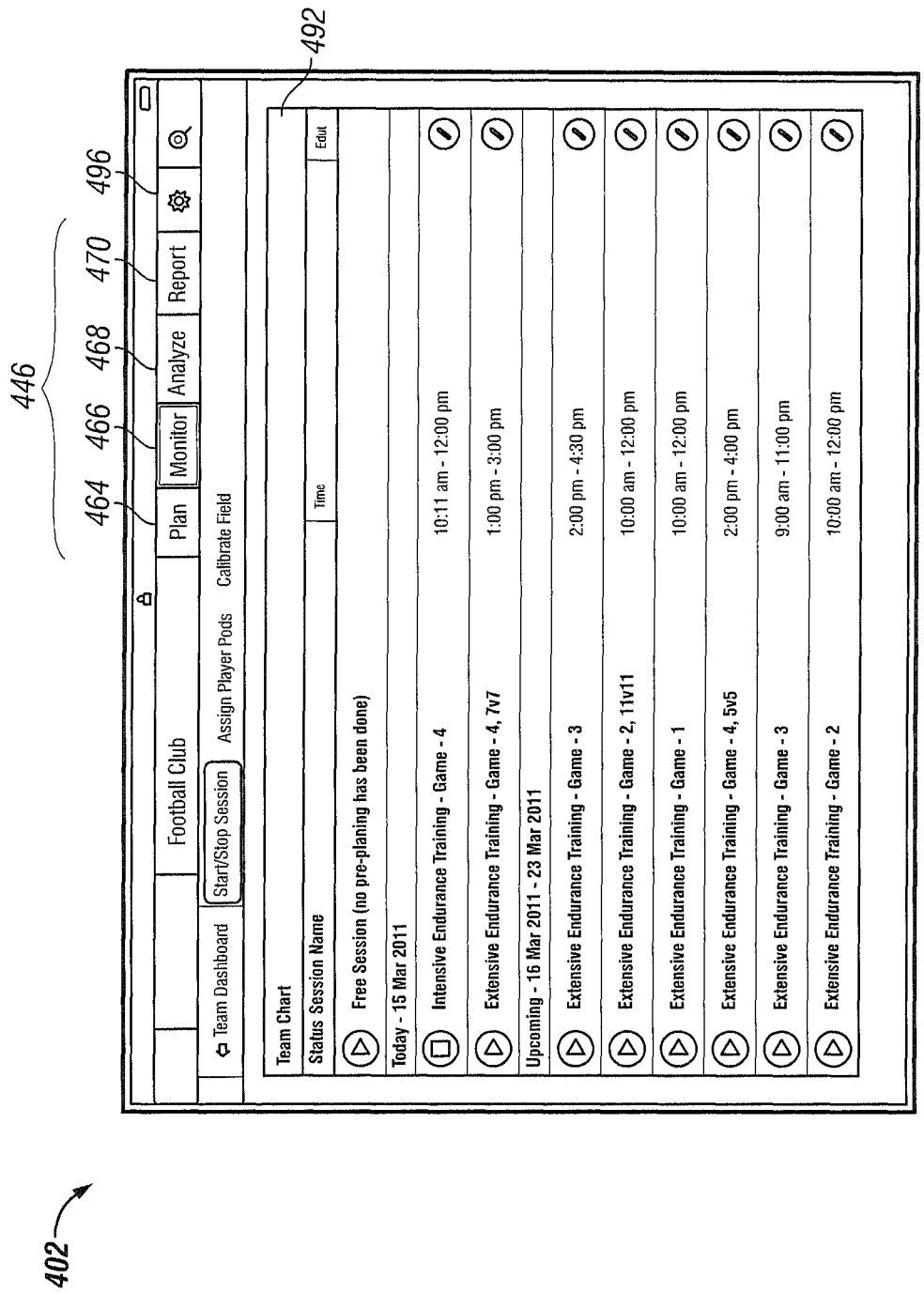
FIG. 52 depicts a display of a group monitoring device according to an exemplary embodiment of the present invention.

In some exemplary embodiments, as depicted in, for example, FIG. 52, display 402 displays a session list 492, which may depict a list of scheduled sessions of athletic activity, as well as intervals of athletic activity associated therewith. Session list 492 may display sessions of athletic activity scheduled for times that have passed, scheduled for the present (e.g., the present time or day), and scheduled for the future.

In some exemplary embodiments, display 402 may display a session control monitor 452, which may provide information relating to a past, ongoing, or future session of athletic activity, as depicted in, for example, FIGS. 42A and 42B. When used during a session of athletic activity, session control monitor 452 may help trainer 20 facilitate the session, by, in addition to providing information about individuals 10, by providing a session information feature 454, as depicted in, for example, Figures and 42A and 42F. Session information feature 454 may provide information about, for example, a present interval of athletic activity. In some exemplary embodiments, session information feature 454 may include a diagram 456 depicting intended movement of individuals 10 during, for example, a particular play or other strategic action. In some exemplary embodiments, session information feature 454 may include description 458 of, for example, a particular play or other strategic action. In some exemplary embodiments, session information feature 454 may include a schedule 460 of, for example, past and/or upcoming intervals of athletic activity.

Figure 42F:
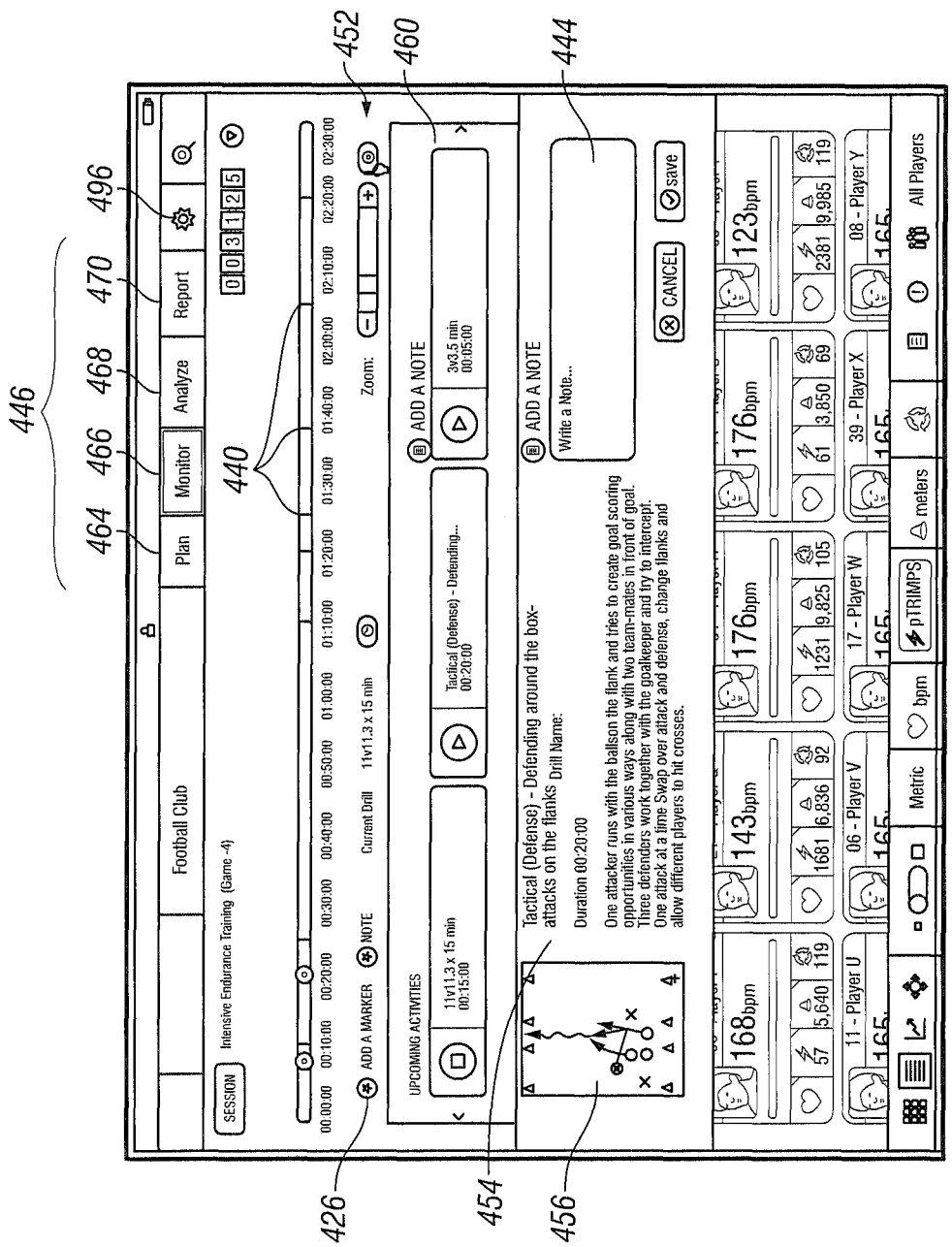
FIG. 42F depicts a display of a group monitoring device according to an exemplary embodiment of the present invention.

In some exemplary embodiments, selection of an entry in schedule 460 may trigger display of a session information feature 454 related to that entry, as depicted in, for example, FIG. 42F. Session timeline 424 may include information displayed in schedule 460, such that selection of a point on session timeline may trigger display of information relevant to that point in the session (e.g., time selected, interval of athletic activity scheduled for time selected). Such information may be displayed in, for example, a timeline information window 476, as depicted in, for example, FIGS. 42C and 42D. This information can be useful to trainer 20 to facilitate an ongoing session of athletic activity, and can be defined in advance of the session of athletic activity. In some exemplary embodiments, information in session information feature 454 can be defined after, and applied to, a past session of athletic activity, and can be used, for example, to help trainer 20 analyze the past session.

Figure 54:
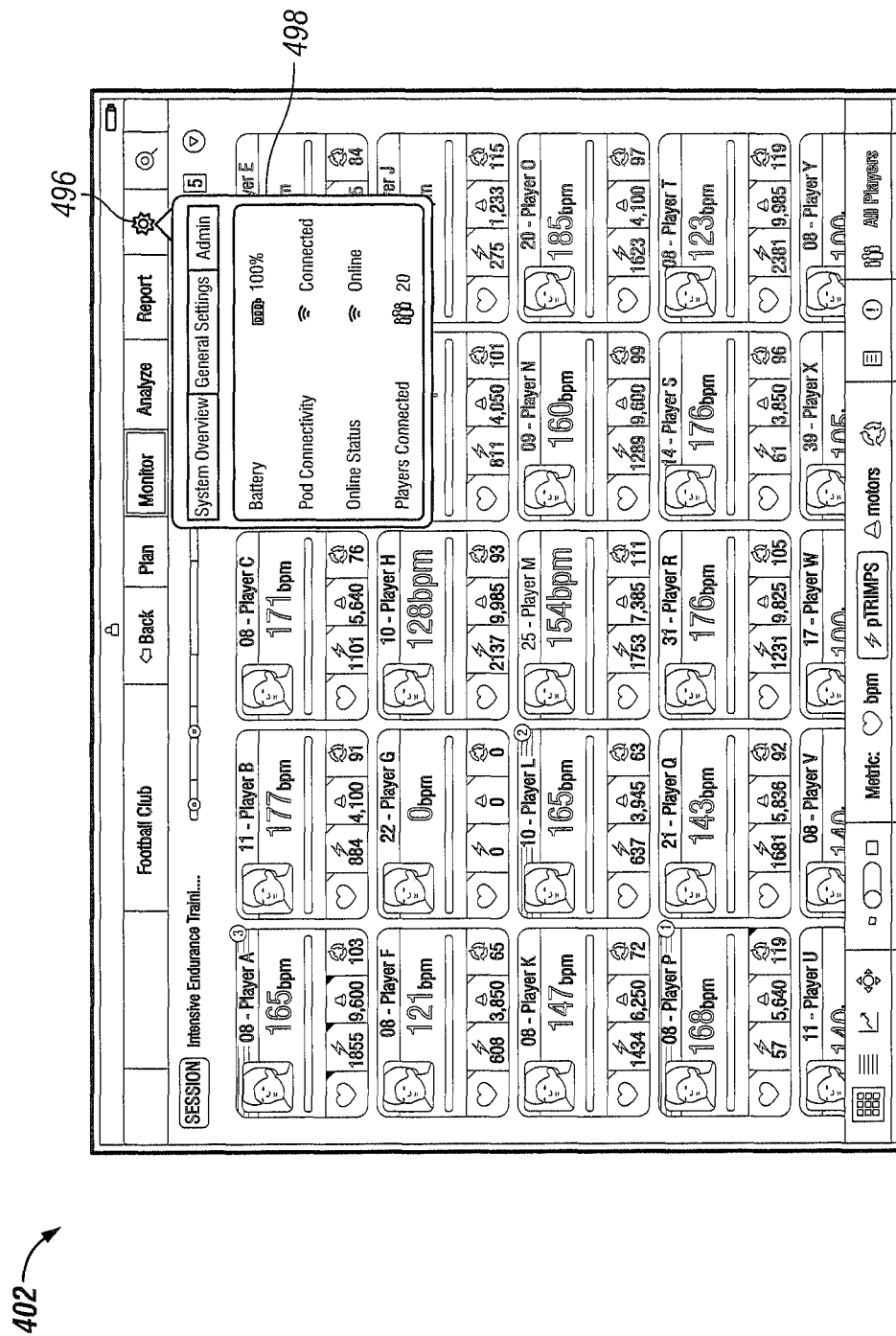
FIG. 54 depicts a display of a group monitoring device according to an exemplary embodiment of the present invention.

In some exemplary embodiments, as depicted in, for example, FIG. 54, display 402 includes a status icon 496 that, when selected, triggers display of a status menu 498. Status menu 498 may display information about the statuses of various components of group monitoring system 100. Status menu 498 may include information about, for example, the battery life remaining in group monitoring device 400 or base station 300, the connectivity and/or signal strength between group monitoring device 400 and base station 300, the connectivity and/or signal strength between group monitoring device 400 and the Internet or other network, and the number of individuals connected to base station 300.

Figure 12:
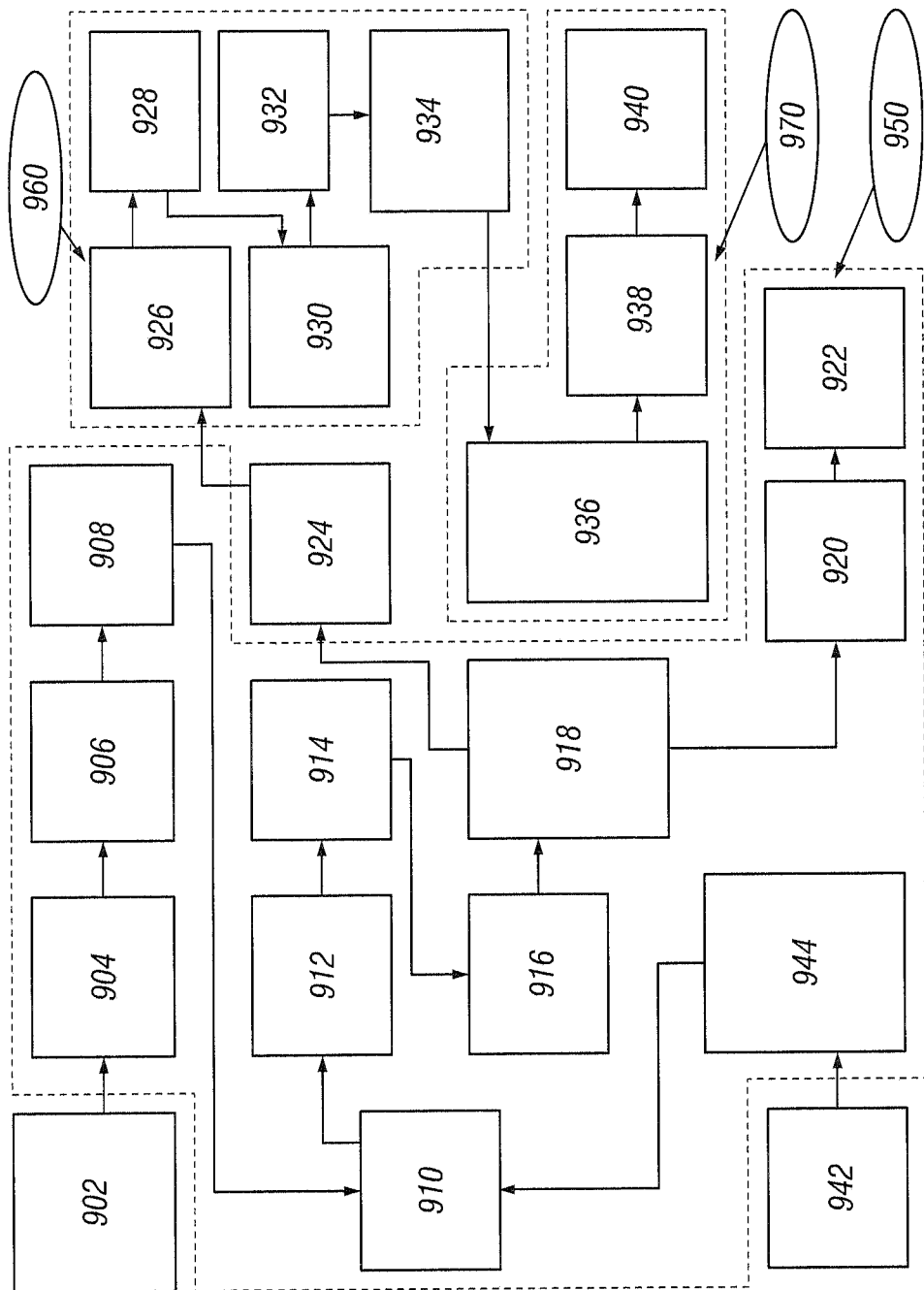
FIG. 12 depicts a monitoring flow diagram according to an exemplary embodiment of the present invention.

Exemplary embodiments of the present invention may include data flows such as that shown in FIG. 12, which depicts a data flow including a real-time monitoring flow 950, a post-session data integrity flow 960, and a post-session analysis flow 970. At box 902 of FIG. 12, data processing module 304 of base station 300 assigns encryption keys to each individual monitor 200 (also referred to as a "player pod"), and each individual monitor 200 is connected to sensors 202. At box 904, sensors 202 determine raw data indicative of characteristics of a monitored individual 10 (data indicative of, e.g., physiological characteristics, performance characteristics, position characteristics, and/or orientation characteristics). At box 906, sensors 202 send the raw data to individual monitor 200 via a wired or wireless connection. At box 908, individual monitor 200 transmits the data to data reception module 302 of base station 300 via a wireless connection, in real time. At box 942, cameras (e.g., camera monitoring system 700, video feed camera 804) determine image data. At box 944, the cameras send the image data to data reception module 302 of base station 300.

At box 910, data reception module 302 of base station 300 writes the data to a file. At box 912, data reception module 302 of base station 300 sends the file to data processing module 304 of base station 300. At box 914, data processing module 304 of base station 300 validates and decrypts the data. At box 916, data processing module 304 of base station 300 stores the decrypted data in base station database 316. At box 918, logic module 312 of base station 300 accesses the decrypted data and, using algorithms, determines metrics and alerts. At box 920, logic module 312 of base station 300 sends the metrics to web server 314 of base station 300. At box 922, web server 314 of base station 300 sends the metrics to live monitoring devices 400.

At box 924, logic module 312 of base station 300 stores the metrics and alerts in base station database 316. At box 926 individual monitors 200 are connected to base station 300 via a wired connection and upload data to data reception module 302 of base station 300. At box 928, data reception module 302 of base station 300 writes the data to a file. At box 930, data reception module 302 of base station 300 sends the file to data processing module 304 of base station 300. At box 932, data processing module 304 of base station 300 validates and decrypts the data. At box 934, data processing module 304 of base station 300 performs data filtering (e.g., data de-duplication) if necessary, and stores the decrypted data in base station database 316. At box 936, central sync module 310 of base station 300 accesses and sends decrypted data, metrics, and alerts ("session data") to web server system 500. At box 930, web server system 500 stores the session data in web server database 502 of web server system 500. At box 940, web server system 500 sends the session data to analysis devices 600.

Group monitoring system 100 can include any suitable number of components such as individual monitors 200, base stations 300, group monitoring devices 400, or analysis devices 600. In an exemplary embodiment, group monitoring system includes 30 individual monitors 200, 1 base station 300, and 2 group monitoring devices 400.

After completion of a session of athletic activity, individuals 10 may dock their individual monitors 200 in one of docking ports 318 of base station 300. When docked with docking port 318, batteries 212 of individual monitors 200 can be charged, and data can be transferred from individual monitors 200 to base station 300. As noted above, individual monitors 200 store sensed data and also transfer sensed data wirelessly to base station 300 during an athletic activity. In order to most efficiently use bandwidth, data may be transferred wirelessly during the athletic activity at a lower resolution than it is sensed and stored in individual monitors 200. Due to communication errors, some data may not be transmitted successfully from individual monitors 200 to base station 300 (e.g., if an individual moves out of range of base station 300). Thus, the data stored in individual monitors 200 at the conclusion of a session of athletic activity may be more complete or accurate than the data stored in base station database 316.

In some exemplary embodiments, data can be transferred from individual monitor 200 to base station 300 at full resolution (i.e., raw data) and stored in base station database 316 (and/or web server database 502, once transferred thereto) at full resolution as well. Storing such raw data for each individual 10 for each session may be useful for subsequent data analysis, for example to perform recalculations of metrics or calculations of new and different metrics using new and different algorithms.

In some exemplary embodiments, data and metrics can be stored in a general database (e.g., a database shared by several of the systems described herein, or a general sports database for individuals).

While docked in docking ports 318 of base station 300, individual monitors 200 can directly transmit their stored data to data processing module 304 (via data reception module 302). Data processing module 304 can then filter the data received from individual monitors (e.g., data processing module 304 can perform a de-duplication process on the data to avoid storing duplicate data in base station database 316) and store the data in base station database 316.

In some exemplary embodiments, base station 300 includes a central sync module 310. Central sync module 310 of base station 300 can communicate through an Internet connection with a web server system 500, web server system 500 being external to base station 300. If base station 300 is connected to the Internet via an Ethernet (or other wired) connection, such communication can take place over the Ethernet (or other wired) connection. If base station 300 is not connected to the Internet via an Ethernet (or other wired) connection, communication can take place wirelessly, for example over a cellular network (e.g., GSM broad band 2.5G or 3G). Central sync module 310 includes data upload and download capabilities for uploading session data about a monitored athletic activity, or diagnostic information about base station 300 and other components, and to download user data such as, for example, updated firmware to be installed in individual monitors 200 via docking port 240, or updated software for use in base station 300. Central sync module 310 can upload data stored in base station database 316 to web server system 500. Such data may include data, metrics, and alerts generated during the athletic activity. When receiving such data, web server system may store it in a web server database 502.

Web server system 500 can render display code (such as, for example, html5 compliant code) based on a request from a client device such as, for example, analysis device 600. Web server system 500 can also serve a security function, by ensuring that a requesting client device is properly authenticated and that all data is passed using https. Web server system 500 may provide analysis device 600 with requested metrics and generated alerts stored in web server database 502, via, for example, an API layer.

Figure 10:
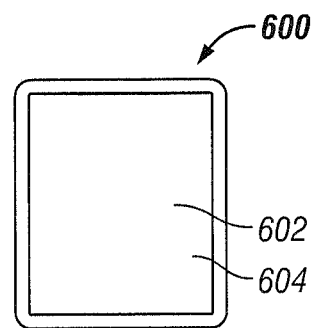
FIG. 10 depicts an analysis device according to an exemplary embodiment of the present invention.

Analysis device 600 is depicted in FIG. 10 and includes a display 502 and an input 504. In an exemplary embodiment, analysis device 600 is a tablet computing-style device (such as a tablet personal computer or an iPad, marketed by Apple Inc.®). Analysis device 600 may be, however, any other suitable device, such as, for example, a laptop computer, a smartphone, or a personal computer. Analysis device 600 can access data in web server database 502 and display the information to a user of analysis device 600 (e.g., trainer 20). Although analysis device 600 and group monitoring device 400 are described separately herein, in some exemplary embodiments, group monitoring device 400 and analysis device 600 are the same device.

In some exemplary embodiments, analysis device 600 can be located at a remote location with respect to base station 300 or the relevant athletic activity, and can be used to access and display data and metrics in real time. In such an embodiment, base station 300 can transfer the data and metrics to web server 500 in real time, so that the data and metrics can be accessed for display by analysis device 600, as described above. Such an embodiment may be useful for a user to monitor an ongoing session of athletic activity from a remote location (e.g., a trainer 20 that could not be present at a match, or a team owner that desires to monitor a training session without physically attending the session).

After completion of a session of athletic activity, a trainer 20 may use analysis device 600 to review and analyze information about individuals 10, including information about past performances of individuals 10 during past sessions of athletic activity. Depending on the number of past sessions of athletic activity for which data is available in web server database 502, post-session analysis of an individual 10 using analysis device 600 may provide trainer 20 with information spanning a longer period than the information provided during an athletic activity by group monitoring device 400. Trainer 20 may access and view the data using analysis device 600, however, in much the same way as has been described above with respect to group monitoring device 400. For example, analysis device 600 may be configured to display a team view dashboard, and an individual view dashboard, as described above with reference to group monitoring device 400. Some differences applicable to some exemplary embodiments of team view dashboard and individual view dashboard of analysis device 600 include that the displayed information may not be updated in real time when using analysis device 600, that the information displayed may span multiple sessions of athletic activity, and that alerts can be created that apply to data across multiple sessions.

Moreover, the team view dashboard and individual view dashboard of analysis device 600 may be customizable. Display components (e.g., photograph 410 of individual 10, list of all individuals 10, location component 412 showing a map of positions of individuals 10 on playing field, detailed charts and/or graphs 418) can be added or removed by trainer 20 so as to create a customized view dashboard, which can be saved and referred to in the future. In some embodiments, customized view dashboards can be sent to or otherwise used by group monitoring devices 400, thereby allowing trainer 20 to view real-time data in a custom format.

In some exemplary embodiments, analysis device 600 includes an analysis chart view that displays a detailed view of a metric, in for example, a chart format or a graph format. Trainer 20 may input desired parameters for the analysis chart view via input 602. For example, trainer 20 may input parameters indicating that the analysis chart view should be generated to show data for all drills performed by Player A during August 2010. Alternatively, analysis device 600 may show trainer 20 a list of all data entries corresponding to the parameters input by trainer 20, allowing trainer 20 to select the entries desired to be included in an analysis chart view. Trainer 20 may also be given the option to select a type of analysis chart view. For example, trainer 20 may be able to choose from a stacked view, where several charts or graphs, each pertaining to a different metric, are stacked one above the other; or an overlay view, where multiple metrics are displayed on a single chart or graph. In some exemplary embodiments, the overlay view allows trainer 20 to view data from one time period (e.g., current data or most recent data) overlaid with data from another time period (e.g., older data) to allow easy comparison of performance at different times.

Figure 55:
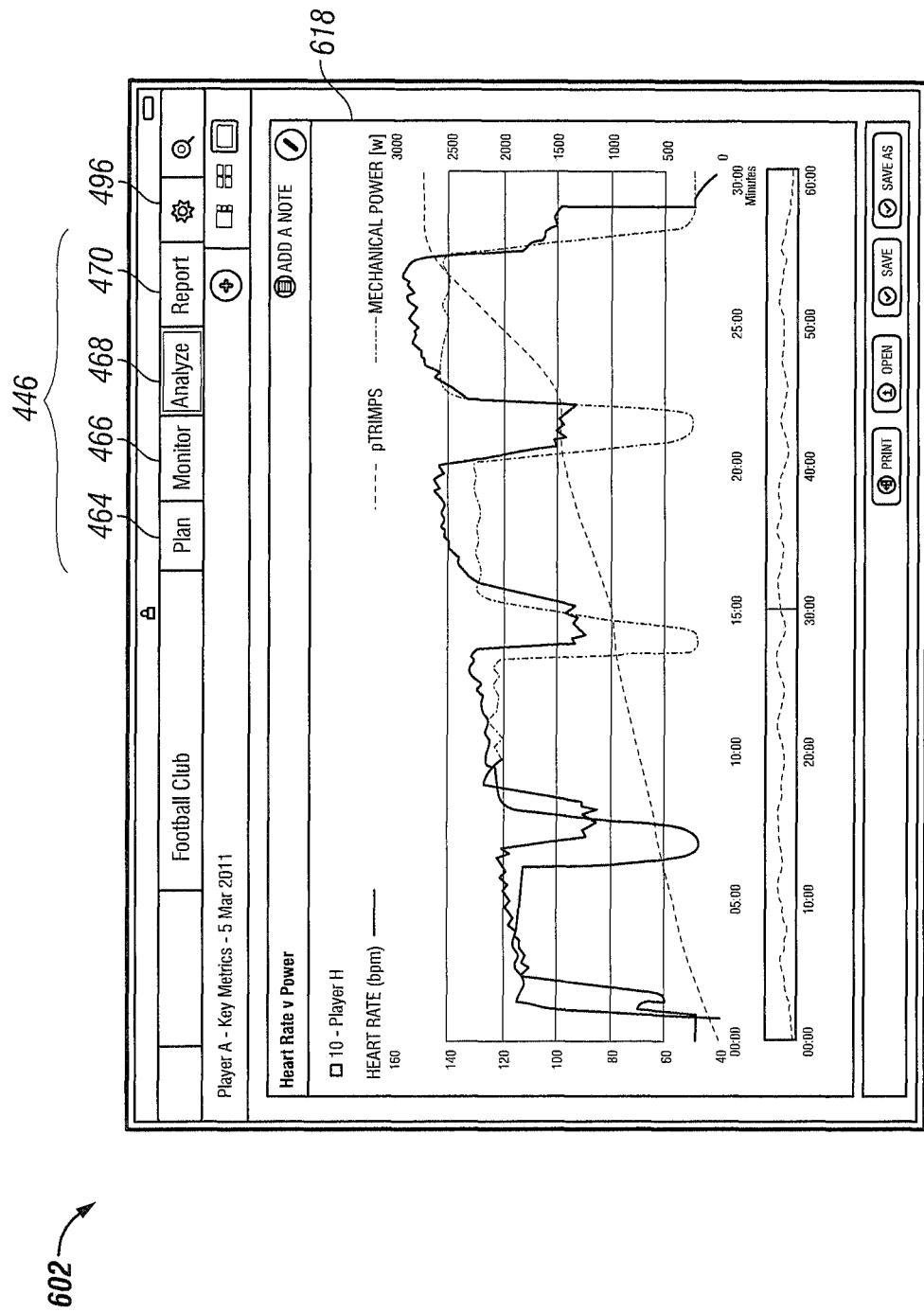
FIG. 55 depicts a display of an analysis device according to an exemplary embodiment of the present invention.

In some exemplary embodiments, to facilitate analysis of one or more sessions of athletic activity, display 402 of group monitoring device 400 or display 406 of analysis device 600 may display an analysis module, which may include utilities useable to analyze the session of athletic activity, as depicted in, for example, FIG. 55. Display 602 of analysis device 600 may display charts or graphs 618 that display metrics comparatively. For example, graph 618 may display heart rate for an individual 10 plotted over a session of athletic activity, or any other time period. Also displayed plotted on the same graph 610 may be other metrics, for example, training impact and mechanical power of individual 10. By plotting multiple metrics on the same graph 618, analysis device 600 may facilitate comparison of these metrics, and may evidence a correlation that can be useful to trainer 20 in monitoring the performance of individual 10.

Figure 56:
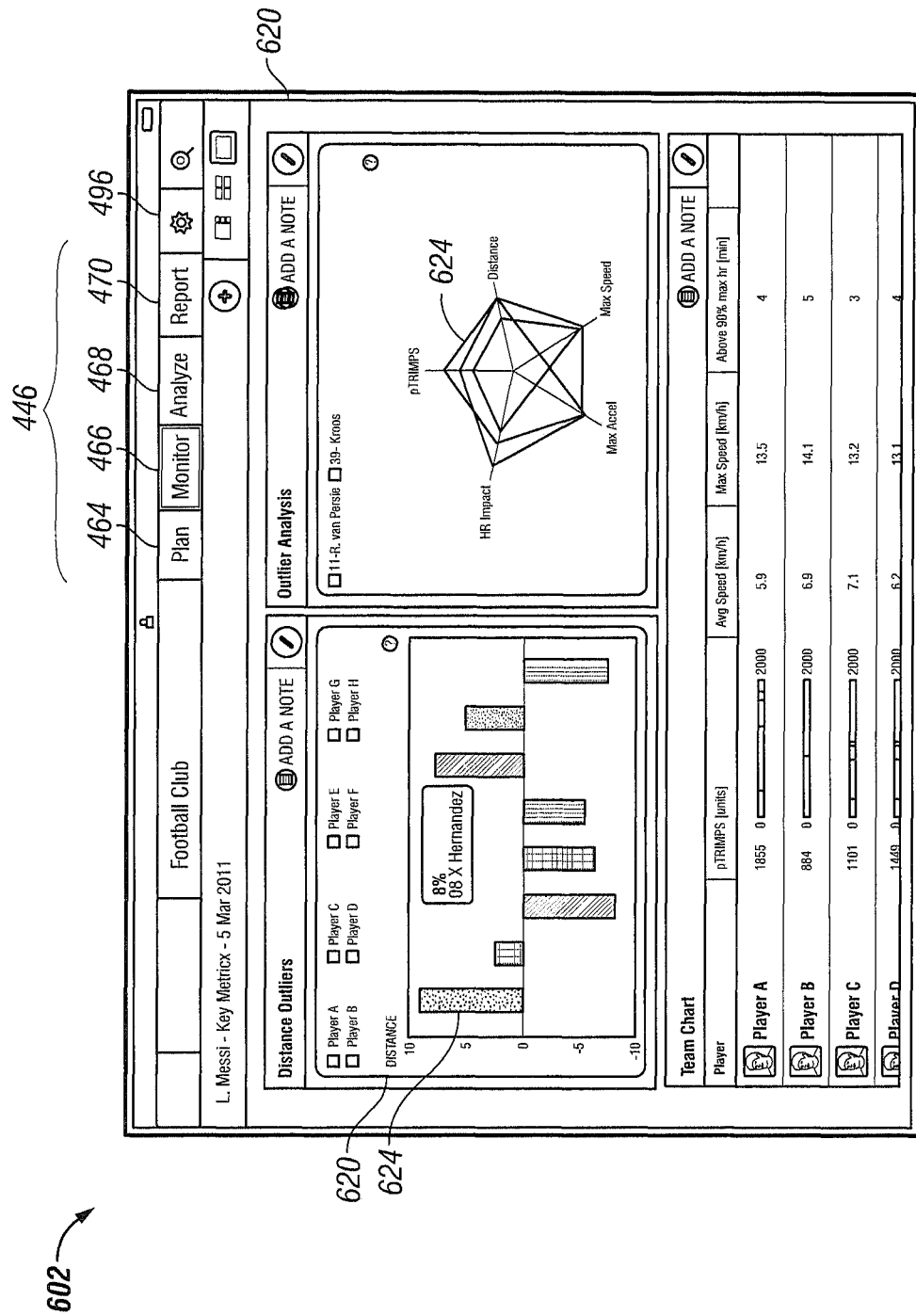
FIG. 56 depicts a display of an analysis device according to an exemplary embodiment of the present invention.

In some exemplary embodiments, as depicted in, for example, FIG. 56, display 602 of analysis device 600 may display outlier analyses 620 for comparing metric information of one or more individuals with one or more other individuals, and determining when one or more individuals have achieved a particular metric value that falls outside a baseline value. Outlier analyses 620 can be presented in a variety of ways, and can be useful in presenting data for multiple individuals 10 in a context that facilitates comparison of individuals 10. In some exemplary embodiments, a bar graph 622 showing percentage or value above or below an average (or other baseline) for a metric may be displayed. In some exemplary embodiments, a star graph 624 showing percentage or value of a variety of metrics for one or more individuals 10 may be displayed.

In some exemplary embodiments, analysis device 600 can recalculate past data based on new algorithms, thereby refining metric calculations or defining new metrics. In some exemplary embodiments, analysis device 600 can apply new alerts to past data. Such features can be useful to trainer 20 by facilitating historical investigation and analysis of data of individuals 10.

In some exemplary embodiments, analysis device 600 can be used by trainer 20 to predict future performance of individuals 10. Appropriate algorithms can be applied to past data that generate predictions of data of a future session for a particular player or group. For example, if a performance trend is recognized, it can be predicted that that trend may continue in a future session of athletic activity. Trainer 20 can use this information to inform decisions regarding future sessions of athletic activity.

Figure 57:
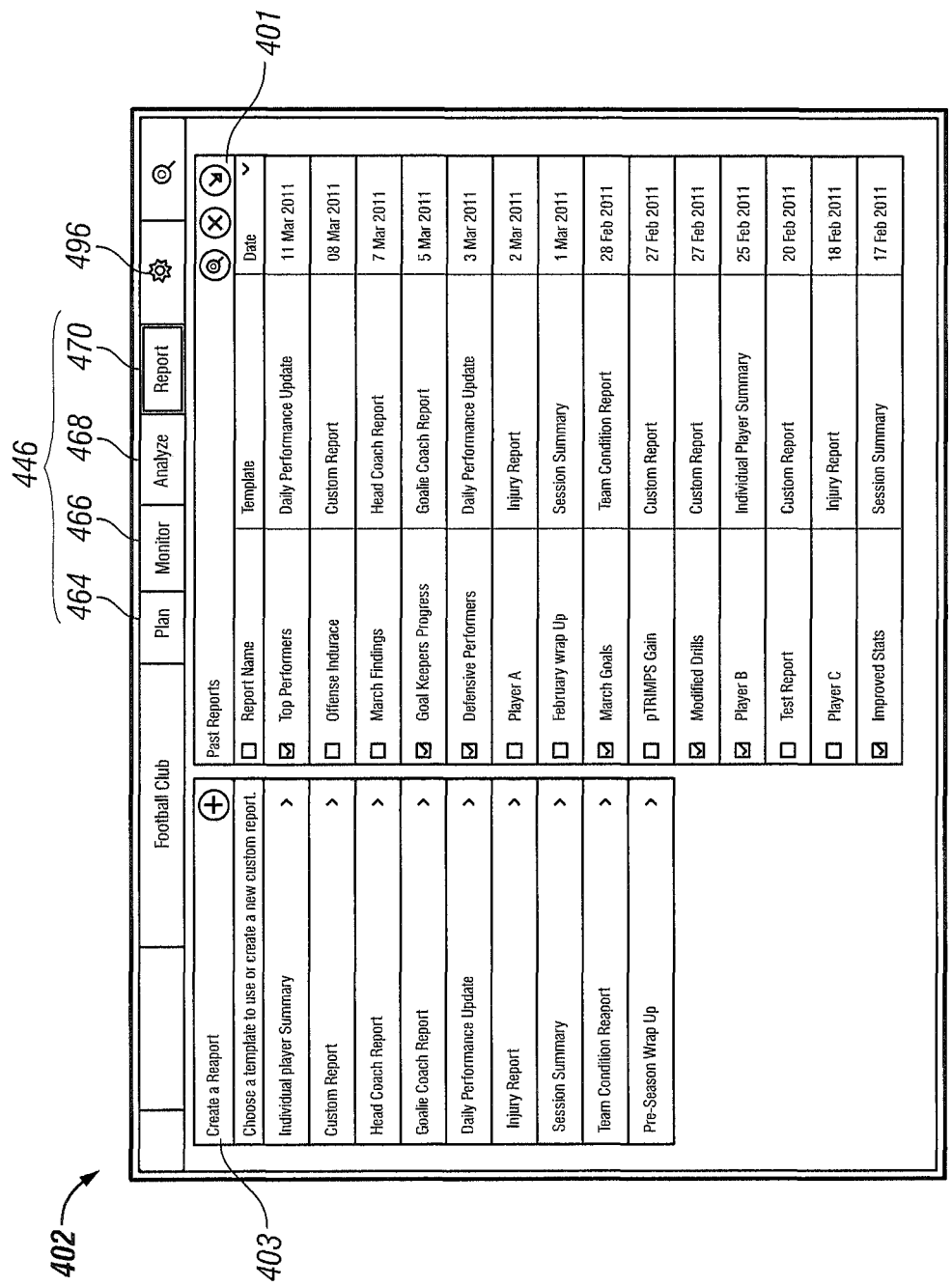
FIG. 57 depicts a display of a group monitoring device according to an exemplary embodiment of the present invention.
Figure 58:
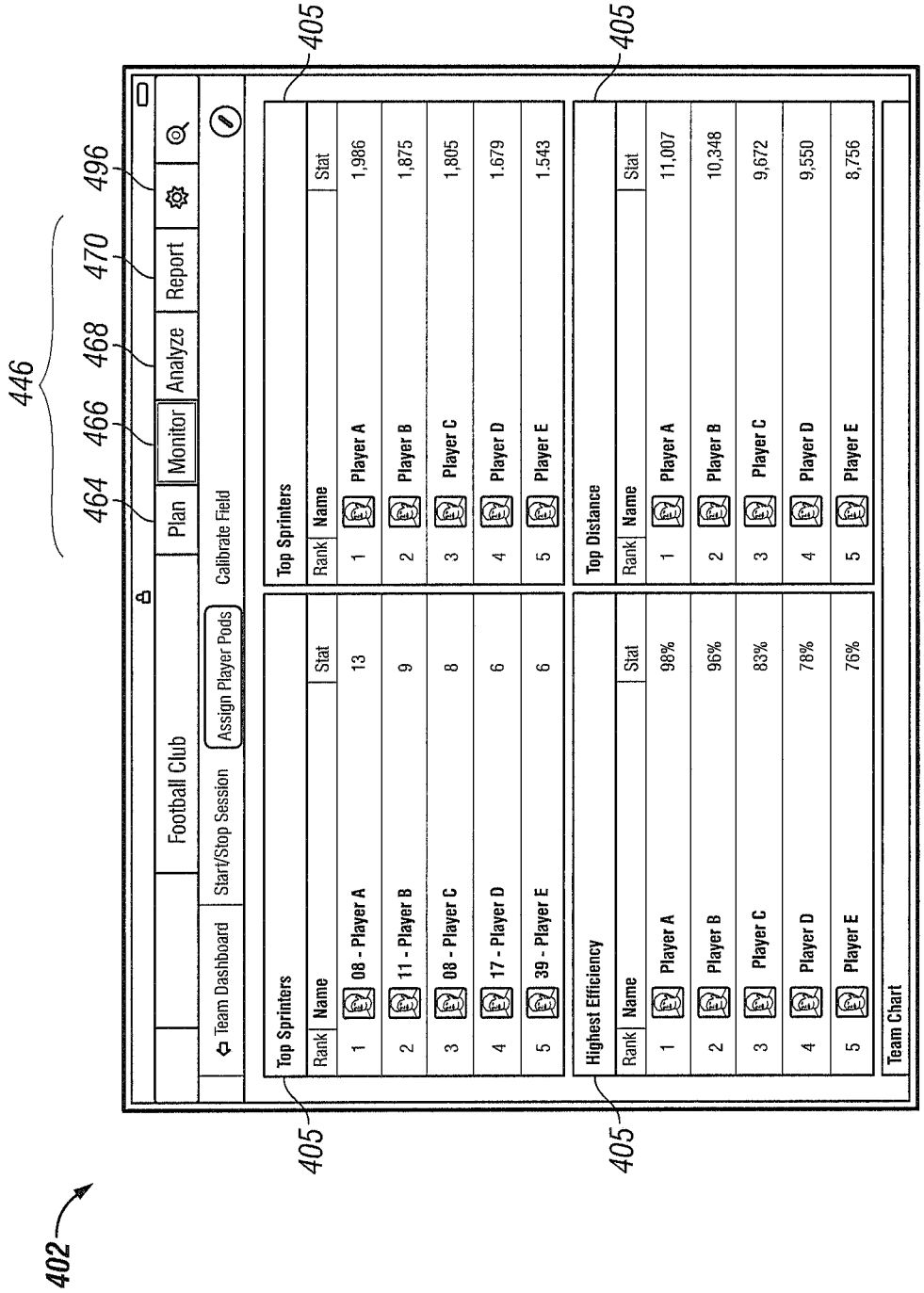
FIG. 58 depicts a display of a group monitoring device according to an exemplary embodiment of the present invention.
Figure 59:
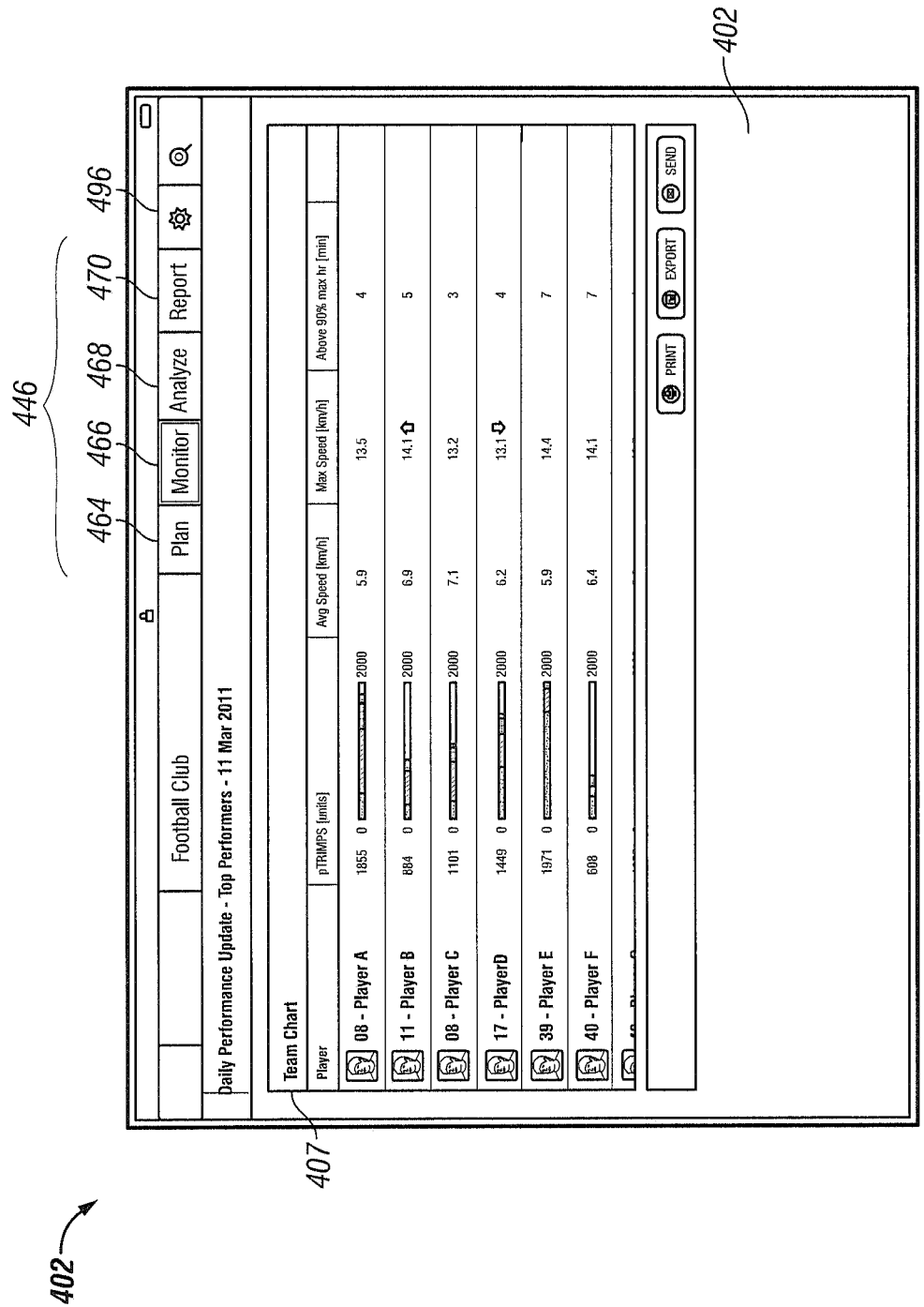
FIG. 59 depicts a display of a group monitoring device according to an exemplary embodiment of the present invention.

In some exemplary embodiments, as depicted in, for example, FIG. 57, group monitoring device 400 may include a report module, which may include a report generator 403 that allows a user to generate reports based on data and metrics of individuals 10. Reports can be predefined, or can be customized to generate desired information. A variety of types of reports can be generated, for example, individual player summaries, reports designed for a head coach, reports designed for a coach of a sub-group of a team (e.g., a goalie coach), daily performance update reports, injury reports, session summary reports, and team condition reports. For example, as depicted in FIGS. 58 and 59, a daily performance update may include information regarding top performing individuals 10. Such a daily performance update may include listings 405 showing individuals 10 that are top sprinters, are top power producers, have highest efficiency, and have top distance. In some exemplary embodiments, past reports can be saved and accessed from a past reports menu 401. Such a daily performance update may also include a team chart 407 showing present information for a group of individuals 10 making up a team. Team chart 407 may further indicate differences in the displayed information that may exist between the displayed information and information displayed in previous reports, thereby indicating changes in the performance of individuals 10.

In this document, terms such as "computer-usable medium" may be used to generally refer to media such as a removable storage unit or a hard disk installed in hard disk drive. Computer-usable medium may also refer to memories, such as a main memory or a secondary memory, which can be memory semiconductors (e.g., DRAMs, etc.). These computer program products provide software to computer systems and other components of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as, for example, determining, recording, and transmitting information related to individuals 10 engaged in an athletic activity, or presenting to a user of any of the herein-described displayable or audible elements (e.g., information related to individuals 10 engaged in an athletic activity). Information and/or instructions (e.g., a computer program product) for maintaining and/or rendering any module, function, or feature described herein (e.g., plan module, monitor module, analyze module, report module) may be stored in a computer-useable medium (e.g., memory or database) of any component described herein (e.g., base station 300, individual monitors 200, group monitoring device 400, web server system 500, analysis device 600, camera monitoring system 700, and/or video feed system 800).

In some exemplary embodiments, the one or more processors can be part of a computing device incorporated in a clustered computing environment or server farm. In some exemplary embodiments, the computing process performed by the clustered computing environment may be carried out across multiple processors located at the same or different locations. In some exemplary embodiments, the one or more processors can be part of any of the components described herein (e.g., base station 300, individual monitors 200, group monitoring device 400, web server system 500, analysis device 600). In some exemplary embodiments, one or more of the plan module, monitor module, analyze module, and report module may comprise, for example, an application for a device such as a smartphone, and may be configured to be downloaded in whole or in part.

Software of the present invention may be stored on any computer-usable medium. Such software, when executed in one or more data processing devices, such as, for example, any suitable component described herein (e.g., base station 300, individual monitors 200, group monitoring device 400, web server system 500, analysis device 600) causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

In some exemplary embodiments, group monitoring system includes a camera monitoring system 700, which may include, for example, one or more video cameras trained on playing field 30 in order to record image data indicative of motions of individuals 10. This image data can be transmitted to base station 300 (e.g., to data processing module 304 of base station 300), and can be used in the determination of metrics in much the same way as described above with reference to data transmitted from individual monitors 200. This image data can be stored in base station database 316, and can be transferred to web server system 500 (e.g., via central sync module 310), where it can be accessed by a video feed system 800 and displayed by a video display 802 of video feed system 800.

In some exemplary embodiments, video feed system 800 includes a video feed camera 804. Video feed camera 804 can also be trained on playing field 30 to record image data. This image data can be transmitted to web server system 500 to be retrieved for later viewing by video display 802 of video feed system 800.

Image data recorded by camera monitoring system 700 and/or video feed system can be accessed from web server system 500 by analysis device 600 and displayed on display 602 of analysis device 600.

In some exemplary embodiments, camera monitoring system 700 can be used to determine positions of individuals 10. Image data generated by camera monitoring system 700 can be received by base station 300 and analyzed to determine positions of individuals 10 and/or other objects/areas of interest. Camera monitoring system 700 can be used in this way to replace or supplement position sensor 208, and may be particularly useful for determining position in an indoor area or an area that otherwise receives no (or a weak) GPS or other positioning signal.

In some exemplary embodiments, image data generated by camera monitoring system 700 can be overlaid or identified with data and metrics described herein. In such an embodiment the image data may be displayed synchronously with the data and metrics by or in conjunction with a display device (e.g., group monitoring device 400 or analysis device 600). This can help correlate data and metrics with actual images of individuals 10.

A metric may be a representation of data indicative of a characteristic of individual 10 sensed as described above, or may be a representation of a characteristic derived from such data. In general, group monitoring system 100 can operate as a multi-level analysis tool. In an exemplary embodiment, group monitoring system 100 can use signals from an accelerometer, GPS sensor, electrocardiograph (ECG), gyroscope, clock, and magnetometer to directly determine data indicating heart rate, position, orientation, activity, and time related to each monitored individual 10. This data can be processed to calculate metrics including mechanical power, mechanical power zones, speed, speed zones, metabolic power, metabolic power zones, motion state, and distance. These metrics can be processed in conjunction with values indicating time, mass of each individual 10, and motion state of each individual 10, to calculate metrics including fatigue, training impact (TRIMPS), acceleration zones, acceleration work, efficiency, total distance, and acceleration.

Though particular metrics have been described above in the context of the described exemplary embodiments, these particular metrics are exemplary only, and other metrics besides those particularly disclosed may be used in the described exemplary embodiments. Examples of metrics are presented below in Table 1.

TABLE 1

Metric Examples

Acceleration
Epoch acceleration (mean accelerometer output over defined epoch)
Peak acceleration (maximum positive acceleration for a defined period)
Peak acceleration trend (plot of peak positive acceleration as a function of successive defined periods)
Average acceleration (mean positive acceleration for a defined period)
Average acceleration trend (plot of average acceleration as a function of successive defined periods)
Deceleration
Peak deceleration (maximum negative acceleration for a defined period)
Peak deceleration trend (plot of peak negative acceleration as a function of successive defined periods)
Acceleration zones (accumulated time spent in defined acceleration zones)
Collision impact (e.g., energy absorbed)
Training impact/TRIMPS (heart rate-or power-based)
Activity type
Step rate
Stride length
Time of ground contact (e.g., per step, or for a defined period)
Heart rate
Individual heart rate zones
Heart rate recovery
Heart rate recovery assessment (rate of recovery)
Location and Orientation (coordinate location, may be relative to base station) (e.g., x, y, z)
Location and Orientation (heat map) (e.g., 2 dimensional histogram of position)
Location and Orientation (movement path) (e.g., 2 dimensional time series plot)
Location and Orientation (relative to playing field) (e.g., standing, falling, laying down)
Location and Orientation (relative to playing field) (e.g., facing opposing goal)
Location and Orientation (relative to athletic activity equipment) (e.g., facing ball)
Location and Orientation (heading, absolute, relative to Earth) (e.g., facing east)
Location and Orientation (on-field spacing)
Location and Orientation (distance between individuals and/or objects)
Speed
Peak speed (maximum speed for a defined period)
Peak speed trend (plot of peak speed as a function of successive defined periods)
Average speed (mean speed for a defined period, may discount speeds below a defined threshold to account for non-mobile time)
Average speed trend (plot of average speed as a function of successive defined periods)
Speed zones (accumulated time spent in defined speed zones)
Distance traveled
Vertical displacement (time off of ground)
Vertical displacement (height)
Work (training load) (e.g., intensity over time; may take into account a combination of, for example, distance, number of sprints, number of accelerations/decelerations, time in speed zones, time in acceleration zones, body weight)
Work (mechanical work) (e.g., energy required to move individual through a distance)

TABLE 1-continued

Metric Examples

Work (power/intensity) (e.g., rate of doing work, power delivered, energy converted from chemical to mechanical)
Work (energy expenditure) (e.g., energy used to deliver mechanical work)
Work (efficiency) (e.g., ratio between energy expended and work; may account for state of body resulting from, for example, mental state, sleep, diet)
Power (constant power) (e.g., lactate threshold assessment, ventilatory threshold assessment)
Power (power output) (e.g., related to distance or acceleration)
Power (relative power output) (e.g., normalized to an individual's constant power at a point in time)
Power (acceleration)
Power (relative training impact) (e.g., cumulative power delivered over time, weighted by zones or activities)
Power (calories) (e.g., metabolic consumption, energy expenditure) (e.g., based on heart rate and accelerometry)
Power (activity)
Efficiency/performance effectiveness (relative efficiency) (mechanical power generated divided by metabolic energy consumption, e.g., normalized based on a known maximum state)
Efficiency/performance effectiveness (linear running efficiency) (e.g., efficiency of forward power vs. total power)
Efficiency/performance effectiveness (absolute efficiency) (e.g., ratio of absolute mechanical work to calories)
Fatigue (physiologic response to training load, measure of total work done) (e.g., change in EMG (electrogyogrphy) wavelet frequency, summed calorie rate consumption vs. expected standard, change in accelerometer spectral content, decay in sprint speeds, lengthening recovery times, change in heart rate recovery after exertion)
Core body temperature
Respiration rate
Running based Anaerobic Sprint Test (RAST)
Multi-stage fitness test performance (also known as the Yoyo test or beep test)
Maximal oxygen consumption (also known as $VO_2$ max)
Perceived exertion
X meter sprint performance (where X is a defined distance)
Blood lactate level The metrics described herein can relate to an individual (such as individual 10), a base station (such as base station 300), any relevant athletic equipment, or other persons or objects to the extent possible, necessary, or desired. The metrics described herein are exemplary, and other metrics besides those disclosed herein are useable with the present invention, as would be appreciated by one of skill in the art.

The present invention has been described above by way of exemplary embodiments. Accordingly, the present invention should not be limited by any of the above-described exemplary embodiments, but should be defined only in accordance with the following claims and their equivalences.

What is claimed is:

1. A system, comprising:
   a plurality of individual monitors each configured to be worn by a respective individual, wherein each individual monitor among the plurality of individual monitors comprises an acceleration sensor; and
   a group monitoring device comprising one or more computer processors configured to determine activities performed by individuals wearing individual monitors among the plurality of individual monitors by processing acceleration measurements obtained from the acceleration sensors;
   wherein the group monitoring device comprises a display configured to display a timeline, and the group monitoring device is configured to place markers on the timeline in response to user inputs to the group monitoring device.

2. The system of claim 1, wherein the activities are selected from the group consisting of: a sport, a movement, and a drill.

3. The system of claim 1, wherein each individual monitor among the plurality of individual monitors further comprises a magnetometer and a gyroscope.

4. The system of claim 3, wherein the one or more computer processors are configured to process the acceleration measurements from the acceleration sensor, magnetometer data from the magnetometer, and gyroscope data from the gyroscope to determine the activities.

5. The system of claim 3, wherein the one or more computer processors are configured to process the acceleration measurements, magnetometer data from the magnetometer, and gyroscope data from the gyroscope to determine a posture of the individuals.

6. The system of claim 1, wherein the markers define a portion of the activity one of the individuals is performing, and wherein the portion is selected from the group consisting of: a warmup, live play, a cool down, a line drill, sprints, repeated sprints, a conditioning drill, a strength training drill, a tactical drill, or a skills drill.

7. The system of claim 1, wherein each individual monitor among the plurality of individual monitors comprises a magnetometer, and wherein the one or more computer processor are configured to process acceleration sensor data and magnetometer data to determine a heading of the individuals.

8. The system of claim 1, comprising a plurality of sensors configured to communicate with the individual monitors and to be worn together with the individual monitors on different parts of the individuals from the individual monitors.

9. The system of claim 1, wherein the group monitoring device is configured to process the acceleration measurements to calculate metrics of the individuals wearing individual monitors, and wherein the metrics comprise any one or any combination of mechanical power, mechanical power zones, speed, speed zones, metabolic power, metabolic power zones, motion state, and distance traveled.

10. The system of claim 1, wherein the one or more computer processors are configured to process data from the individual monitors to make body motion determinations.

11. A system, comprising:
an individual monitor configured to be worn by an individual, wherein the individual monitor comprises an acceleration sensor; and
a group monitoring device comprising one or more computer processors configured to process acceleration measurements obtained from the acceleration sensor to determine an activity the individual wearing the individual monitor is performing;
wherein the one or more computer processors are configured to process data from the individual monitor to make body motion determinations, and
wherein the individual monitor comprises a magnetometer module and a gyroscope module, and wherein the group monitoring device is configured to use the acceleration sensor, the magnetometer module, and the gyroscope module to calibrate the body motion determinations.

12. The system of claim 11, wherein the acceleration sensor is a three-axis acceleration sensor.

13. The system of claim 10, wherein the individual monitor comprises a magnetometer module and a gyroscope module, and the group monitoring device is configured to process data from the magnetometer module to calibrate body motion data determined by the gyroscope module and the acceleration sensor.

14. The system of claim 11, further comprising a position module configured to determine data indicative of absolute position of the individual.

15. The system of claim 14, wherein the group monitoring device is configured to use the acceleration measurements to increase accuracy of the data indicative of absolute position of the individual.

16. A system, comprising:
an individual monitor configured to be worn by an individual, wherein the individual monitor comprises an acceleration sensor;
a group monitoring device comprising one or more computer processors configured to process acceleration measurements obtained from the acceleration sensor to determine an activity the individual wearing the individual monitor is performing; and
a position module configured to determine data indicative of absolute position of the individual;
wherein the one or more computer processors are configured to process data from the individual monitor to make body motion determinations,
wherein the group monitoring device is configured to use the acceleration measurements to increase accuracy of the data indicative of absolute position of the individual by using the acceleration sensor to determine a filter for a global positioning system signal calculation.

17. The system of claim 11, wherein the body motion determinations comprise one or more of an impact, a change in motion, and step counting.

18. The system of claim 17, wherein the body motion determinations comprise a determination of which movement the individual is performing.

19. The system of claim 11, wherein the body motion determinations comprise metrics of the individual, and wherein the metrics comprise any one or any combination of mechanical power, mechanical power zones, speed, speed zones, metabolic power, metabolic power zones, motion state, and distance traveled.

20. A system, comprising:
an individual monitor configured to be worn by an individual, wherein the individual monitor comprises an acceleration sensor; and
a group monitoring device comprising one or more computer processors configured to process acceleration measurements obtained from the acceleration sensor to determine an activity the individual wearing the individual monitor is performing;
wherein the individual monitor further comprises a magnetometer and a gyroscope; and
wherein the one or more computer processors are configured to process the acceleration measurements, magnetometer data from the magnetometer, and gyroscope data from the gyroscope to determine a posture of the individual.

21. A system, comprising:
an individual monitor configured to be worn by an individual, wherein the individual monitor comprises an acceleration sensor; and
a group monitoring device comprising one or more computer processors configured to process acceleration measurements obtained from the acceleration sensor to determine an activity the individual wearing the individual monitor is performing;
wherein the individual monitor comprises a magnetometer, and wherein the one or more computer processor are configured to process acceleration sensor data and magnetometer data to determine a heading of the individual.

\* \* \* \* \*